United States Patent
Scarpone

(10) Patent No.: US 12,005,048 B2
(45) Date of Patent: Jun. 11, 2024

(54) METHODS AND DEVICES FOR HARVESTING AND PROCESSING CONNECTIVE TISSUE PRECURSOR CELLS FROM AUTOLOGOUS FAT

(71) Applicant: Michael A. Scarpone, Bloomingdale, OH (US)

(72) Inventor: Michael A. Scarpone, Bloomingdale, OH (US)

(73) Assignee: Michael A. Scarpone, Bloomingdale, OH (US)

( * ) Notice: Subject to any disclaimer, the term of this patent is extended or adjusted under 35 U.S.C. 154(b) by 252 days.

(21) Appl. No.: 17/404,276

(22) Filed: Aug. 17, 2021

(65) Prior Publication Data

US 2021/0380927 A1 Dec. 9, 2021

Related U.S. Application Data

(62) Division of application No. 15/600,763, filed on May 21, 2017, now Pat. No. 11,091,732.

(51) Int. Cl.
*A61K 31/436* (2006.01)
*A61K 35/35* (2015.01)
(Continued)

(52) U.S. Cl.
CPC ............ *A61K 31/436* (2013.01); *A61K 35/35* (2013.01); *A61L 27/3633* (2013.01); *A61M 1/63* (2021.05);
(Continued)

(58) Field of Classification Search
CPC .......... A61M 1/71; A61M 1/63; A61M 1/892; A61M 1/895; A61M 2202/0014;
(Continued)

(56) References Cited

U.S. PATENT DOCUMENTS

| | | |
|---|---|---|
| 11,091,732 B2 | 8/2021 | Scarpone |
| 2012/0156177 A1 | 6/2012 | Scarpone |

(Continued)

FOREIGN PATENT DOCUMENTS

WO 2014112794 A1 7/2014

OTHER PUBLICATIONS

Abuzeni, P. Z., et al, "Enhancement of Autologous Fat Transplantation With Platelet Rich Plasma," American Journal of Cosmetic Surgery 18(2): pp. 59-70 (2001).

(Continued)

*Primary Examiner* — Sean C. Barron
(74) *Attorney, Agent, or Firm* — K&L Gates LLP

(57) ABSTRACT

Methods and devices are disclosed for processing stromal precursor cells (i.e., cells which can differentiate into connective tissue cells, such as in muscles, ligaments, or tendons) which can be obtained from fatty tissue extracts obtained via liposuction. Normal processing of a liposuction extract involves centrifugation, to concentrate the stromal cells into a semi-concentrated form called "spun fat". That "spun fat" can then be treated by mechanical processing (such as pressure-driven extrusion through 0.5 mm holes) under conditions which can gently pry the stromal cells away from extra-cellular collagen fibers and other debris in the "spun fat". The extruded mixture is then centrifuged again, to separate a highly-enriched population of stromal cells which is suited for injection back into the patient (along with platelet cells, if desired, to further promote tissue repair or regeneration).

14 Claims, 13 Drawing Sheets

(51) Int. Cl.
    *A61L 27/36*    (2006.01)
    *A61M 1/00*    (2006.01)
    *C12M 1/00*    (2006.01)
    *C12M 1/26*    (2006.01)
    *C12N 5/077*    (2010.01)
    *C12N 5/0775*    (2010.01)

(52) U.S. Cl.
    CPC .............. *A61M 1/71* (2021.05); *A61M 1/892* (2021.05); *C12M 33/10* (2013.01); *C12M 47/04* (2013.01); *C12M 47/08* (2013.01); *C12N 5/0653* (2013.01); *C12N 5/0667* (2013.01); *A61M 1/895* (2021.05); *A61M 2202/0014* (2013.01); *A61M 2202/0021* (2013.01); *A61M 2202/095* (2013.01); *A61M 2205/3331* (2013.01); *A61M 2205/3365* (2013.01)

(58) Field of Classification Search
    CPC .... A61M 2202/0021; A61M 2202/095; A61M 2205/3331; A61M 2205/3365; A61K 35/35; A61L 27/3633; C12M 33/10; C12M 47/04; C12M 47/08; C12N 5/0653; C12N 5/0667

See application file for complete search history.

(56) References Cited

U.S. PATENT DOCUMENTS

2012/0195863 A1* 8/2012 Alt ........................ A01N 1/0242
                                                    435/325
2015/0218506 A1* 8/2015 Nash ..................... C12N 5/0653
                                                    435/379

OTHER PUBLICATIONS

Pietrzak, W. S., et al, "Platelet rich plasma: biology and new technology," J Craniofac Surg. 16(6): pp. 1043-1054 (2005).
Maniscalco, P., et al, "The "Cascade" membrane: a new PRP device for tendon ruptures," Acta Biomed. 79(3): pp. 223-226 (2008).
Hall, M. P., et al, "Platelet-rich plasma: current concepts and application in sports medicine," J Am Acad Orthop Surg. 17(10): pp. 602-608 (2009).
Gociman, B., et al, "Caption™: a filtration-based platelet concentration system," Expert Rev Med Devices 6(6): pp. 607-610 (2009).
Lacci, K. M., et al, "Platelet-rich plasma: support for its use in wound healing," Yale J Biol Med. 83(1): pp. 1-9 (2010).
Lopez-Vidriero, E., et al, "The use of platelet-rich plasma in arthroscopy and sports medicine: optimizing the healing environment," Arthroscopy 26(2): pp. 269-278 (2010).
Encore™ 26 Inflator, www.bostonscientific.com/en-US/products/accessories/encore.html, 2021 Boston Scientific Corporation, 2 pages.
Francis et al., "Isolating adipose-derived mesenchymal stem cells from lipoaspirate blood and saline fraction", Organogenesis, 2010, 6(1), pp. 11-14.

* cited by examiner

METHODS AND DEVICES FOR HARVESTING AND PROCESSING CONNECTIVE TISSUE PRECURSOR CELLS FROM AUTOLOGOUS FAT

RELATED APPLICATIONS

This application is a divisional of U.S. patent application Ser. No. 15/600,763, filed May 21, 2017, now U.S. Pat. No. 11,091,732. The contents of which is hereby incorporated by reference.

BACKGROUND

This invention is in the field of medicine, surgery, and veterinary medicine. It relates to devices and methods for transplanting cells obtained from fatty tissue, in one region of a patient's (or animal's) body, into a different location in the same person's (or animal's) body, for purposes such as: (i) repairing damaged connective tissue, in locations such as joints, muscles, tendons, ligaments, etc; and, (ii) cosmetic and other appearance-related surgery, such as scar revisions, repair of congenital defects, and surface enhancements.

When used to refer to surgical procedures, the terms "autologous transplantation" and "auto-transplantation" are used interchangeably. The term "autologous" indicates that living cells are removed, extracted, or otherwise obtained from one portion of a person's body, and are subsequently implanted, transplanted, injected, or otherwise emplaced in a different location in the body of that same person. Except in rare cases that do not require attention here (involving autoimmune disorders and the like), autologous cells (defined to include cells obtained from the same animal or human body that will be receiving the transplanted cells) do not create a risk of rejection by the patient's body.

In some situations, autologous transplanted tissues remain in cohesive form. Examples include blood vessel grafts, skin grafts, etc. Those types of surgery are not relevant herein.

In the surgical procedures of interest herein, cells will be extracted in a liquefied form, from fatty tissue within a patient's body, using methods that fall within the medical term "liposuction". The term "lipo-" refers to fat or fatty; accordingly, "liposuction" is used broadly herein, to refer to and include any type of procedures which uses suction (via a hollow needle, cannula, or other tube) to remove fat-containing tissue from the body of a human or other mammal. Since suction of tissue through a needle, cannula, or other tube is involved, the tissue which passes through the tube will necessarily be in some type of a liquefied form, and "liquefied" is used broadly herein, to include thick and viscous cell suspensions that might also be referred to as a paste, slurry, sludge, gel, or similar terms.

The phrase, "autologous fat grafting" (abbreviated as AFG) is often used in the medical literature, to refer to the types of procedures described herein. However, that phrase is not used herein, since it is potentially misleading, since "fat" will not be transplanted back into the patient. Instead, the desired and targeted cells that are useful for these types of procedures are a specialized class of cells, referred to herein interchangeably as either "stromal precursor cells" or "connective tissue precursor cells". Those are described in some detail, below. By means of certain types of processing steps described below, those cells are extracted from the liquefied fatty tissue that is obtained via liposuction, and extracellular fat (which initially accompanies those desired cells, in the liquefied tissue obtained via liposuction) preferably should be removed and discarded.

References herein to surgery (and to "surgical" procedures, operations, and the like) refer to and include medical interventions that involve physical manipulation of tissue (as distinct from, for example, diagnosing a condition and prescribing a drug to treat the condition). For the purposes of discussion herein, liposuction is deemed to be a type of surgery, and the medical interventions described herein are deemed to be "surgical" interventions. In the US and elsewhere, these types of procedures can be performed, lawfully, only by properly trained and licensed physicians; however, there are multiple thousands of physicians, in the US, who have the skills and ability to perform these procedures. Accordingly, even though substantial attention is devoted herein to the steps and devices that are used to carry out the procedures described herein, it should be recognized and understood that the level of "ordinary skill in the art" in this particular field includes physicians who already know how to perform liposuction, and who have done it multiple times, on multiple patients. Accordingly, the discussion herein of the steps, methods, devices, and equipment that are involved in liposuction must be regarded and understood as being mere summaries and overviews which are written for laymen, rather than as an instruction manual for physicians.

With regard to whether the term "surgery" is used appropriately to describe these procedures, it should be noted and understood that these procedures fall into a gray area, at the outer boundaries of "surgery". A large number of medical procedures and interventions involve borderline areas, where it is not clear whether they fall within either classic or contemporary definitions of "surgery". Indeed, an entire specialized branch of medicine has evolved during the past 20 years, which is commonly referred to as "sports medicine". Most of the procedures that are performed by "sports medicine" specialists involve repairs to connective tissues, which includes muscles, tendons, and ligaments. Physicians who specialize in this branch of medicine frequently perform procedures that fall within the classical definition of "surgery" (i.e., they involve the physical manipulation and alteration of living tissues, which passes beyond merely handling fluids, such as withdrawing blood). As part of that work, specialists in "sports medicine" frequently use needles, cannulas, catheters, and other minimally-invasive tools, to manipulate tissue. However, they usually do not refer to themselves as "surgeons", and they generally avoid the use of scalpels, incisions, or the types of surgery carried out by classical "surgeons" as that term is normally understood by laymen.

Accordingly, for the purposes of this invention, liposuction is deemed to be a form of "surgery", since it involves the physical manipulation of tissue, and therefore falls within the classic definition of the term. However, it should be recognized that not everyone refers to it as "surgery", and "sports medicine" specialists (who likely will be among the main practitioners of the methods described herein) usually do not refer to themselves as surgeons.

In addition, as will be recognized by veterinarians, the methods, devices, and cell preparations described herein can also be adapted for use in veterinary medicine, such as to treat pets, or livestock. For example, since numerous breeds of dogs suffer from congenital hip problems, a dog which is displaying symptoms of hip problems or discomfort can be injected with a cell preparation as described herein, into the hip area which is believed to be causing the problem, in the hope that such treatment will benefit the dog, and relieve or at least reduce its pain, in the same way that similar injections into knee or hips joints can benefit human patients suffering from hip or knee problems. For brevity and convenience, animal treatments will not be mentioned again, herein; however, any references to humans and/or patients should be regarded as being also adaptable, by skilled veterinarians, to pet and/or livestock animals; and, following a normal and conventional practice, the term "patient" includes animals which are veterinary patients.

Returning to the subject of autologous transplantation of connective tissue cells, fatty tissue (also known as adipose tissue) is readily available in any human who is not exceptionally slender. It contains large numbers of cells which fall within a category referred to herein, interchangeably, as either "precursor" or "progenitor" cells. Both of those two terms indicate that these cells have reached a stage of partial differentiation, and maturation. At that stage of development, they are able to complete a maturation process which will convert them into any of several different types of fully differentiated "adult" cells.

Because these matters are crucial to understanding this invention, and because certain terms that are important herein have taken on various implications and subtleties that sometimes vary and diverge, when used in the medical literature and the "popular press", a digression is required to address some of the terms used herein.

"Stem Cells" Versus "Precursor" or "Progenitor" Cells

Because of various factors that are involved in public, political, and legal battles over abortion and cloning, which are highly polarized and divisive areas, the term "stem cells" has taken on very different and even conflicting meanings, depending on who is using the term. Among reporters, the press, and the general public, "stem cells" implies and/or means the types of "embryonic" or "totipotent" cells which have a full, complete, and unlimited ability to develop into a complete adult. Accordingly, under the "general public and mass media" definition and interpretation, the term "stem cell" is used only to refer to cells which have the potential to differentiate into ANY type of cell that is found in a fully matured and differentiated adult.

However, in the scientific and medical literature, a very different set of meanings and implications arise. Under this definition, any cell that has not yet fully differentiated into an "irrevocably committed and fully differentiated" adult cell will properly fall within the term, "stem cell". Stated in other words, any cell which still has a potential to differentiate into either of at least two (or more) different types of adult cells, is called a "stem cell". This is similar to the way any "stem" in nearly any type of a plant can have multiple leaves emerge from it.

The medical definition arose, after developmental biologists discovered and realized that "stem cells" pass through a series of different stages, involving partial levels or degrees of what can be called "differentiation" or "commitment". At the very earliest stage of embryonic development, immediately after a sperm cell and an egg cell have combined, the resulting cell (and the cells which arise during the first few cycles of replication) are called "totipotent" or "omnipotent" stem cells, because they can become ANY type of cell found in an adult. However, that stage is very brief, and it lasts only until a fertilized egg has divided into about 4, 8, or 16 cells, depending on the species.

When stem cells pass beyond that early and brief "totipotent" or "omnipotent" stage (which lasts for only a few cell divisions), most of the cells which are found in a fetus become "multipotent" (also called "pluripotent") stem cells. At that stage of maturation and "commitment", they can still mature into numerous different types of cells; however, the pathways they can follow begin to become constrained, in various ways, and they can no longer form every cell type that exists in an adult animal of that species.

For example, during the early development of a human or other mammalian embryo, some cells will move into a segment of developing tissue which will become the liver. For at least some period of time, these early progenitor cells will have the ability to become any type of liver cell, and there are numerous different types of liver cells. However, under natural conditions that exist within an embryo, an embryonic stem cell which has committed to becoming a liver cell will not be able to back up, move over to a different development pathway, and become a heart cell, a brain cell, or any other type of non-liver cell.

Throughout all stages of infancy, adolescence, and adulthood, every internal organ contains numerous "multipotent" or "pluripotent" stem cells. In any particular organ, these types of cells will retain the ability to complete a process of differentiation and maturation, in a manner which can create a variety of different types of new cells, which can replace aging cells that can no longer fully perform their cellular functions. This is an absolutely crucial function, which is described in more detail below, and it helps explain the surprisingly large number of such cells, in fatty tissue. Under the medical definition, these types of "multipotent" or "pluripotent" precursor cells are labeled as "stem cells". However, that use of the term directly conflicts with the "general public and mass media" definition of "stem cells".

Accordingly, to avoid "unwanted baggage, and unintended meanings" that can arise when "stem cells" are being discussed, that term is not preferred herein, and terms that are more scientific and less divisive are used, such as "progenitor" or "precursor" cells.

Two additional terms requires attention; those terms are "stroma" and "stromal". In medical terminology, the term "stroma" refers to the biomechanical framework (or scaffolding, matrix, support, or similar terms) of an internal organ, muscle, or similar non-bony tissue. The corresponding adjective is "stromal". Accordingly, stromal cells include cells which contribute to the strength, cohesiveness, flexibility, elasticity, integrity, and other structural and biomechanical traits of an organ, muscle, tendon, ligament, or other type of connective tissue. Since the types of stromal tissue that is of interest herein is also referred to as "connective tissue", the term "stromal precursor cells" is used interchangeably with "connective tissue precursor cells".

Briefly, "stromal precursor cells" includes cells which still have an ability to differentiate and mature into any of several different types of connective tissues, which can include muscles, tendons, ligaments, etc. Accordingly, these types of precursor cells are of great interest to "sports medicine" specialists, and to any physicians who are faced with the task of repairing, reconstructing, or supplementing various types of connective tissues that have become injured, infected, chronically sore, or otherwise damaged, or which suffer from congenital defects, problems that have arisen due to aging or senescence, etc. For convenience, connective tissue which is suffering from any of those types of conditions, at a level severe enough to require or merit medical intervention as described herein, is referred to herein as "damaged" tissue.

Types and Examples of Connective Tissue Repairs

Because of various aspects of human physiology and activity (which lead to different types of stresses being imposed on different joints), the most common types of connective tissue injuries or problems involve certain specific joints, including the following:

1. rotator cuff problems, problems involving certain other muscles, tendons, and/or ligaments, in shoulder joints;

2. hip and/or groin problems, involving either "hyaline" cartilage (i.e., the type of smooth-surfaced cartilage which coats a bone surface in an articulating joint), or various types of strains, tears, or other injuries to muscles, tendons, or ligaments in the region of the pelvis and upper thighs;

3. knee problems, which can include cartilage, ligament, tendon, or muscle problems;

4. ankle problems;

5. finger, thumb, wrist, or hand problems; and, 6. elbow problems, often referred to as "tennis elbow" regardless of whether tennis was involved.

In addition to those types of problems, various types of skin ulcerations (typified by bedsores, also called decubitis ulcers) occur in various types of patients, especially patients suffering from diabetes, obesity, or other types of circulatory, metabolic, or "ambulatory" (walking) problems. These types of ulcers, which typically are called skin ulcers to distinguish them from stomach ulcers (and to identify them as a class of ulcers that are readily visible on skin surfaces), frequently involve damage to underlying tissues as well, including muscles, tendons, and ligaments. They occur most frequently around the feet and ankles (because of circulatory issues), or on body surfaces that tend to be pressed against bedding materials for hours at a time during sleep, especially among the elderly.

In addition, treatments using the types of cell preparations disclosed herein appear to be ideally suited for new mothers, immediately after childbirth. For example, they may be able to help accelerate the healing of, and improve the appearance and functionality of, any internal and external cuts or tearing that occurred during, for example, a Caesarian delivery, episiotomy, or delivery of an exceptionally large baby.

In addition to those types of uses, stromal precursor cells also can be useful for reconstructing or altering the appearance of various types of scars, and for similar types of surgery which can be generally classified as cosmetic surgery (i.e., surgery, injections, or other interventions in which alterations to appearance are of primary or major importance). A useful example can be offered by the repair of so-called "cleft palates", in children who are born with a "missing tissue" type of defect in their upper lips. Those and numerous other types of scars, defects, or irregularities can be rendered less noticeable and obvious, by injecting additional material into either: (i) a "deficit" type of location, in order to effective fill up that deficit; or, (ii) adjacent locations, if the goal is to reduce the appearance and distractions of an irregular and unwanted crest, promontory, or similar problem. Similarly, cosmetic alterations are often performed on people who have reached middle age or older, to reduce or reverse various types of gradual facial or other tissue changes which accumulate as people age through adulthood.

Accordingly, the types of "stromal precursor cells" which have already reached a state of partial differentiation, and which can complete a maturation process that will convert them into muscle, tendon, ligament, or other connective tissue cells, are of great interest, for the types of medical treatments described herein. Stromal precursor cells from autologous fatty tissue can be used to help repair muscles, tendons, ligaments, and other connective tissues that have been injured or otherwise damaged in various ways, or which have been surgically removed or otherwise manipulated (such as during removal of a tumor, cyst, or other injured, damaged, or unwanted tissue). They also can be used to help repair, regenerate, or replace tissue that was damaged by infection, trauma, disease, or other events, conditions, or problems, or which cause unwanted displays of aging. Accordingly, if properly performed, these types of autologous transplantations of stromal precursor cells, from fatty tissue, can help patients recover from sports injuries, injuries suffered during various types of accidents or trauma, infections by pathogenic microbes that attack connective tissues, and similar problems. They also can be used for various types of cosmetic and/or reconstructive surgery, such as for scar revision, repair of cleft palates, removal or reduction of skin lines and creases, etc.

Importantly, those types of stromal precursor cells are present in surprisingly high numbers, in fatty tissues, because of an important cellular and physiological process.

Apoptosis; Active and Ongoing Cell Replacement in Soft Tissues

As mentioned above, because of a crucially important and highly active cellular process that occurs in all mammals, there are surprisingly large numbers of stromal precursor cells, in fatty tissue. While it is not crucial to fully understand the natural cellular process in order to understand this invention, a working knowledge of it can help the reader reach a better understanding of how and why this invention works.

Cells that reach an advanced stage of aging are often referred to as "senescent", which derives from the same root word as "senile". In the same way that a senile person might be able to live for many years, if properly taken care of by other people, senescent cells remain viable, as living cells, but they have lost the ability to fully perform their normal functions.

Severe health problems and major biological inefficiencies would arise, if muscles or other tissues in an animal had to devote part of their resources to nurturing, nursing, and providing for senescent cells, in an effort to keep them alive for as long as possible even after they lost the ability to perform their essential functions. To avoid those problems, mammalian cell biology evolved in a different direction. Rather than keeping cells alive for as long as possible, even after they can no longer perform their essential functions, mammalian biology evolved in ways that rapidly identify, kill, recycle, and replace aging and senescent cells with new cells, in a constant process of cell turnover and replacement. This process involves a well-known cellular activity called "apoptosis", sometimes referred to as "programmed cell death". This process is controlled by mitochondria, which are tiny "organelles" that have their own membranes, inside mammalian cells. These organelles are the remnants of tiny anaerobic bacteria, which initially invaded larger cells, and which then created a symbiotic relationship with their "host" cells. A typical cell has dozens or even hundreds of mitochondria, inherited entirely from the mother, with no genetic contribution from the father. These organelles are enclosed within their own membranes, and they carry their own DNA, which even has its own specialized genetic code, which is different from the genetic code used by the chromosomes in the nucleus of a cell.

Mitochondria are the "cellular furnaces", where glucose (the main energy supply for any mammalian cell) is oxidized and "burned", to convert the glucose into carbon dioxide and water, in a way that releases energy which a cell can use. As a result, the chemical mixtures inside mitochondria are relatively harsh, since destructive "oxygen radicals" are constantly being generated, as a byproduct of glucose oxidation in the mitochondria. As a result, the membranes which enclose the mitochondria are chemically attacked and degraded, at relatively rapid rates.

In an aging cell, when the mitochondrial membranes become worn out and degraded to a point where they become permeable, they begin releasing a specific molecule called "cytochrome c". That messenger molecule activates a sequence of events, which will culminate in a "macrophage" (a specialized white blood cell) engulfing, killing, and digesting the aging cell. This frees and releases molecular building blocks (such as amino acids, nucleotides, etc.), which will be used to make new cells, to replace the senescent cells that were killed and digested.

That type of "programmed cell death" is essential for keeping muscles, tendons, ligaments, internal organs, and other tissues vigorous and fully functional for spans of time measured in years or even decades. Except for neurons (which are in a special class), the typical lifespan of any particular cell, in any large animal, is only a few weeks or months, and the process which recycles and replaces aging cells with new cells, in any particular type of tissue, is very active at all times.

Therefore, the presence of large numbers of precursor cells which have reached a moderately advanced stage of development and differentiation, and which can complete the final steps of maturation into any particular type of "adult" cell which is needed in some particular location at a specific time, is crucially important to the process of constantly replacing aging cells with new cells. In any organ, joint, or other "subassembly" which contains multiple cell types, a rich supply of partially-differentiated precursor cells, which required a substantial amount of time to reach that stage of development but which can rapidly undergo the last and final steps in a differentiation and maturation process that will create fully "adult" cells, is an essential part of the natural process of replacing old cells with new cells.

That is a well-known feature of mammalian physiology, and over the past decade, major advances have been made that allow physicians to extract and obtain large numbers of stromal precursor cells, from fatty tissues that can be obtained in a minimally-invasive manner, via liposuction.

Conventional Liposuction Procedures and Equipment

Conventional and well-known methods can be used to obtain stromal precursor cells from fatty tissue, via liposuction. These methods are taught in courses that are taken by surgeons and other doctors who wish to learn to perform these procedures, and the types of cannulae, syringes, and other kits, devices, and machines that are used during this type of liposuction are readily available. For example, a website at www.viafill.com illustrates the VIAFILL™ system, sold by the Lipose Corporation and specifically designed for the type of liposuction described herein.

Rather than resembling the types of enlarged cannulae that are used to remove large amounts of fatty tissue for the purpose of weight reduction, a cannula designed to harvest viable stromal cells for autologous transplantation has dimensions that are similar to an enlarged hypodermic needle. This type of cannula is made of a rigid metal alloy, and has a smooth rounded tip that will not readily puncture, cut, or damage muscles or membranes. A series of medium-sized holes (or orifices, channels, or similar terms) pass through the sides of the barrel, in a region near the tip of the cannula.

Before this type of cannula is inserted into a patient's body, a hypodermic needle (with a very thin barrel, and a very sharp beveled tip) is used to inject a topical anesthetic (such as xylocaine) under the skin, at the location that will be worked on. Typically, the first anesthetic needle is withdrawn, and after the first batch of anesthetic drug has taken effect and partially numbed the area, a second hypodermic needle is inserted, and moved around a semi-circular area, to spread additional anesthesia into the area beneath the skin (this is often called a "fanning" procedure or pattern, since the affected area resembles the shape of a semi-circular hand-held fan). The needle is kept nearly tangential to the skin, so that the tip does not penetrate into any major muscles, and remains in a shallow layer of fat between the muscles and the skin.

Typically, as the second anesthetic needle is being withdrawn, the sharp tip is used to create an enlarged nick in the skin. The smooth rounded tip of an injection cannula (which closely resembles or which can be identical to the extraction cannula) is inserted through that nick in the skin, into the fatty layer. That cannula is used to inject a buffered saline or similar aqueous solution into the fat, to help liquefy the fat. This increases the quantity of fat (and the number of viable stromal cells) that can be extracted from a relatively small region beneath the skin. The aqueous liquid emerges from holes in the side of the cannula, near the tip, and by using a combination of liquid injection and cannular motion, the physician can create, in a relatively brief time, a region of liquefied fatty tissue that is ready for extraction.

When that point is reached, the injection cannula is withdrawn, and an extraction cannula is inserted in its place. To minimize any risk of unwanted complications or damage to tissue in the surrounding region, most surgeons operate an extraction cannula solely by using their hands to exert tension on the plunger handle, within an extraction syringe, without using a pump or other machine to create an artificial suction. By closely watching the flow of viscous fluid into the clear-walled barrel of a syringe while sustaining a continuous and reliable "feel" (through their hands) for what the cannula is doing beneath the skin, a skilled surgeon can develop a reliable sense of how to extract a substantial volume of fluid in the safest possible manner, with minimal scarring, tissue disruption, or unwanted alterations or deformation of the skin surface contour in the affected region.

The only mechanical device which a surgeon typically uses, to help sustain a continuous and relatively stable level of suction force on the extraction cannula, is a clip-type device commonly called a "JOHNNIE-LOK" (that phrase apparently is used as a trademark, by a company called Tulip, but a search of the US trademark database indicates that any registration for that mark died in 2002). By means of a simple twisting motion, this type of clip (which rests and presses directly against the syringe opening) can be used to temporarily secure the plunger handle to the syringe barrel, at any position along the length of the plunger handle. Accordingly, a surgeon can pull out the plunger handle until a desired level of suction force is reached, and then use the "Johnnie-Lok" clip to sustain that level of suction, for some period of time, while the surgeon focuses on the movement, positioning, and "feel" of the cannula tip beneath the skin. When enough fluid has entered the syringe barrel to cause the suction force to drop to an undesirably low level, the surgeon twists the plunger handle to release it from the "Johnnie-Lok", pulls the plunger farther out of the syringe barrel to re-establish a desired and effective level of suction, and then clips the plunger handle to the syringe at the new position.

This suction process continues until the syringe is nearly filled with liquid. At that point, the full (or loaded, etc.) syringe is removed, and a new and empty syringe is put in its place, to extract more fluid. This replacement can be done in either of two ways: (i) by detaching a full syringe from the extraction cannula while leaving the cannula in place, in the patient's body; or, (ii) by pulling out the cannula, and replacing it (this is often done is a surgeon suspects one or more of the holes in the cannula have become clogged).

As many syringes are used as are necessary to remove a quantity of liquefied fatty tissue that the surgeon believes to be useful and desired for a particular procedure on a particular patient. These volumes are important, and they are discussed in more detail below, because they factor heavily into the specific teachings and claims of this invention.

Returning to background information which can help explain how this invention works, fatty tissue is a complex mixture which consists mainly of four types of material:
(1) collagen, an extra-cellular fibrous protein which forms a three-dimensional "matrix" or "scaffold" which holds the cells together in essentially all connective tissues;
(2) large numbers of living cells, most of which will be attached or "anchored" to the extra-cellular collagen matrix;
(3) aqueous fluid, which comes from two main sources: (i) the saline solution or other artificial fluid that was injected into the extraction site, to help liquefy the fatty tissue; and, (ii) the naturally-occurring aqueous fluids that are present even in fatty tissue, mainly in the form of lymph and "tissue gel", both of which help nutrients reach and permeate into cells, and help carbon dioxide and other wastes diffuse away from the cells; and,
(4) a compound called "glycogen", which is a polymerized fatty compound used by mammals for energy and food storage. As described in any textbook on physiology, glycogen is created by "stringing together" molecules of glucose (a specific 6-carbon sugar, which can be readily and rapidly metabolized by all mammalian cells). When additional energy supplies are needed, the body can begin cleaving off individual glucose molecules, one at a time, from strands of glycogen. Each molecule of glucose can then be metabolized by the process called "glycolysis", in which glucose molecules are "burned" as a fuel source, in a manner which oxidizes the glucose into carbon dioxide and water, and which releases energy during the oxidation process.

Accordingly, when fatty tissue is converted into liquefied form (with the aid of injected saline solution or similar liquid), for extraction by a cannula, collagen fibers must be broken, and a relatively thick and viscous mixture is removed, which contains still-living and viable cells.

There are two main types of uses for that type of fatty tissue, after it has been extracted. One is for breast augmentation, in which careful placement of volume and bulk is the most important factor for achieving a desired cosmetic effect. The cell-concentrating procedures and implantation methods described herein can be adapted for such use, if desired (especially for use in reconstructive surgery after a lumpectomy or breast removal, in a patient suffering from breast cancer, which does indeed involve "connective tissue repair" as that term is used herein). Either of those types of surgery (i.e., breast enlargement for purely cosmetic purposes, or breast reconstruction following tumor removal) are specialized types of surgery; they are well-known to cosmetic surgeons, and they can be carried out by surgeons who specialize in that type of surgery, using methods and cell preparations as disclosed herein, if desired. However, that type of cosmetic surgery is not of primary interest herein.

Although that type of cosmetic surgery can adapt and utilize the procedures and equipment described herein, the primary and central focus of these types of treatments will involve connective tissue repairs, as listed and summarized above. Accordingly, the discussion herein focuses on those types of uses.

Before the details of the invention herein are disclosed, one other type of concentrated cell preparation, which was developed years ago and which is well-known and widely used, merits attention.

Combining Stromal Precursor Cells with "Platelet Rich Plasma"

It was discovered years ago (e.g., Abuzebi et al 2001) that the use of stromal precursor cells, obtained from fatty tissues, will generate better results in connective tissue repairs, if the stromal cells are mixed or otherwise co-administered simultaneously with a blood-derived preparation called "platelet rich plasma" (PRP). Machinery and equipment (including "kits" with all necessary disposable devices and supplies) for creating PRP, from a patient's blood, are readily available to physicians, as relatively small "desktop" devices that are roughly the size of a typical microwave oven in a home. Accordingly, this aspect of the invention is old and known, and this section merely provides an overview of platelet-rich plasma preparations from blood.

Platelets are specialized blood cells, which can be obtained from circulating blood. In mammals, they are heavily involved in the natural healing processes which arise in response to any type of injury. Accordingly, they were recognized by at least the 1980's as a rich and available source of: (i) growth factors, including hormones that will trigger cell reproduction; (ii) proteins that can recognize and bind to the "torn ends" of collagen fibers, at the site or a wound or other injury; and, (iii) other biomolecules which can help promote and accelerate healing.

Briefly, when "whole blood" is processed ("fractionated") in a centrifuge, at an appropriate speed which will not damage or kill blood cells (often expressed as a multiple of "gravity" force, such as 40 g, which is commonly used in blood fractionation), three main layers will form.

The "bottom" layer will contain red blood cells (RBC's, also known as erythrocytes), since RBC's have the highest weight-per-volume density of any of the blood components. Red blood cells do not contain any chromosomes; they are formed by a rapid process of cell "budding", rather than cell replication, and they last for only a few days after they are created. Since their sole functions are to deliver oxygen and remove wastes, which require active circulation of blood, they would only clutter and clog up an injured area which has been packed with a stationary stromal-and-platelet cell mixture, for connective tissue repair as described herein. Therefore, the red blood cells are discarded, when a PRP mixture is being created for use in wound healing.

Above the bottom layer of red blood cells, a center layer will form, which mainly contains platelet cells, and white blood cells (leukocytes).

The uppermost layer, which is relatively clear but with a yellowish tint, contains the carrier liquid, which is blood plasma. If blood plasma is further processed to remove fibrinogen and other clotting factors (which are extra-cellular proteins), the resulting liquid is called blood serum.

In a broad sense, any blood preparation in which the platelet concentration has been enriched above a "baseline" level (as found in unprocessed "whole blood") can be referred to as "platelet rich plasma" (PRP). However, in order to render PRP truly effective for accelerating and enhancing wound-healing activity, the concentration of platelets preferably should be increased to at least about 5 times (5×) their "baseline" level.

After an initial centrifugation step has been used to remove red blood cells from a processed blood fraction, other processing steps (including various types of filtration, gel processing, "affinity binding", or chromatographic steps, and possibly involving the addition of various other agents) can be used, if desired. Depending on the specific steps that are used, this type of additional processing can, for example: (i) remove other types of white blood cells from a concentrated platelet preparation; (ii) remove one or more specific targeted proteins (such as growth factors, albumin, etc.) or other molecules; (iii) remove a portion or fraction of the plasma liquid, from the platelets, to further increase platelet density and concentration levels; or (iv) add various supplemental agents to a PRP preparation.

These types of processing steps, which can be used to create PRP mixtures for use in wound-healing procedures, are described in numerous review articles, including Pietrzak et al 2005, Maniscalco et al 2008, Hall et al 2009, Gociman et al 2009, Lacci et al 2010, and Lopez-Vidriero et al 2010.

Various companies sell processing machines that are specifically designed to extract PRP, from whole blood. A preferred system which has been used with good results by the Applicant herein is the SmartPReP™ Platelet Concentrate System, sold by Harvest Technologies. It is illustrated and described at www.harvesttech.com and in additional sources which can be identified and obtained from that website. That system generates a PRP extract with high numbers of platelets and monocytes, which are beneficial for the types of treatments described herein, and with reduced numbers of other white blood cell types (including granulocytes, which are not especially beneficial for connective tissue repairs as disclosed herein).

Other companies also make machines which can generate PRP extracts from whole blood; one example is the MAGELLAN™ system, sold by the Arteriocyte Company (http://arteriocyte.com).

Both types of machines were introduced into the marketplace in the U.S. in 2009, and those two companies are competing against each other to create superior machines. Accordingly, various enhancements in such machines have further optimized PRP extraction methodology, and likely will continue to do so.

In summary, methods which utilize mixtures and combinations of:
  (1) stromal precursor cells, obtained from fatty tissue via liposuction; and,
  (2) platelet cells, obtained and concentrated from blood samples,
  have been known and in use for more than a decade, for connective tissue repairs. These methods have established an important specialty within the field of medicine and surgery, and the current invention involves methods and devices which can enhance and improve those surgical and medical interventions and procedures.

Accordingly, one object of this invention is to disclose and provide methods and devices that can help achieve greater efficiency and better results, when stromal (connective tissue) precursor cells are obtained from fatty tissue, via liposuction, for autologous transplantation into the same patient, for connective tissue repairs.

Another object of this invention is to disclose and provide certain types of specialized devices, which include both reusable and disposable components that will interact with each other, which will enable improved methods of centrifugation and other processing steps, for handling and concentrating stromal precursor cells which will be used for autologous transplantation.

Another object of this invention is to disclose methods and devices for carrying out a process of concentrating and enriching autologous cells that have been harvested from fatty tissue extracted from a patient via liposuction, which will minimize any loss of viable stromal precursor cells from the fatty tissue extract.

Another object of this invention is to disclose methods and devices for concentrating stromal precursor cells that have been harvested from a patient, which involve mechanical rather than enzymatic or other biochemical processing, and: (i) which can be completed quickly, such as within 20 minutes or less, rather than requiring a sustained incubation or reaction period to complete an enzymatic treatment; and, (ii) which minimize or eliminate the types of governmental scrutiny and approval requirements that come into play when chemical treatments are performed on cells which will then be permanently implanted in a patient's body.

These and other objects of the invention will become more apparent from the following summary, drawings, and detailed description.

SUMMARY OF THE INVENTION

Methods and devices are disclosed for processing stromal precursor cells (i.e., cells which can differentiate into various types of connective tissue cells, such as cells in muscles, ligaments, tendons, etc.), which can be obtained in large numbers from fatty tissue extracts, obtained via liposuction. These types of cells, either by themselves or when combined with a second cellular mixture called "platelet-rich plasma" (PRP), can be used for autologous cell transplantations, to repair, regenerate, or supplement connective tissue, at an injury site or other location that is in need of repair or other medical intervention.

Processing of a fatty tissue extract involves centrifugation during an initial separation step, to concentrate stromal precursor cells from liposuction fluid into a semi-concentrated form that is usually called "spun fat" in the prior art.

The "spun fat" should then be treated by a second stage of processing, as disclosed herein, to further concentrate the stromal precursor cells while eliminating glycogen, fat, and remnants of the extra-cellular collagenous matrix. In one embodiment, the cell suspension can be incubated with collagenase, an enzyme, to break down and remove the extra-cellular collagen fibers that will be present in the initial fatty extract. However, an alternate embodiment is strongly preferred over collagenase treatment, for reasons described below. In the preferred process, mechanical means (such as mildly forcing the "spun fat" cell suspension through an extrusion device) can be used to detach stromal precursor cells from the extra-cellular collagen matrix. A second centrifugation and/or filtration step can then be used to further concentrate the stromal precursor cells that have been released from the fatty matrix of the spun fat material.

By means of these processing steps, stromal precursor cells from a fatty liposuction extract can be converted into a highly concentrated form, for subsequent reintroduction (along with platelet-rich plasma, if desired) into a wound site or similar area that is in need of tissue repair.

In addition to disclosing those type of enzymatic and/or mechanical methods for extracting concentrated stromal cell preparations from liposuction extracts, specialized centrifugation cartridges are disclosed herein, which will enable up to 120 cubic centimeters (cc) of fluidized liposuction extract, in six syringes which will hold 20 cc each, to be processed in a single centrifugation step, using the same centrifuge machine that is also used to prepare platelet-rich plasma (PRP). To accomplish that, each 20 cc syringe must be short enough to fit into an accommodating centrifugation cartridge which will contain three wells, to hold up to three syringes at a time. These types of centrifuges hold two cartridges at a time, at opposite ends of a rotor, for proper balance during high speed centrifugation. Accordingly, a set of two cartridges, holding three syringes each, will hold six syringes, containing up to 120 cc of liposuction extract with stromal precursor cells. It has been found that 120 cc of fatty tissue extract is sufficient to satisfactorily handle the very large majority of such procedures, even in cases where a patient will require a series of multiple cell injection procedures over a span of multiple months.

Furthermore, the new types of centrifugation cartridges disclosed here also can be provided with a lipophilic absorbent material insert, which will withdraw and sequester the liquefied oils which are contained in a "spun fat" preparation. It has been found by the Applicant herein that those liquefied oils become toxic to stromal precursor cells, when the oils become concentrated to the point that occurs in spun fat. Therefore, a component or process which removes those oils from sustained contact with the cells will help increase the health and viability of the cells that can be returned to a patient's body.

Accordingly, improved methods and devices are disclosed herein, for rapid and convenient preparation of highly purified stromal precursor cells, for use in connective tissue repairs. In addition, an improved combination of centrifuge cartridges and liposuction syringes are disclosed herein, to provide a single set of devices that will enable convenient and efficient handling of up to 120 cc of liposuction extract at a time, using the same centrifuge machine which is used to prepare platelet-rich plasma.

Figure 1:
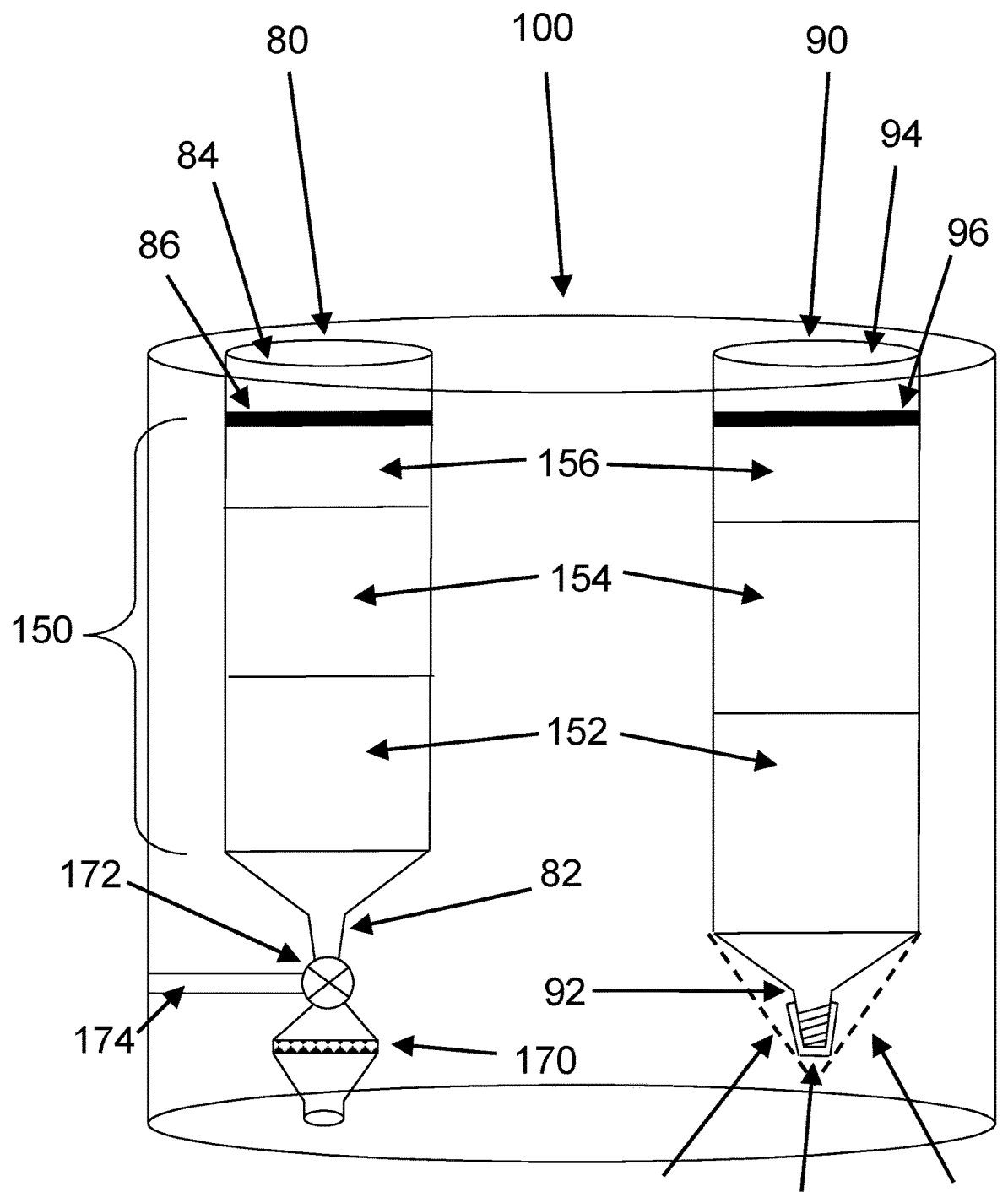
FIG. 1 (which is prior art) depicts of the layers that will be formed, when a liquefied fatty tissue extract, obtained from a patient via liposuction, is centrifuged for a suitable period of time at a speed that will not damage viable cells. This drawing shows two identical syringes, each containing approximately 20 milliliters (mL or ml) of a fluidized liposuction extract which has been centrifuged; both syringes are held within accommodating wells, in a cartridge designed for use in a centrifuge machine. The uppermost oily layer (with the lowest density) will be discarded. The center layer, referred to herein as "spun fat" for convenience (and as "concentrated fatty tissue extract" in the claims) will contain a semi-concentrated suspension of stromal precursor cells (which can also be called connective tissue precursor or progenitor cells). The bottom layer, which has the greatest weight-per-volume density, will contain mostly water, but it will also contain substantial numbers of stromal precursor cells; therefore, that watery layer will be forced, using gentle pressure and/or suction, through a filter which does not allow cells to pass through. This will retain the stromal precursor cells on the surface of the filter; they can then be washed off of the filter surface, and mixed with cells in the "spun fat" layer, for additional processing.

For comparative and descriptive purposes, the syringes on the left side of FIG. 1 is shown in a well that has a valve-controlled flow conduit which leads to a filtering device. The syringe on the right side is shown with a simple "cap" screwed to its tip. The first arrangement is feasible; however, the second arrangement is generally preferred, since it allows the syringe to be simply removed from the centrifuge device and then handled conveniently.

Figure 2:
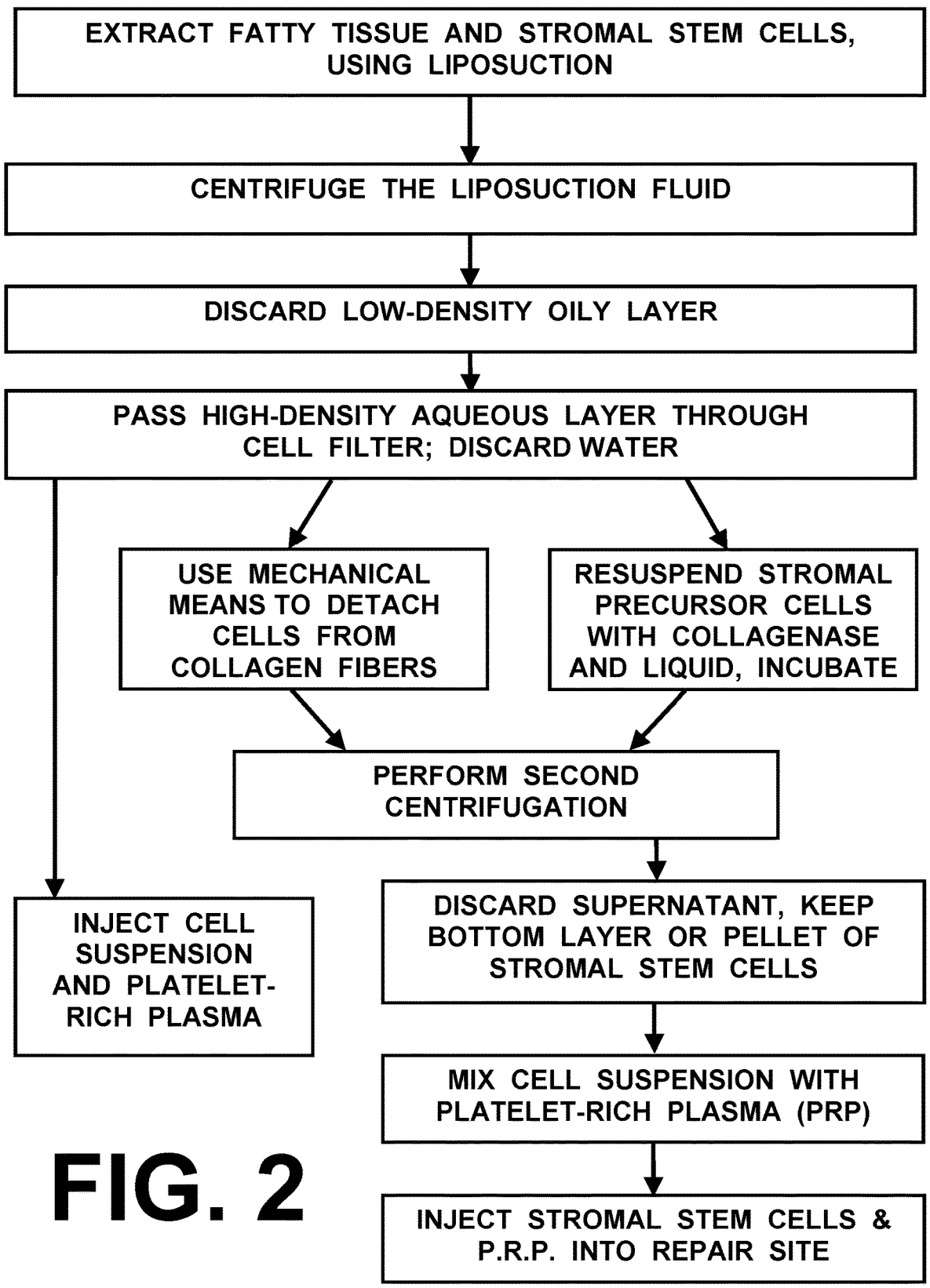

FIG. 2 is a flow chart depicting a series of steps that can be used to process, extract, and utilize stromal precursor cells contained in a liposuction extract from a patient who requires connective tissue repair.

Figure 3:
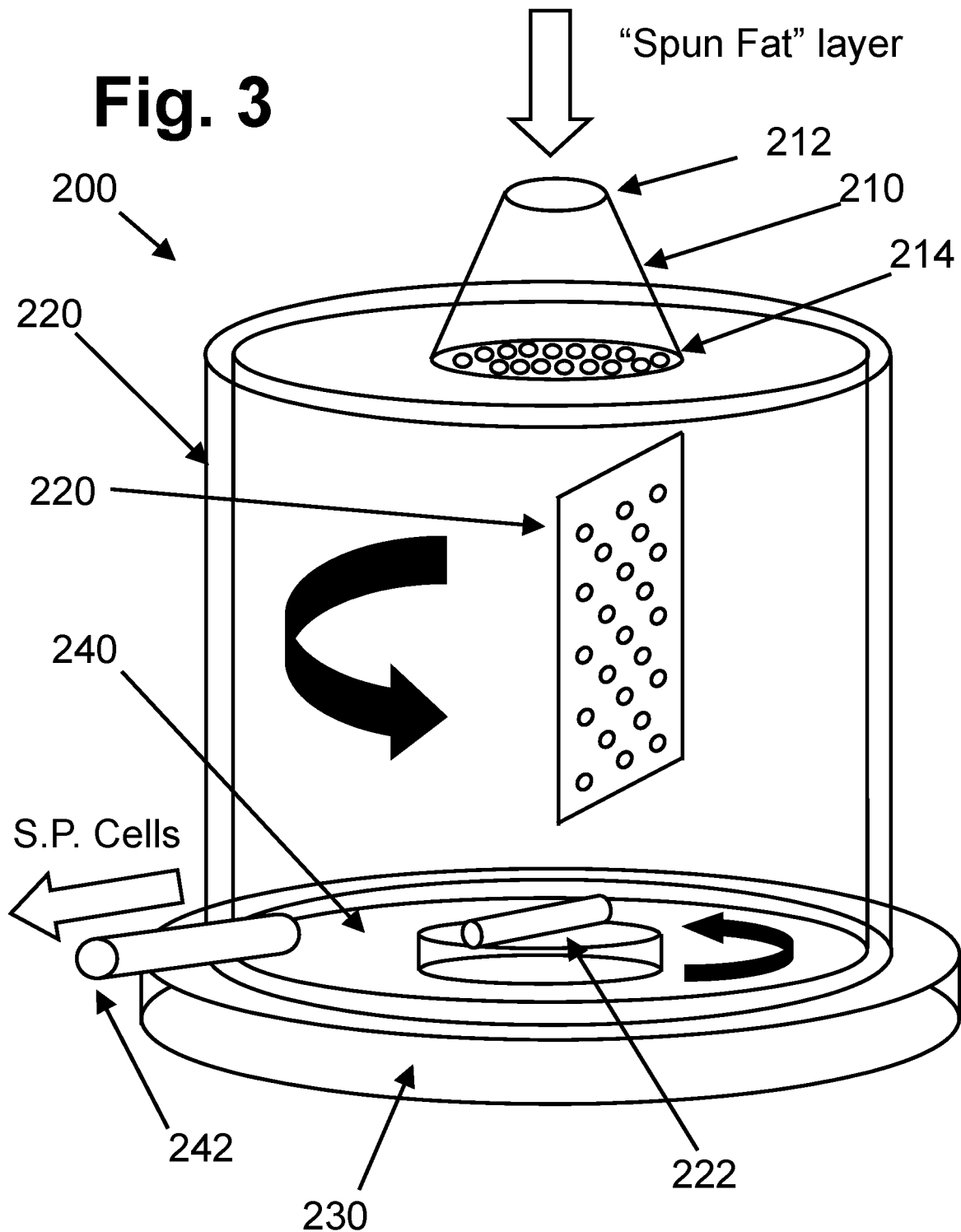

FIG. 3 is a schematic depiction of a device for mechanically separating stromal precursor cells from fat and collagen fibers, in a "spun fat" suspension created by: (i) initial centrifugation of a liposuction extract, followed by (ii) mixing the spun fat material with a saline buffer containing a gentle surfactant, such as lecithin. A piston or plunger is used to force the cell suspension downward, through an extrusion plate having multiple small tapered orifices passing through it. This will partially break apart the spun fat layer, in a manner that will begin releasing the stromal precursor cells from the fat and collagen matrix. The mixture of water, fat, and cells is circulated and rotated, with the aid of a mechanical stirring device, around a cylindrical chamber having several perforated "catch plates" (for simplicity, only one such catch plate is shown in FIG. 3). Fatty and oily droplets in the aqueous suspension will impinge against and cling to the catch plates, while the stromal precursor cells will drop out of solution and accumulate on a sloped floor of the cylinder, for removal via an outlet.

Figure 4:
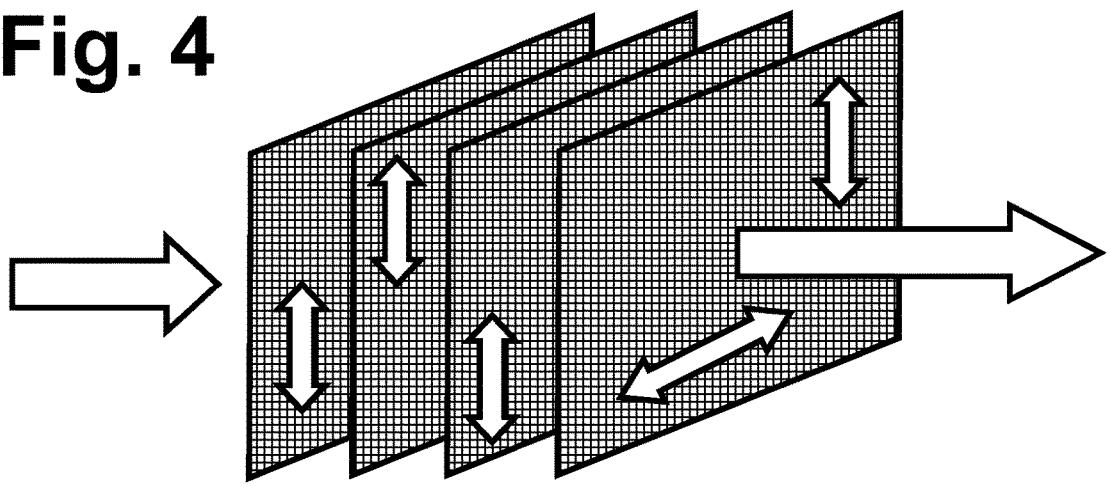

FIG. 4 is a schematic depiction of a "screen passaging" system which can use vibrating, reciprocating, or tapped screens, to mechanically separate viable cells from the fat and collagen matrix in a "spun fat" suspension created by centrifuging a liposuction extract.

Figure 5:
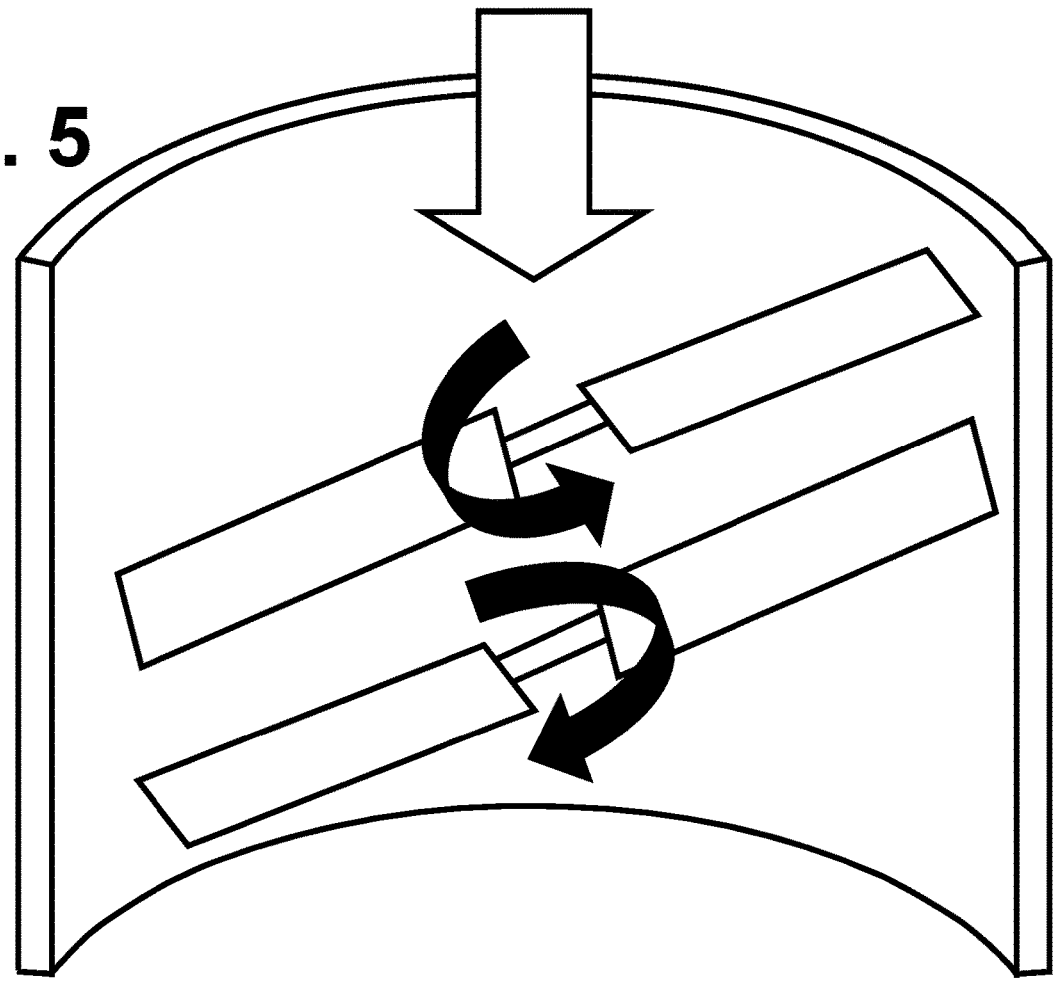

FIG. 5 is a schematic depiction of a "shearing-force stirring" system to mechanically separate viable cells from the fat and collagen matrix in a "spun fat" suspension created by centrifuging a liposuction extract.

Figure 6:
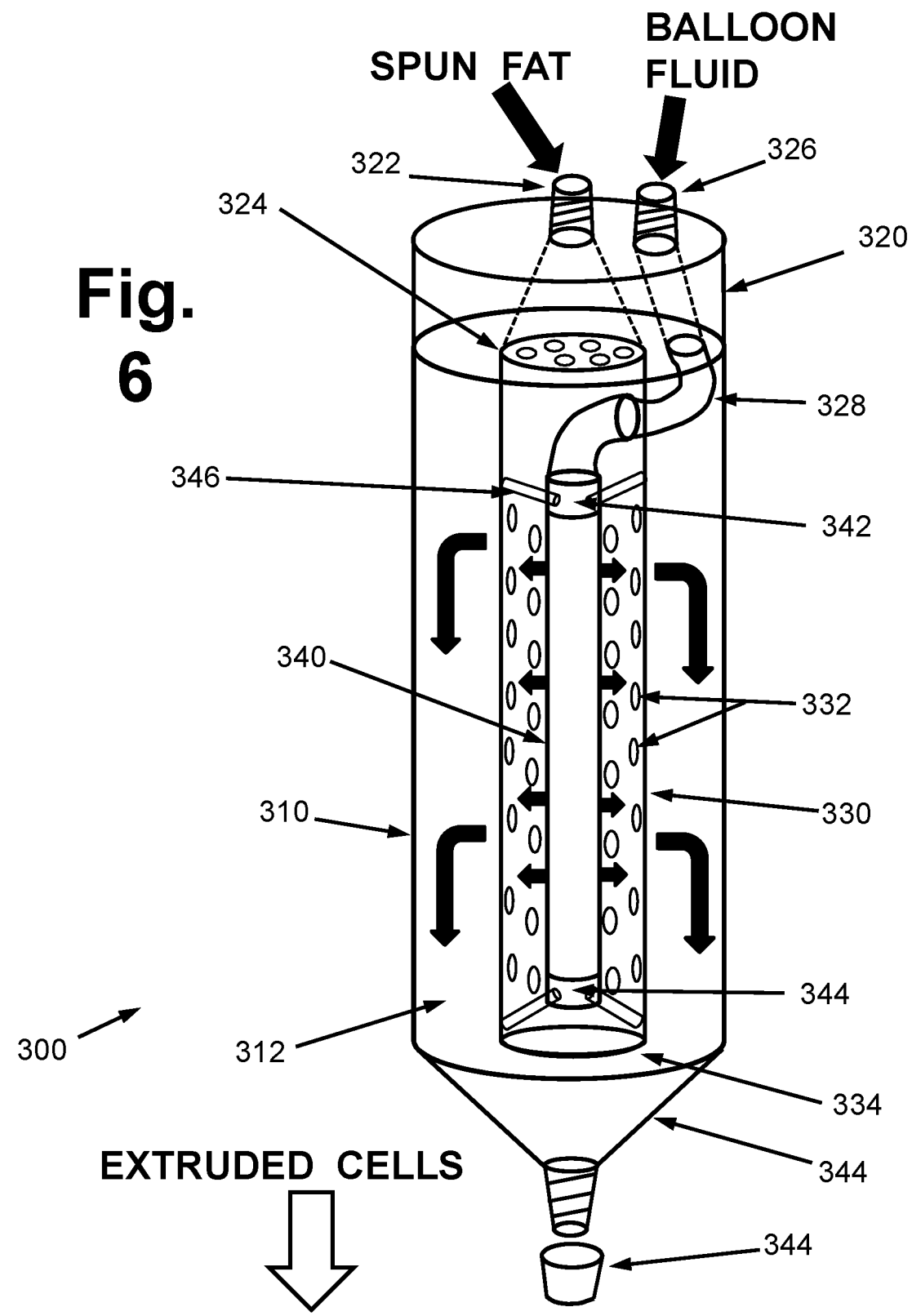

FIG. 6 is a schematic depiction of an "extruding and centrifuging" device which can fit inside a centrifuge machine, and which uses a displacing device comparable to an inflatable balloon catheter, to gently force the "spun fat" preparation through small holes which pass through a cylindrical wall, to reach an annular collection space, thereby gently prying stromal precursor cells away from collagen fibers and extra-cellular debris, so that the cells can be separated by a centrifugation step using the same extruding device.

Figure 7:
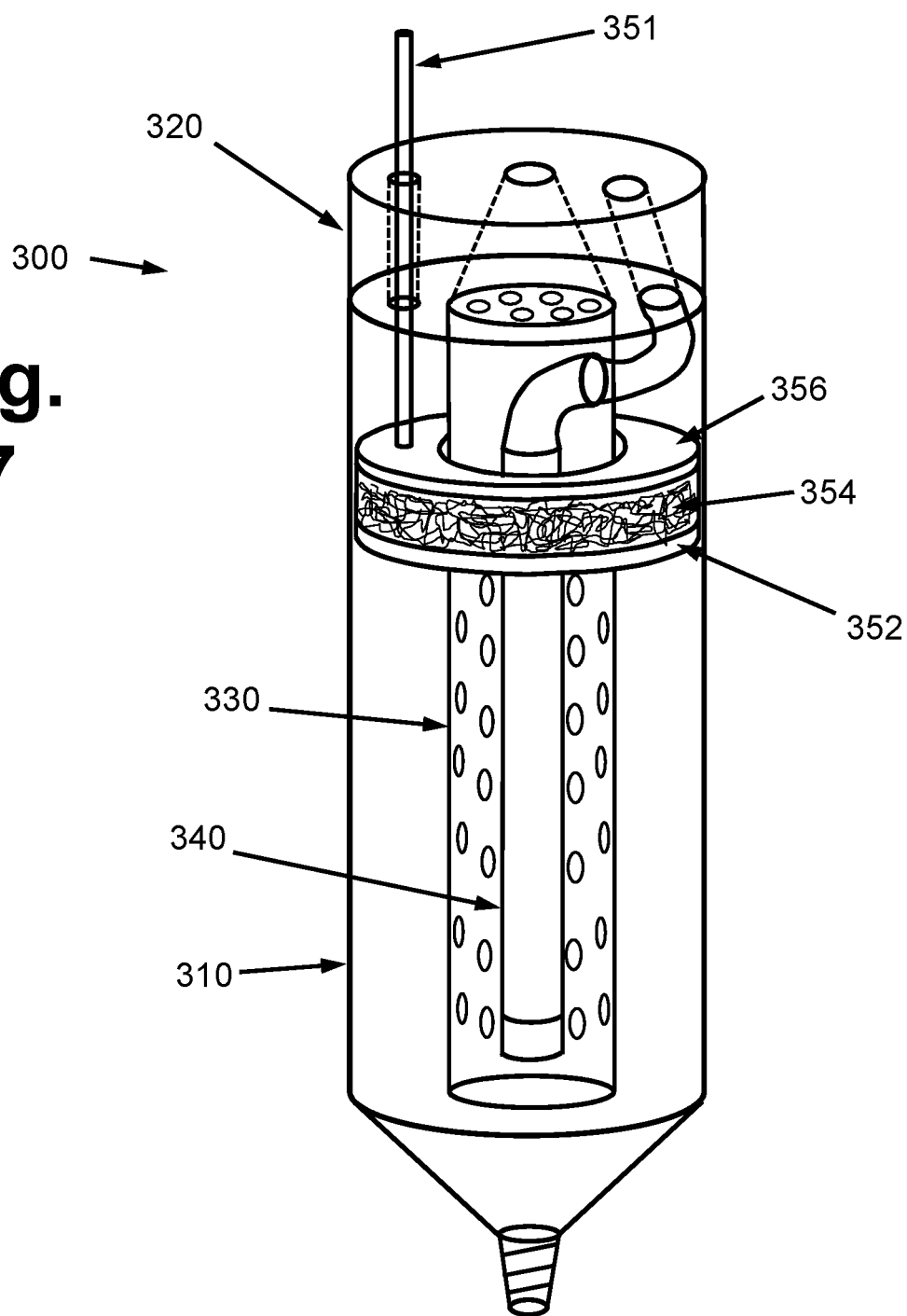

FIG. 7 is a schematic depiction of the same device shown in FIG. 6, also showing an oil removal component which can extract and sequester liquefied oils that will emerge from the "spun fat" material, so that those oils will not remain in sustained contact with the stromal precursor cells, which would damage the cells by clogging and fouling their surface receptors.

Figure 8:
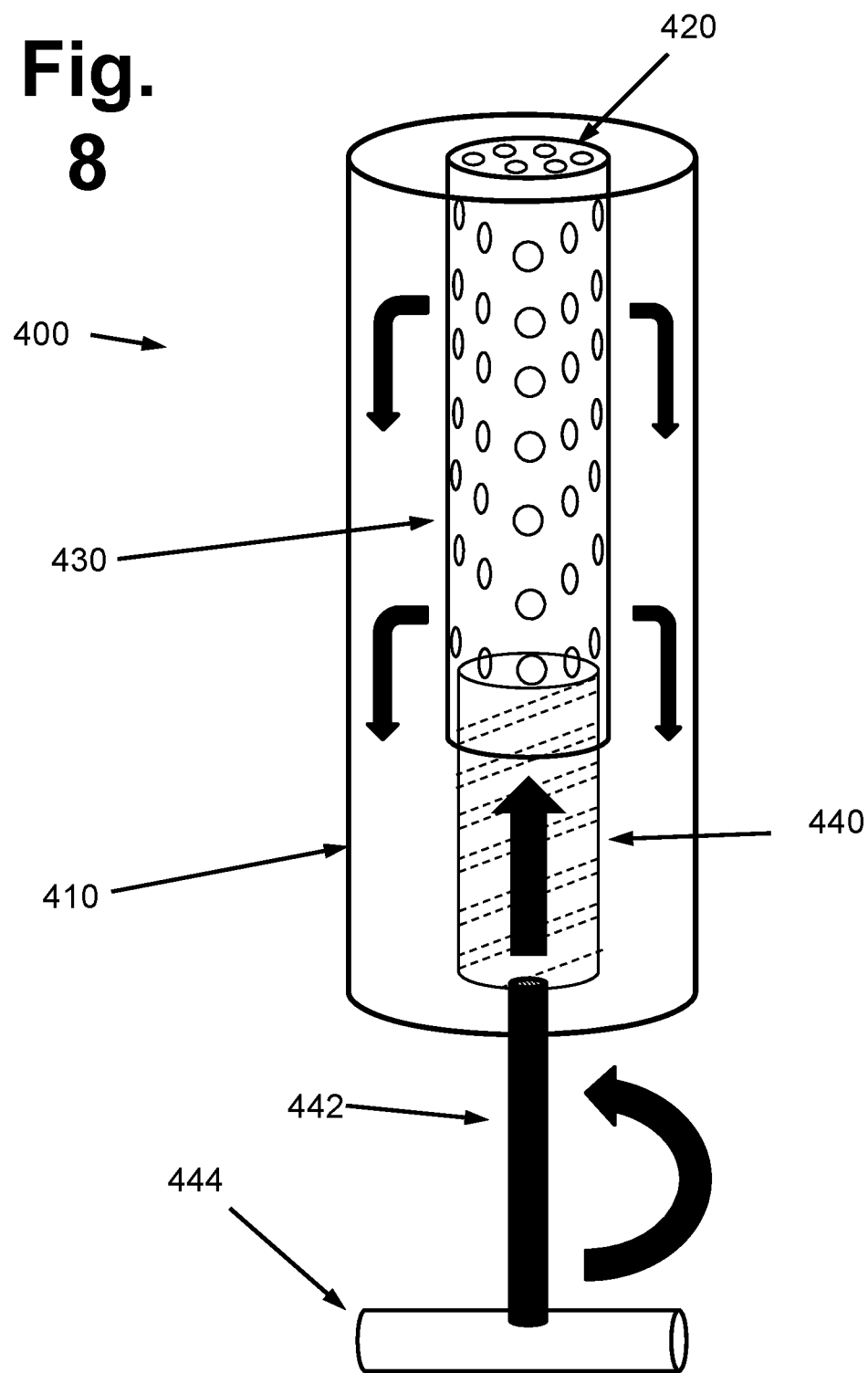

FIG. 8 is a schematic depiction of an "extruding and centrifuging" device which uses a large rotatable threaded shaft to displace and force spun fat through an extrusion tube.

Figure 9:
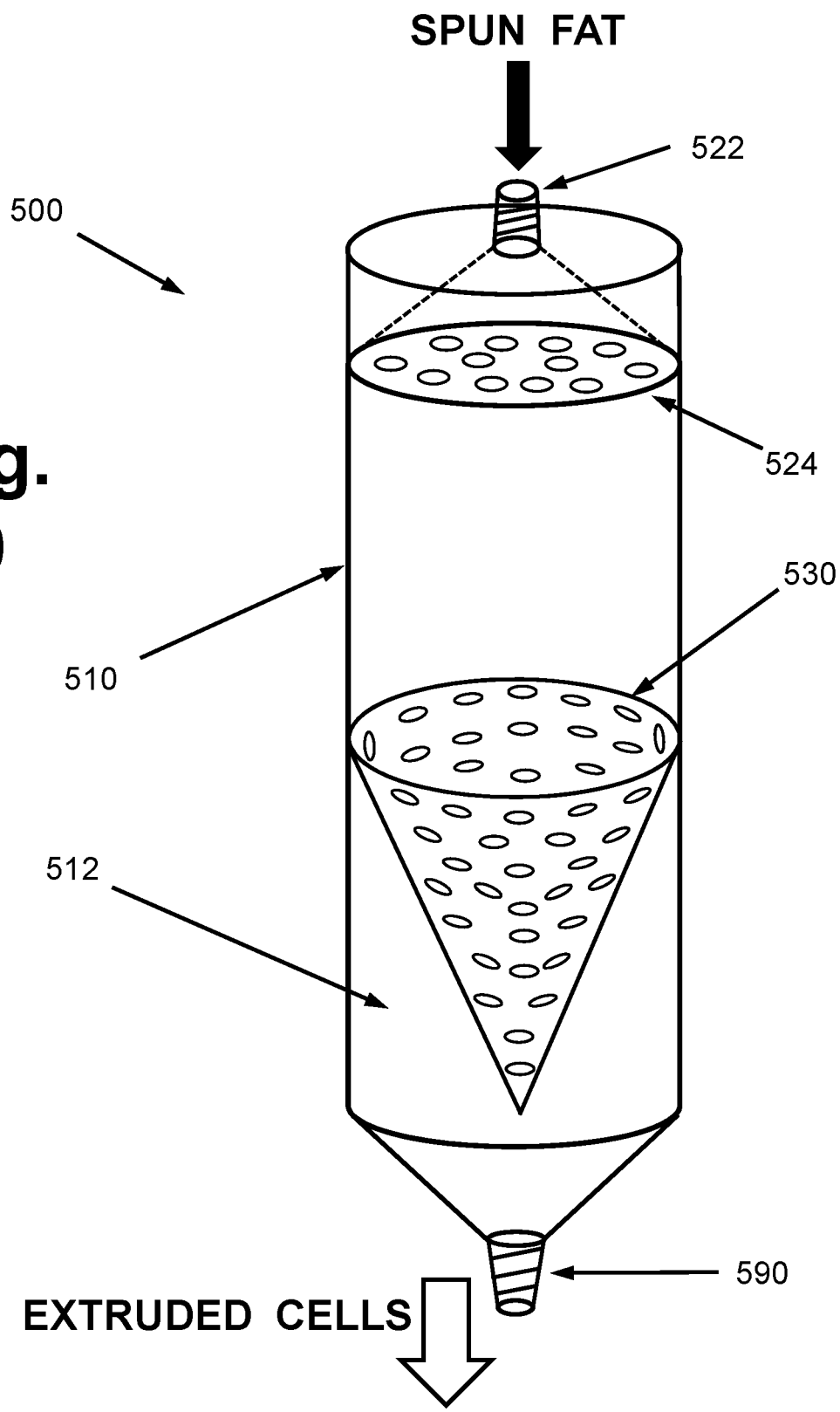

FIG. 9 is a schematic depiction of an "extruding and centrifuging" device which uses centrifugal force to drive spun fat through a cone-shaped extruder.

Figure 10:
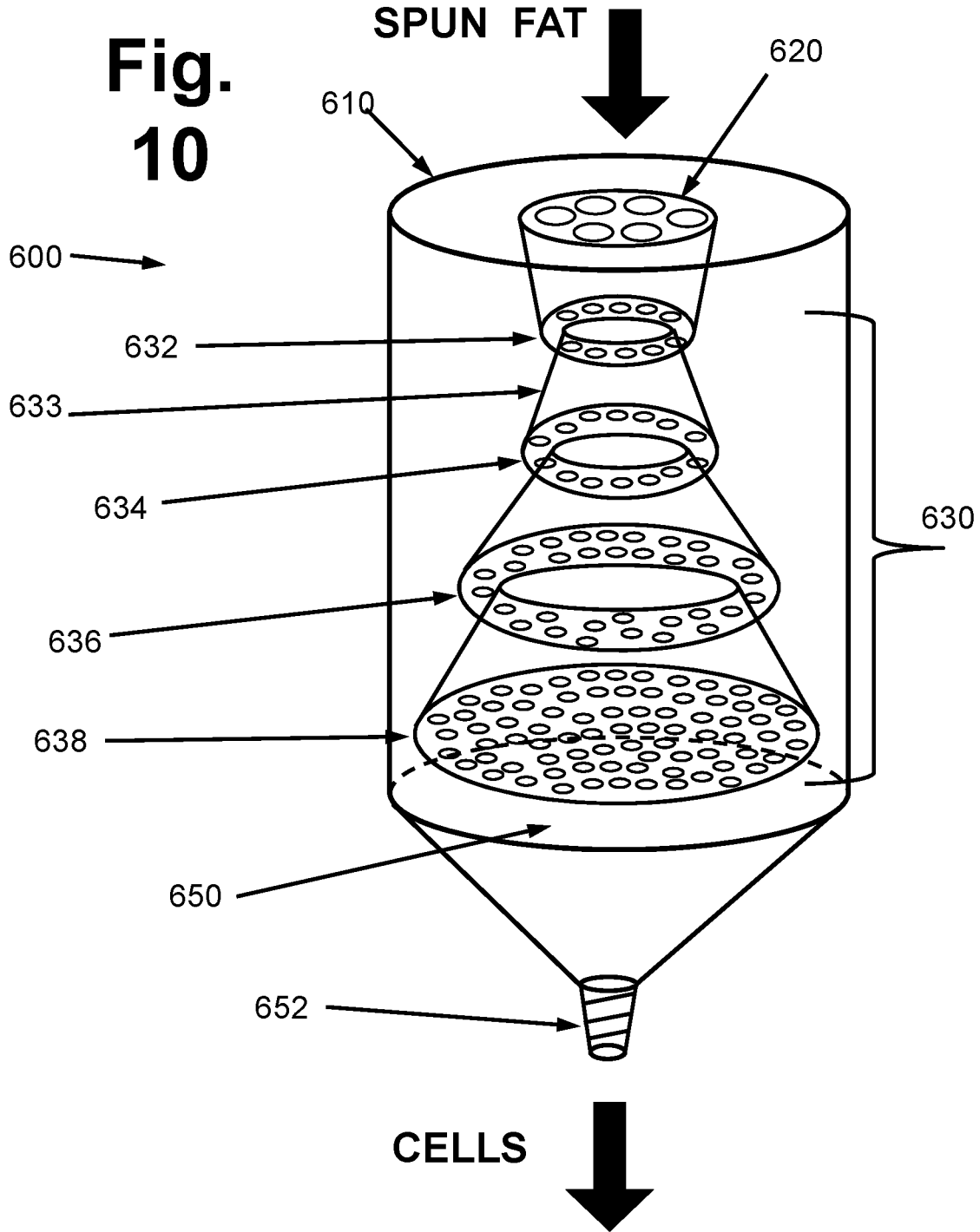

FIG. 10 is a schematic depiction of an "extruding and centrifuging" device which uses centrifugal force to drive spun fat through an entire set of annular and planar extrusion surfaces.

Figure 11:
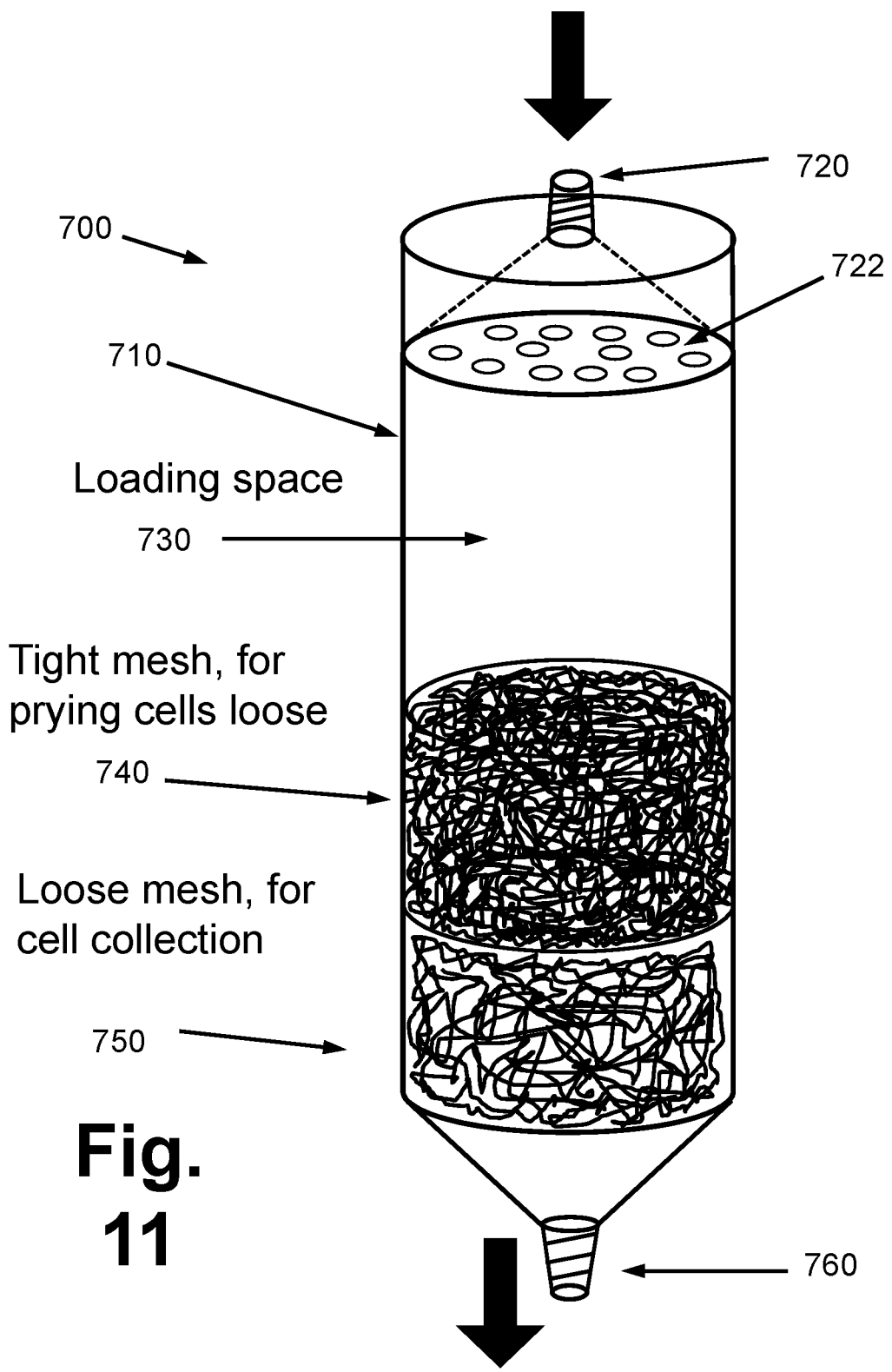

FIG. 11 is a schematic depiction of an "extruding and centrifuging" device which uses centrifugal force to drive spun fat through a dual-mesh system, to separate stromal precursor cells from extra-cellular material.

Figure 12:
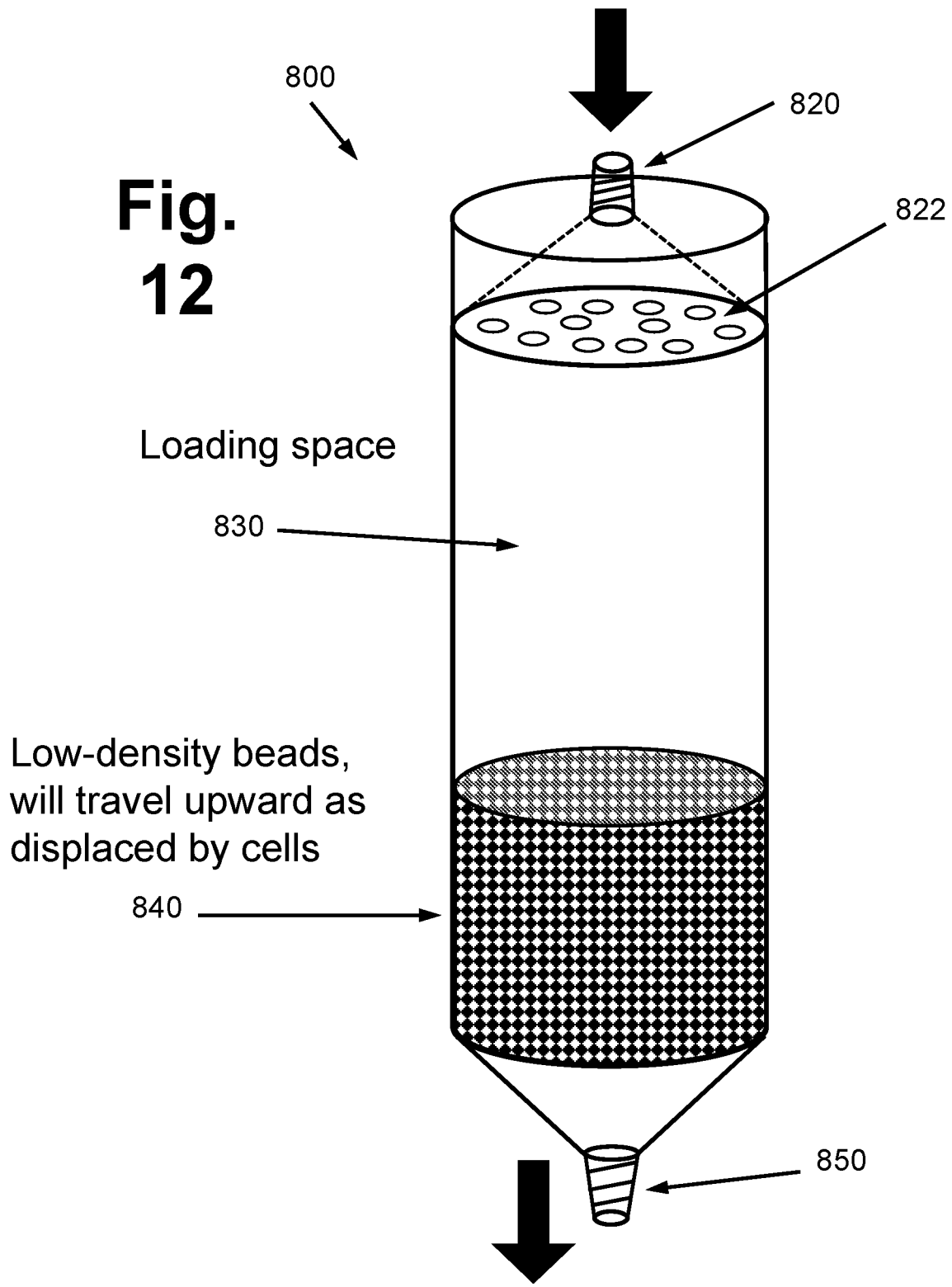

FIG. 12 is a schematic depiction of an "extruding and centrifuging" device which uses centrifugal force to drive spun fat through a layer of lightweight beads, so that the jostling activity, as heavier cells swap positions with lighter beads, can help separate stromal precursor cells from extracellular material.

Figure 13:
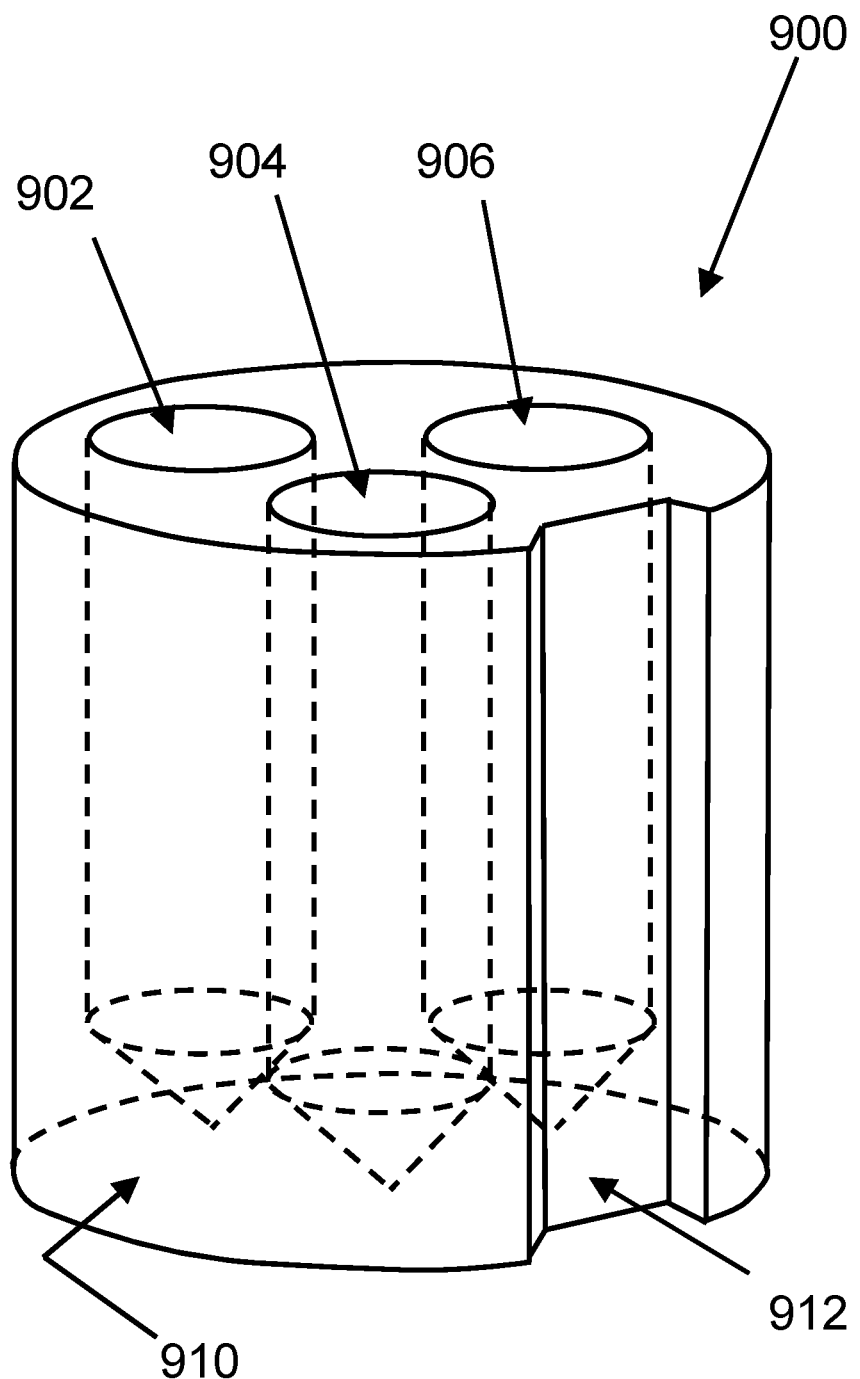

FIG. 13 is a perspective view which depicts a centrifugation cartridge that can hold three syringes, with each syringe holding up to 20 cc in volume. This centrifugation cartridge is sized and designed to fit into a commercially available centrifuge machine that is designed and suited for preparing platelet-rich plasma (PRP) from whole blood.

Figure 14:
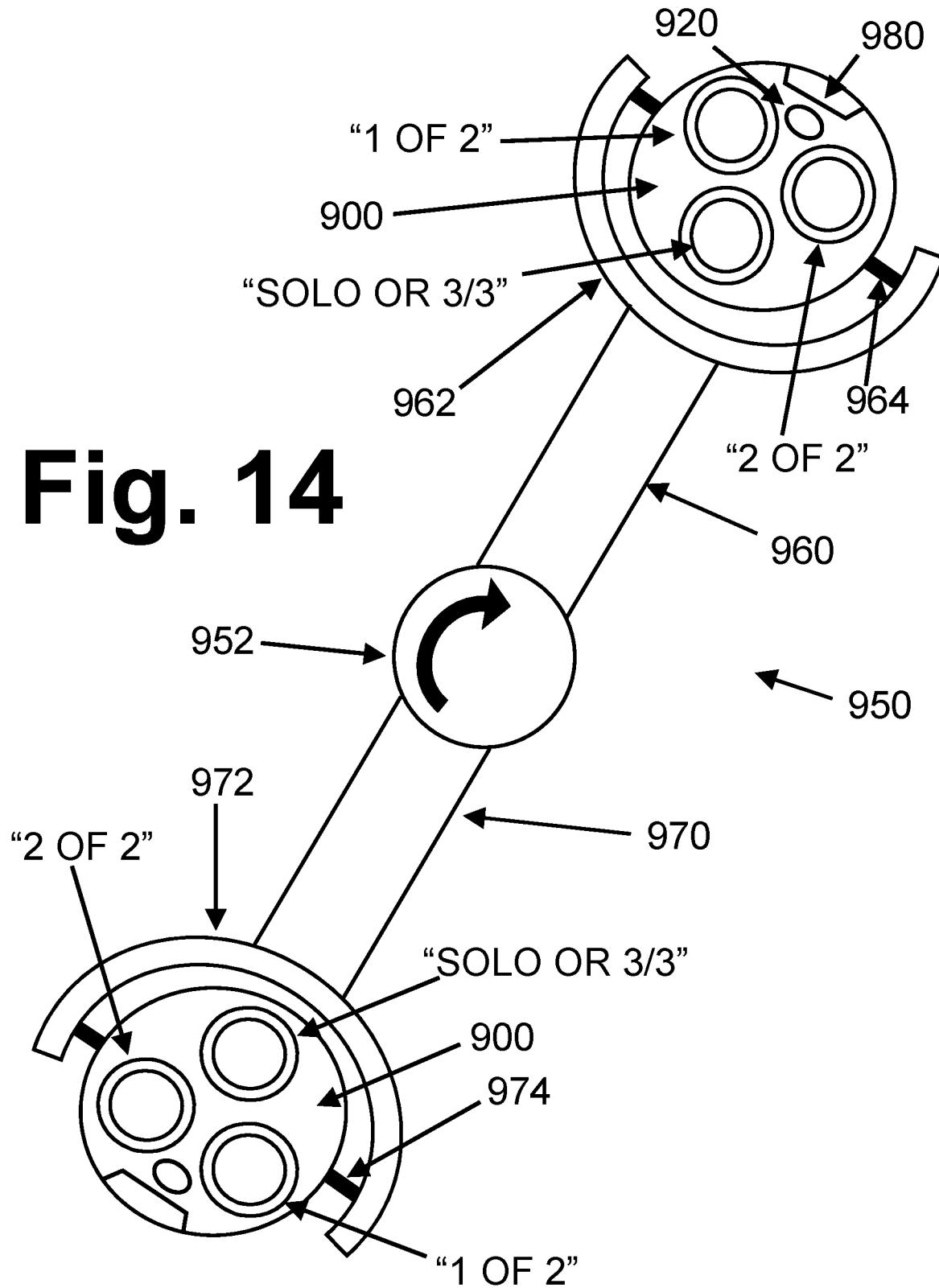

FIG. 14 is an elevation (plan) view of two centrifugation cartridges, each having three wells for syringes that can contain 20 cc each of liposuction fluid. Each cartridge is held within a basket device at one end of a rotor, in a centrifuge. The wells in the cartridge are labeled, to indicate a loading sequence that will maintain balance and symmetry regardless of whether two, four, or six syringes are loaded into the centrifuge. A small additional well is also included in each cartridge, which can hold water or any other liquid or weight, to evenly balance the weights of two cartridges (including any loaded syringes held by the cartridges) against each other.

DETAILED DESCRIPTION

As summarized above, this invention relates to improved devices for processing and concentrating stromal precursor cells (i.e., cells which can mature into connective tissues, such as muscles, tendons, and ligaments). Those types of cells can be obtained from fatty tissues in a patient's body, by means of liposuction. If processed properly, those types of precursor cells can be extremely useful and helpful in treatments for various types of tissue defects, including but not limited to treatments for injuries, infections, arthritic or similar degeneration, for scar revision, or for other problems that are associated with joints, limbs, or other connective tissues.

If desired, stromal precursor cell preparations as described herein can be mixed with concentrated preparations of specialized blood cells called "platelets", such as in a liquefied preparation called "platelet-rich plasma" (PRP), which is well-known in this field of art. When a concentrated preparation of stromal precursor cells is mixed with platelets (which specialize in promoting tissue repair, and the mixture is injected into an injury or infection site, the result can be comparable to having both: (i) a set of skilled carpenters (which are analogous to the platelet cells), and (ii) a supply of building materials (which are analogous to the stromal precursor cells), at a job site where something needs to be built.

Conventional liposuction procedures, which have been used with good results by the Applicant herein to obtain supplies of stromal precursor cells from patients, are described in Example 1. However, this invention does not depend upon, arise from, or claim any specific procedures or details relating to any process or method used to extract fatty tissue from a patient. When human patients are involved, liposuction (or any other form of adipose tissue extraction) is a form of surgery, and can be performed only by qualified and licensed physicians. Any physician who performs liposuction will have his or her own preferences concerning equipment, methods, and kits with disposable supplies, for performing liposuction.

Various devices and supplies for performing low-volume liposuction (i.e., the type of liposuction procedures that are suited for harvesting stromal precursor cells, as distinct from high-volume liposuction, as used for weight reduction purposes) have been available for years, and are well known to those skilled in this field of surgery. As one example, the VIAFILL™ system, sold by the Lipose Corporation, includes various tools and instruments (generally referred to as "devices" herein, to distinguish them from liquid-type supplies, reagents, pharmaceuticals, etc.) that are specifically designed for low-volume liposuction. Those are described and illustrated at www.viafill.com.

However, there is one factor that requires attention, with regard to the liposuction part of the treatments described herein. This factor relates to the volumes of fatty tissue that should be extracted, for carrying out various different types of treatments.

Liposuction Extraction Volumes

Based on trials and tests on a number of patients (all of whom provided informed consent), which involved treatments for some of the most common types of connective tissue injuries that can benefit from stromal precursor cell transplantations as described herein, the Applicant herein has determined that volumes such as those listed in Table 1 usually are appropriate in most cases of typical pain, discomfort, and damage, when treating an adult male. These volumes will include aqueous fluids that were injected into a patient to help break apart and liquefy the fatty tissue that was being removed, and which was then suctioned out along with the fatty tissue. Accordingly, volumes of actual fatty tissue which are extracted during these procedures, when injected aqueous fluids are not included, are correspondingly lower. Furthermore, when treating cases of severe damage and pain, correspondingly larger volumes should generally be extracted, in anticipation that a series of several injections may be required, over a span of months, to provide better results.

TABLE 1

TYPICAL FLUID EXTRACTION AND PROCESSED CELL VOLUMES

| Type of Treatment | Liposuction Extract (cc) | Processed Stromal Cells (cc) |
| --- | --- | --- |
| Shoulder (rotator cuff) | 30-50 | 3 |
| Elbow (tendonitis) | 30-50 | 3 |
| Hip | 50-80 | 4-6 |
| Knee | 50-80 | 4-6 |
| Ankle | 30-50 | 3 |

Table 1 also indicates the approximate volumes of fully-processed stromal precursor cells which should be obtained via these types of liposuction procedures, when the cells have been fully processed and concentrated, prior to injection back into a patient. These concentrated cell volumes will be contained in a cellular pellet or layer, which will be generated as described below and as indicated in FIG. 2.

If it appears that inadequate numbers of cells are present in the fatty tissue extract from some particular patient, then the treating physician can extract additional fatty tissue, either from the same area that has already been anesthetized, or from a different area of the patient's body (such as (i) if the anesthesia has partially worn off, and/or (ii) if the withdrawal of additional fatty tissue from the initial liposuction site might leave undesirable surface irregularities). If a physician wishes to do so, he or she can check the apparent cell density per volume of fluid, in one or more small samples of fluid taken from the "spun fat" material after the first centrifugation, or from a sample of liquid taken at any stage during subsequent processing. That type of check, for cells-per-volume density, can be performed using a light microscope if desired, or by means of more sophisticated equipment, such as a flow cytometer.

An important factor which must be taken into account, when planning and performing liposuction to obtain a sufficient quantity of stromal precursor cells for any particular treatment, arises from the fact that certain types of injuries can require two or more treatments, at different times, to obtain optimal results. Such repeated treatments normally will involve: (i) a first injection of stromal precursor cells (which can be mixed with PRP if desired), usually on the same day that the liposuction is performed; and, (ii) one or more additional treatments, which typically will occur at least a month or more after the initial treatment.

For example, if a patient requires "bilateral" treatments (i.e., on both sides of the body, such as on both hips, or both knees), a preferred approach usually will involve: (1) treating a first hip or knee, which usually will involve the joint that is causing the most pain or discomfort at that time; and (2) giving the patient 2 or 3 months for that treatment to take full effect, while the patient undergoes a training, rehab, strengthening, or similar program which will focus on the treated joint, without any interference or impairment that would occur if both joints on both sides were treated in a single session. Subsequently, after the initial treatment on one side has fully settled in and stabilized, the second joint will be treated, and that second treatment will require its own rehab, strengthening, or similar program following the treatment.

Other situations also arise in which stromal cell treatments will provide greater benefits if repeated one or more times. For example, a number of patients who suffered from various types of problems (include the types of arthritis that involve damage to cartilage, in joints such as knees or hips) benefitted from a series of two or more treatments as disclosed herein, at the same treatment site. Patients in this category commonly reported that an initial treatment provided a large measure of relief, such as by eliminating 60 to 90 percent of the initial pain. Those patients chose to undergo a second treatment, to determine whether the second treatment could provide even more relief. Accordingly, follow-up treatments for patients in this class can be regarded as comparable to "booster" shots. When these types of repeated treatments are involved, the entire series of treatments, taken together, will require a larger volume of liposuction extract.

It also should be noted that pellets or layers of processed and compacted stromal cells, prepared as described herein, have been stored for up to six months in medical-grade freezers (which can sustain temperatures such as −80° C., which is in the temperature range of liquid nitrogen), with no signs of cell damage or loss of viability.

Accordingly, based on those initial tests that have been performed to date, the Applicant herein has discovered that if liposuction is used to extract liquefied fatty tissue in volumes of up to 120 cc (which will include a significant quantity of injected saline solution, mixed with the fatty tissue), then that 120 cc volume will enable the treating physician to meet the needs of the very large majority (such as more than about 95%) of all patients who are in need of these types of treatments, including patients who need a series of repeated treatments.

Therefore, this invention discloses a set of centrifuge cartridges which can hold and accommodate six syringes at a time, with each syringe holding 20 cc of fluid, and with all of the syringes sized to fit into a centrifuge cartridge that will fit into a "desktop centrifuge" machine.

As indicated by the name, a "desktop centrifuge" has dimensions that enable it to sit, in a stable manner at all times during loading, operation, and unloading, on top of a desk, table, laboratory-type bench, or similar furniture-type surface with a conventional height (such as from roughly mid-thigh, to slightly above waist-high, on an average adult), while providing full visual and working access to a lid or other movable top compartment which is low enough to allow an average adult of normal height to lean over, look into, and load and unload the machine while standing normally on the floor next to the desk, bench, etc. By contrast, most "free-standing" centrifuge machines designed for full-time laboratories are comparable in size to a washing machine. Numerous types of "desktop" centrifuges have been available for decades, and they are in widespread use in the offices and clinics of large numbers of physicians.

There is no need for a centrifuge cartridge to be able to fit into two or more different types of centrifuge machines, in order to meet the requirements of this invention. Instead, if a centrifuge cartridges with at least two or more wells that are sized and designed to hold 20 cc syringes is sized and suited to fit in a stable and secure manner into at least one type of conventional desktop centrifuge, then that centrifuge cartridge is regarded as being within the scope of the invention and claims disclosed herein, provided that it meets all other relevant limitations of the claims. Accordingly, one or more manufacturers can sell such cartridges as accessories, which can be purchased by the user of any particular make and model of a desktop centrifuge, who will know exactly which type of desktop centrifuge is present and available for use in any particular physician's office or clinic. This would be comparable to a car owner being able to purchase tires for any particular make and model of automobile, merely by telling someone who works at the tire store the make and model of the car.

Alternately, rather than having to address potential issues concerning the various different models of desktop centrifuges that are commonly owned and used by physicians' offices and clinics, a preferred approach to designing and making centrifuge cartridges that will hold at least two and preferably three 20 cc syringes can focus, instead, on certain types of specialized centrifuge machines that are specifically designed for preparing "platelet rich plasma" (PRP). That class of specialized equipment underwent a major restructuring in 2009, when two specific types of desktop-sized PRP units, designed for physicians' offices and clinics, were commercialized: the SMARTPReP™ system, sold by Harvest Technologies, and the MAGELLAN™ system, sold by the Arteriocyte Company.

Since the preparation of high-quality PRP (with platelet cell concentrations at least 5× greater than baseline, and preferably with reduced granulocyte cell concentrations as well) is essential for the treatments herein, and since both the SMARTPReP and MAGELLAN systems include relatively compact and reasonably-priced desktop centrifuge machines as major elements of those systems, a useful working presumption is that the large majority of any physicians' offices and clinics which specialize in "sports medicine" and/or orthopedics will have one of those two types of machines. Therefore, if syringe-holding centrifuge cartridges are manufactured and sold, which are designed and sized to hold at least two 20 cc syringes while fitting into one of those two types of PRP centrifuges, then having those simple options will enable any physician's office or clinic that has a platelet-rich plasma (PRP) centrifuge, will be able to centrifuge up to 80 or even 120 cc of liposuction extract at a time, using the methods disclosed herein, in the same desktop centrifuge that is used to prepare PRP.

A separate section, below, addresses the dimensions of centrifuge cartridges for PRP machines, and for 20 cc syringes which will fit into those types of cartridges. For now, the sections directly below summarize the major steps of the procedure, with reference to the drawings.

Finally, it should be noted that the ability to centrifuge liposuction extract fluid, while the fluid is still inside in the syringe that was used to extract it rather than transferring it to a different vessel or container for centrifugation, is highly useful and convenient, since it can avoid the requirement for additional steps and safeguards that would need to be developed and utilized, to absolutely minimize any risk of contamination and infection. Anything which can be done to minimize the number of items or surfaces which will contact any cellular or fluid material that will be injected into a patient, or which can be done to ensure the sterility of any such vessel, tubing, filter, and other device which contacts any cells or fluids that are injected into a patient, can facilitate and improve the types of connective tissue repairs described herein.

First Centrifugation Step: The Liposuction Fluid

FIG. 1 is a schematic depiction of two syringe barrels 80 and 90, held parallel to each other in a syringe-holding centrifuge cartridge 100. For purposes of description at this stage, both of the two syringes barrels 80 and 90 (which also can be called syringe cylinders, tubes, or similar terms, and which also are referred to herein simply as syringes, for convenience) are standard and conventional disposable plastic "monoject" syringes, as well known in the prior art. However, certain types of modified syringes, having wider diameters and shorter lengths to enable three fully-loaded 20 cc syringes to fit into cartridges that will fit into specialized centrifuges designed for preparing platelet-rich plasma, are also of interest herein, and are described below.

In FIG. 1, each syringe 80 or 90 holds a suitable volume (such as 20 cc) of a liposuction extract 150, taken from a patient in a single liposuction procedure, using methods such as described in Example 1. The liposuction extracts depicted in FIG. 1 have been centrifuged at about 40 G (i.e., at a rotational speed which will establish centrifugal forces that are 40 times greater than the force of gravity) for about 8 to 10 minutes. It has been established and reported, by various researchers, that centrifugal forces of up to about 40 G, imposed for 10 minutes at a time, will not substantially damage or kill the types of stromal precursor cells that are involved.

As depicted in that drawing, the "bottom" (highest density) aqueous layer 152, in each syringe, will contain a watery liquid. This layer will be adjacent to a syringe tip 82 or 92. During high-speed rotation, the syringe tips 82 and 92 will travel around the outer periphery or circumference of the syringe pathway, near the circular interior wall of the centrifuge chamber. The opposed ends 84 or 94 of the syringes are usually referred to as the opening, throat, or similar terms.

The temporary coupling of a syringe tip to a liposuction extraction cannula, during liposuction, can use a conventional "luer" fitting. That name, which came from a 19th century German instrument maker who played a major role in the early development of these devices, refers to standardized fitting sizes that are used for small fluid-handling devices. Luer fittings are divided into two major classes. So-called "luerlock" fittings (also spelled luerlok) use accommodating threads, which are enlarged (compared to typical screw threads), to make them easy to engage, and so that only about 2 rotations are required to fully and securely couple a syringe tip to a cannula or other device.

Other types of "luer" connectors which are not threaded are often called "luerslip" systems. These usually are adequate for small couplings that are used only briefly and that do not need to withstand substantial pressures. However, since any liposuction syringe as discussed herein will need to withstand centrifugation for a prolonged time, luerslip connectors would not be well-suited for such syringes. Accordingly, syringe tip 92 is shown as having luerlock threads, which have been screwed tightly into a small internally-threaded cap 99, for centrifugation. Cap 99 will press securely into a conical or similar "floor" 102, which is provided as part of a well 104 which is designed to hold syringe barrel 90.

Returning to the liquefied material contained in both syringes, the next "higher" layer 154, above aqueous layer 152, contains a thick, viscous, and relatively opaque fluidized or paste-like material, referred to herein as "spun fat" for convenience in this specification, and as "concentrated fatty tissue extract" in the claims. This "spun fat" layer will contain large numbers of cells, along with glycogen, broken collagen fibers, etc.

The uppermost (lowest density) layer 156 will be a generally clear layer of oily liquid, which will contain few if any viable cells. Oily layer 156 will be discarded.

A movable mechanical plunger tip 86 or 96, made of rubber or a flexible polymer, will rest on top of the oily layer 122, near the opening of each syringe. It will form a movable but generally watertight seal between the outer rim of the plunger tip 86 or 96, and the smooth inner surface of the syringe barrel. During the liposuction procedure, a plunger or handle device (not shown), which is small enough to travel within the syringe barrel, will have its lower tip securely attached to a rubber plunger tip 86 or 98, by means such as a threaded fitting; this will allow the plunger handle to be secured to, or removed from, the plunger tip whenever needed.

During liposuction, the surgeon will exert a gentle but firm pulling force (or a tensile or withdrawing force, or similar terms) on the plunger handle, to create a controlled level of suction inside the syringe, to extract liquefied fatty tissue from the patient's body. When a syringe barrel is sufficiently full of liquefied tissue, the fully-loaded syringe will be unscrewed from the cannula and replaced by an empty syringe, so that more liquefied tissue can be extracted. The surgeon can use as many syringes as desired, for any treatment on any specific patient. If desired, the cannula tip can remain inside the patient, each time a full syringe is replaced by an empty syringe. However, if the surgeon suspects that one or more of the inlet holes of the cannula might be clogged, the surgeon can temporarily withdraw the cannula from the patient (the affected skin area will remain anesthetized and numb), to inspect the cannula and clean it if necessary.

After a syringe loaded with fluidized liposuction extract has been properly centrifuged (such as at about 40 G for 8 to 10 minutes), watery layer 152 will be an aqueous suspension which will contain substantial numbers of stromal precursor cells. The watery liquid itself would interfere with wound healing, and should not be injected into an injury site or other targeted treatment site; therefore, the water will be removed from the stromal cell preparation, and discarded. However, rather than losing and wasting the stromal precursor cells that are contained in aqueous layer 152, the watery layer 152 preferably should be passed through a filter device, which will cause the cells to remain on the filter surface, while water passes through the filter, for disposal. Various types of commercially-available cell filters are available, which will allow a watery liquid to pass through the filter while retaining any cells suspended in the liquid. Membrane filters made of polysulfones, with pore diameters that average 13 to 15 microns, have been used by the Applicant herein with good results. Filter segments with suitable sizes (such as discs having 15 mm diameters) can be held in any suitable holding mechanism.

To illustrate the type of cell-filtering devices of interest herein, a filter segment 170 is shown in FIG. 1, embedded within centrifuge cartridge 100, and positioned for use with syringe 80. If filter 170 is embedded within cartridge 100, then at least two additional elements will also be required:

(1) a conduit which will carry the aqueous liquid from the syringe to the filter, after centrifugation;

(2) a valve device 172, which should be positioned between the syringe tip 82 and the filter material 170, to prevent oily material from contacting and coating the filter surface during the centrifugation; and, (2) a valve access port 174 (or similar means), to allow a physician or assistant to open and close valve 172 at appropriate times.

It also should be noted that if a filter and the necessary conduits and valve are provided within a centrifuge cartridge, they will reduce the "effective length" of the cartridge, which will need to hold up to three 20 cc syringes.

In addition, the risk that some quantity of oily and/or fatty material, from a liposuction extract, might contact and coat the filter media, before the cell filtering step has been completed, is another potentially important problem. This risk is increased by the fact that if a small "plug" of fatty material is positioned in the narrow tip 82 of syringe 80, it can be difficult to dislodge and displace that "plug" of fatty material, with a slightly denser watery material, no matter how long the liposuction extract is centrifuged, because of the way the fatty "plug" will be effectively forced and "wedged" into a small and narrow channel which will appear to be a "dead end" during centrifugation. Contacting and possibly coating a porous filter with even a small quantity of a thick and sticky oily material, before passing an aqueous solution through the filter, is not desirable, and in some cases it may pose a risk of seriously impairing or disrupting the cell filtering operation.

For those reasons, the filtering arrangement shown on the left side of FIG. 1, while feasible, is not a preferred design, and it is presumed that any cell filtration steps should, instead, be carried out using a separate filtration device which can be optimized for such use rather than being "squeezed" into the tight confines of a cartridge that is designed mainly to hold at least two and preferably three large syringes while spinning in a centrifuge.

Accordingly, syringe 90 (depicted on the right side of FIG. 1) shows a threaded cap 99, which has been screwed onto the threaded tip 92 of syringe 90 during the centrifugation step. During centrifugation, cap 99 will be pressed against a conical sloping (or other suitably shaped) "floor" 102, which will be provided as part of a syringe-holding "well" 104 which is provided in cartridge 100. After centrifugation has been completed, syringe 90 (and cap 99) will be lifted out of the well, a plunger handle will be screwed onto rubber plunger tip 96, and cap 99 will be unscrewed from syringe tip 92. Using the plunger, the aqueous layer 152 will then be pushed out of the syringe barrel 90, and into a filtration device and through a filter material that will allow water to pass through while retaining cells on the surface of the filter.

In one preferred embodiment, the filtration device can be a relatively small and lightweight device which can be turned either "right-side up" or "upside down", at different stages of the work, to take advantage of gravity-assisted flow during each of two different stages. When a watery liquid containing stromal precursor cells is being passed through the filter, downward flow of the watery liquid, through the filter, is beneficial. However, after that step has been completed, when the time arrives to remove and recover the cells from the surface of the filter so that the cells can be processed for reinjection back into a patient, it becomes beneficial to use a "pulse" of water which travels in a downward direction through the filter. This will allow the washing liquid to dislodge cells from a bottom surface (or underside, or similar terms) of the filter, in a way that will allow the cells to simply fall off the underside of the filter, for collection in a small cup, basin, tray, or similar receptacle that is positioned beneath the filter during the filter-washing and cell-recovery step.

As mentioned below, if a collagenase digestion step will be used, an aqueous saline solution (such as "Hanks balanced salt solution", abbreviated as HBSS) will be added to the "spun fat" layer, while the spun fat is being incubated with collagenase. Accordingly, that same type of saline solution can be used to wash the cells off a filter surface, when it is time to recover the filtered cells. The saline solution that is used to wash cells off of a filter surface can be used as part of the saline solution that will be added to the spun fat, to help promote a collagenase digestion step.

Alternately, if mechanical processing (rather than enzymatic digestion) will be used to dislodge and detach stromal precursor cells from extra-cellular collagen fibers, then it should be kept in mind that any cells which became suspended in an aqueous layer 152, created by centrifuging a liposuction extract fluid, very likely have already become detached from any extracellular collagen fibers, and therefore will not need to be passed through an additional mechanical processing step, which by its nature will necessarily inflict some level of shearing and other stresses on cells being treated. Accordingly, if a cell-containing filter-rinsing liquid is created, it likely should be held aside and not included, when the mechanical processing step is used to dislodge and detach stromal precursor cells from extra-cellular collagen fibers. The aqueous-suspended filtered cells can be added back to the other cells from the spun fat layer, once the cells from the spun fat layer have passed through the mechanical processing and are ready for final centrifugation.

After the initial centrifugation step involving the "raw" liposuction extract has been completed, to form the layers depicted by FIG. 1, the syringes (with threaded caps still attached to the threaded tips of the syringes) will be lifted out of the centrifugation cartridge, and placed in a stationary holding device, to help separate and process the layers that were formed during centrifugation. Any of several different sequences of steps can be used for the separation steps, such as the following:

(1) the plunger handle is reattached to the rubber plunger tip, which remained at all times inside the syringe barrel;

(2) the threaded cap is unscrewed from the tip of the syringe;

(3) the syringe tip is coupled to a clear conduit or device (presumably a relatively thin flexible plastic tube) that will carry the water layer to a filter device, which will allow water to pass through the filter while retaining the stromal precursor cells on the filter surface. If desired, it may be preferable to divert the first drop of fluid that emerges from each syringe, onto an absorbent material that will be discarded (such as a paper towel), so that if a small quantity of sticky fatty material formed a "plug" in the syringe tip during centrifugation, it will be diverted and disposed of, before it can contact and possibly coat and foul the filter material;

(4) the plunger handle is pushed into the syringe, until the aqueous layer has been expelled from the syringe barrel and passed through a cell filter;

(5) the syringe is then uncoupled from the cell-filtering device which handles the aqueous layer, and is coupled to a different conduit or device;

(6) the plunger handle is pushed deeper into the syringe, to expel the "spun fat" layer from the syringe (it will be a viscous paste-like compound, comparable to toothpaste) and force it into a chamber or vessel that is suited for: (i) a collagenase incubation step; (ii) a mechanical processing step as described below; or, (iii) mixing with a suitable aqueous solution, such as "Hanks balanced salt solution" and/or lecithin or a similar surfactant, before a mechanical processing step as described below;

(7) when the entire "spun fat" layer has been expelled from the syringe, the plunger handle can be pulled out of the syringe (with the rubber tip still attached to it), and the low-density oily layer can be drained and/or rinsed out of the syringe and discarded; alternately, the plunger handle can be unscrewed from the rubber tip, and the syringe barrel, with the oily layer and rubber tip still inside, can be discarded as medical waste.

If desired, the spun fat layer 112 (with a relatively small quantity of filtered cells from the aqueous solution) can be reinjected directly back into the patient, along with platelet-rich plasma. This option is indicated by the lowest box on the left-hand side of FIG. 2, which is a flowchart that summarizes the cell processing steps discussed herein. That treatment method was used by the Applicant herein in a number of early trials, with generally good results when compared to conventional treatments known in the prior art.

However, as indicated by the alternate pathway in lower right quadrant of FIG. 2, a more extensive and thorough processing method can enrich and concentrate the stromal precursor cells to a substantially higher and better level, before they are injected back into the patient. Those additional steps are described below. Because of: (i) the nature and the readily-predictable results of this type of additional processing; (ii) the visible results on processed cells, when before-and-after results are analyzed under a microscope; and, (ii) results that the Applicant has seen to date, in patients who have been tested in small-scale trials of these methods, the Applicant herein regards these additional processing steps as highly beneficial, to a point of clearly justifying the extra time and effort required by these additional steps.

Collagenase Incubation, Followed by a Second Centrifugation

As mentioned above, one approach which can be used to further concentrate stromal precursor cells from a "spun fat" layer involves: (i) incubation with collagenase, followed by (ii) a second centrifugation step.

However, it must also be understood and recognized, from the outset, that IF a cell preparation is contacted by a biologically active enzyme, prior to injection of the cells back into a human, major questions about safety and efficacy will arise, including questions about each and all of the following:

(i) the purity, safety, and effects of any collagenase enzyme that is used, especially if it is a non-human and/or genetically engineered preparation;

(ii) the presence of any residual levels of unremoved collagenase enzyme that may be present, in the treated cell preparation that is injected into the patient; and, (iii) any effects which the collagenase treatment may have had on the treated cells, as distinct from effects on extra-cellular material and debris.

Since those types of questions will be unavoidable if a collagenase treatment of a "spun fat" material is used, the laws that apply in the US (and all other developed countries) would inevitable require that extensive clinical trials must be performed, to prove to the satisfaction of the US Food and Drug Administration (or any similar agency, in any other country) that any cell preparation treated by enzymes or other biologically active chemicals will not create substantial risks of adverse long-term side effects.

Those types of issues, concerns, and problems can be avoided entirely, if purely mechanical processing is carried out, using equipment which is either disposable or autoclavable to guarantee sterility.

In view of those factors, "mechanical treatment" options, as described in more detail below, are regarded as strongly preferable to the types of "enzymatic digestion" option that is described in the remainder of this subsection.

Collagenase is a mammalian enzyme, which will cleave and break apart collagen fibers. In soft tissues, it is always active, and is part of a constant process of clearing out and removing old collagen fibers (which gradually become degraded, over a span of months, causing their strength and flexibility to become impaired), and replacing them with new collagen fibers, which constantly are being generated and secreted by various types of cells. The constant process of digesting and removing old collagen fibers, and replacing them with new collagen fibers, is directly analogous to the process of apoptosis (programmed cell death) and cell replacement, as described in the Background section.

Accordingly, if collagenase is used to digest the extra-cellular fibrous matrix that will be present but partially broken apart, in fluidized fatty tissues obtained by liposuction, the collagenase treatment can indeed help release the valuable cells from a relatively sticky and clingy extra-cellular material which will not provide any benefits to a patient (and which is likely to interfere with and impede the desired results, in most cases) by the time a liposuction fluid has been converted into "spun fat". Accordingly, a collagenase incubation step, followed by a second round of centrifugation, can theoretically be helpful, and may even be practical and useful, in some situations, for converting a mass of sticky "spun fat" into an more concentrated preparation which will contain substantially larger numbers and higher densities of stromal precursor cells, per volume.

If collagenase treatment is used, it can use commercially available collagenase, which usually is shipped and stored in dry powdered form. A low-viscosity aqueous liquid should be added to the incubation mixture, at a suitable volume, to function as a solvent and/or suspension agent. The total aqueous liquid in the mixture should be about half of the spun fat volume, and it should be noted that this fractional volume can and preferably should include the quantity of aqueous liquid that was used to wash cells off of the cell filter(s), as described above. Candidate aqueous liquids that can help promote the collagenase digestion step include a buffered salt solution known as Hank's balanced salt solution (HBSS), which preferably should not contain phenol red or any other indicator-type chemicals. If desired, a small quantity of glucose or fructose diphosphate can be added to the aqueous dilution liquid, to provide the cells with a source of energy, to help them survive the stresses that are imposed on them while they are outside the patient's body. The incubation period should utilize periodic shaking, to promote mixing (such as for 10 to 15 seconds, every 5 to 15 minutes), and the liquid mixture also can be stirred or rocked continuously. Incubation should be carried out at a temperature somewhere between about 37° C. and about 40° C., for a sufficient time to enable the enzyme to exert its effects, such as 1 hour.

After the collagenase incubation step has been completed, a second centrifugation step should be performed. Since a substantial amount of debris (including glycogen, collagen remnants, and various other types of cellular and extra-cellular debris) will be present, the digestion mixture preferably should be mixed with a substantial or large volume of a cell-free liquid, for the second centrifugation. Bovine fetal serum, and autologous platelet-poor plasma (which can be obtained from the patient's own blood, as a byproduct from the platelet-rich plasma preparation step), have been used by the Applicant herein, with good results, and other candidate liquids (including buffered salt solutions) can also be evaluated for use in this particular step, if desired, using no more than routine experimentation, where (i) cell viability levels, and (ii) cell density or concentration levels, after all processing has been completed, are the crucial criteria that must be evaluated and compared.

A volume of aqueous diluent (which will effectively perform as a washing liquid, during the second centrifugation step) that can range from about 25% up to about 90% of the total volume of the diluted mixture, can be used. This volume of liquid is not crucial, since the added aqueous liquid will simply be removed again by the centrifugation step. However, a low-viscosity aqueous liquid can facilitate and enhance the second centrifugation step, by reducing the tendency of collagenase and/or debris to interfere with the cells, as the cells (which have the highest density) are driven toward the outer tip of the tube, cone, or other container that holds the cell preparation during centrifugation.

Because of the volumes that will be involved, any cartridges that will be used for this centrifugation step preferably should not be subdivided into chambers, syringe wells, etc.; instead, the entire interior volume of any such cartridge should be "usable". It generally is preferable to provide a cone-shaped "bottom" for these types of centrifuge cartridges, to cause the pellets to be compacted into a "pellet" with a reduced size, rather than being distributed as a layer across the entire bottom of a flat-floored cartridge.

Accordingly, after centrifugation is carried out at a speed which will not damage the cells (such as at 40 G), for a sufficient time to achieve separation (which presumably will be about 8 to 10 minutes, in most cases), the supernatant can be discarded, and a compacted cell pellet or layer will be ready to be mixed with platelet-rich plasma (PRP), for injection into the patient.

Alternately, if desired, the cell pellet can be stored in a freezer for some span of time. The maximal limits for storage, without damaging the cells, have not been tested; however, cell storage for up to six months, at −80° C., has been tested, and no significant damage to or deterioration of the cells was detectable, when analyzed by staining methods (using reagents that will permeate through non-intact cell membranes, but not through the membranes of healthy and viable cells) that are designed to detect nonviable cells.

It should be noted that certain claims contain limitations which refer to, "removing at least a substantial portion of the supernatant, from the layer or pellet of cells." That phrase is intended to reflect the simple fact that it normally does not require additional steps, or a high degree of care or precision, to effectively isolate a layer or pellet of cells from a supernatant, or to treat any centrifuged fluid in a manner that exploits precise boundaries between the layers. Exact and precise boundaries, between different layers of a biological fluid, usually are not created when a centrifugation process must be kept to relatively low speeds and limited times in order to protect the viability of living cells. Therefore, when a layered fluid generated by a centrifugation process is being decanted, siphoned, pipetted, or otherwise processed to separate the layers, the typical practice in most clinical settings is to isolate the layer of interest, plus relatively small "transitional layers" above (and in some cases below) the layer of interest. Since this practice is not exact and precise, the best way to describe it, in language suited for a patent claim, is to simply assert that "at least a substantial portion" of the unwanted layer(s) are removed, from the layer or pellet of cells which are being isolated.

Mechanical Processing, to Generate Shearing Forces that Will Detach Viable Cells from Extra-Cellular Collagen and Fat As mentioned above, if a biologically active compound (such as collagenase, an enzyme) is used to treat cells which will later be injected back into a human, major questions concerning safety and efficacy will arise. Such questions are likely to require extensive clinical trials, to generate statistical data that will be sufficient to prove, to the satisfaction of regulatory experts and agencies, that any such treated cell preparations remain safe and effective, after the biochemical treatment.

By contrast, if mechanical processing is used, in which the cells are contacted during such processing only by reliably sterile surfaces (which can be ensured by means of proper clinical procedures, using devices that are either disposable or autoclavable), the most difficult and problematic questions can be simply and cleanly avoided, and a strong presumption will arise that extensive clinical trials will not be required, since the cells themselves will not be altered in any way, except by gently prying them away from collagen fibers in the extracellular debris.

Finally, it should be noted that if mechanical-only cell separating is done, the only truly necessary quality control involves simply checking a small sample of the cells, in the final pellet or layer of cells, using a device such as a light microscope and a suitable staining reagent, to ensure that the large majority of the cells remain intact and viable, and have not been ruptured, lysed (i.e., broken) or otherwise killed or damaged.

Accordingly, FIGS. 3-5 are "rough schematic" drawings intended to illustrate several types of candidate extrusion and/or shearing mechanisms which can be used to separate viable stromal precursor cells, from the extracellular debris that will be present in "spun fat" created by centrifuging a liposuction extract. In addition to the three "rough" schematics in FIGS. 3-5, which are intended to show candidate mechanisms rather than detailed designs, FIG. 6 illustrates, in more detail, a preferred design for a mechanical device for separating stromal precursor cells from the extracellular matrix that is present in "spun fat".

In any of these types of devices, spun fat is mixed and diluted with a suitable buffered watery liquid (such as HBSS, mentioned above), before it is loaded into a shearing and/or extrusion device. This will render the spun fat less viscous, and help make it easier for the cells to separate and disengage from the relatively sticky extracellular materials in the spun fat. If desired, a compound such as lecithin (a relatively gentle surfactant mixture, which is already approved for contacting and treating cells that will be returned to a patient's body) also can be added to that mixture.

Turning to the candidate mechanism shown in FIG. 3, the spun fat preparation (preferably diluted with a thin aqueous buffer) is loaded into the top of separator device 200, which uses a combination of extrusion, and stirring, to generate shearing forces that will help pry cells lose from the extra-cellular collagen fibers. The main processing container 220 generally has a cylindrical shape, and can be made of a transparent material that can be sterilized in an autoclave after each use (such as clear polycarbonate). Inlet device 210 is positioned on top of the main chamber 220, so that gravity will assist in the flow and separation process. The inlet device should be provided with a pressure-tight inlet connector 212, such as a threaded "luerlock" fitting that will accommodate a syringe having a luerlock outlet.

The cell-plus-fat mixture is forced, by fluid pressure applied by the operator (such as by pushing a syringe plunger into a syringe barrel) to pass through an extruder or distributor plate 212, which can be made of one or more layers of woven screen material, or which can be a flat plate having multiple relatively small holes passing through it. Early tests indicated that extruder holes having a semi-conical shape, with an inlet diameter of 3 mm (on the top surface of the plate) and an outlet diameter of 2 mm (on the bottom surface of the plate), passing through a plate having a suitable thickness (such as 3 to 10 mm), provide good results for an initial extrusion step which will help get stirring/shearing activity in the main chamber 220 to function more efficiently.

After the diluted cell-and-fat mixture enters the main cylindrical chamber 220, it will begin to rotate, as indicated by the arrows, driven by a powered stirring mechanism 222. A conventional magnetic stirring rod 222 is illustrated, for simplicity; if desired, a more elaborate and powerful device can be used, such as a device having two or more vertical stirring paddles attached to a magnetically-drivable base.

As the watery-fatty cell suspension circles through the chamber 220, it will pass through a set of perforated "catch plates" 224. Because of surface tension factors, globules and droplets of fat and oil that are suspended in the moving watery solution will stick and cling to the catch plates, whenever they contact a surface of one of those plates. This will help "clear out" the mixture, and make it easier for the cells to be separated cleanly.

For simplicity of illustration, only one catch plate 224 is shown, in FIG. 3. In early testing, a set of 3 catch plates, mounted radially at 120 degree intervals around the outer wall of chamber 220, provided good results.

The base unit 230 preferably should be provided with a heating element, to help ensure that the suspension remains at a preferred temperature during the entire cell separating process. A temperature range of about 105° Fahrenheit (about 40 to 41° Celsius), up to about 110° F. (about 43° C.), will emulate a fever which would be very severe or permanently damaging (especially for brain and spinal tissue), in a living human (especially for brain tissue); however, it will not kill the types of stromal precursor cells of interest herein, if limited to less than 10 minutes. Therefore, recommended temperature ranges for optimization testing as disclosed herein, using any particular type of extrusion processing that has been selected by a specific research team, begin at about 103° F. and range up to about 115° F. (i.e., about 40 to 46° C.). Even higher temperatures can and should be tested, by researchers who can limit the duration of their elevated-temperature extrusion processing to shorter time periods.

Over a span of time, which in early tests has ranged from about 5 to about 20 minutes, the freed and released cells will descend to the bottom floor 240 of chamber 220. Bottom floor 240 preferably should have a sloping surface, to help convey the cells to a valved outlet port 242. If the walls of the chamber 220 are made of transparent material, the person running the separation process can monitor it visually, both to ensure that everything is moving and proceeding properly inside the chamber, and to determine when the liquid reaches a state of sufficient clarity and transparency to indicate that the large majority of the cells, initially suspended in the solution, have dropped out of solution and are ready to be removed from the chamber.

If desired, other types of treatments (which most commonly include increased salt content, increased acidity, etc.) which conventionally are used to release affinity-bound molecules from sorbent materials during affinity purification procedures, can also be tested, to determine their ability to help detach and separate the desirable stromal precursor cells, from the unwanted extra-cellular debris (including collagen fibers, glycogen, etc.) that is present in a "spun fat" mixture.

Passage of Spun Fat Through Screen-Type Layers

FIG. 4 provides a simplified depiction of an alternate type of mechanical processing which can be used to detach viable stromal precursor cells from extra-cellular debris in spun fat. In this type of system, the spun fat can be passed (driven by gentle pressure) through one or more vibrating or "tapped" screens or other permeable layers.

As used herein, the term "screen" refers to a layer of material that is made by weaving together (or otherwise assembling, such as by knitting, affixing within clamp layers or devices, etc.) a plurality of strands (which might also be called fibers, wires, threads, or similar terms, depending on what material they are made from) into a generally flat layer. Unless the strands are made of thick and/or relatively rigid material which can transmit compressive forces, a segment of screen usually will need to be secured inside a frame, bracket, or holder component, to be useful as described herein.

By contrast, the term "extrusion device (or layer)" as used herein refers to a device which is relatively rigid, and which can readily transmit vibrational-type motions throughout the entire device. Such devices can be made by a process such as: (i) creating a plurality of holes (or sslots, openings, passageways, or similar terms, as appropriate) through a relatively flat layer of solid material (such as a plastic or polymer, or an autoclavable metal) by a suitable means such as drilling, punching, laser cutting, etc.; or, (ii) using molding or similar means to manufacture a relatively flat layer of material which has an array of openings (or holes, passageways, etc.) passing through the material. In general, a regularly-spaced array of holes is preferable to a random pattern, for use as described herein. Furthermore, any such holes or passageways can be provided with tapered semi-conical shapes, to help gently pry the cells loose from the collagen fibers, as the spun fat material is gently forced through the passageways of an extruder device.

The distinction between "screens" and "extruders" is not precise, and devices can be created which are at a halfway point between those two classes of devices. If that situation arises, either term can be applied, depending on which term makes more sense when applied to a particular device.

Regardless of whether a screen device (inside a frame) or an extrusion device is used, replaceable cartridge-type devices can be created, with each "cartridge" containing a screen segment or an extrusion device, embedded in a somewhat thicker frame or border made of a flexible rubber or polymer. The slightly thicker frame component can create a water-tight seal when the screen or extruder cartridge is pressed into a corresponding slot which will position it in a desired location within a flow conduit or channel. Regardless of whether screen-type or extruder devices (or some combination of both types), two or more such devices, in sequence, can be used if desired, and the two components can have different design features, such as different hole sizes and/or spacing. In addition, passage of spun fat through an initial screen or extruder which has larger holes, and which therefore will effectively act as a distributor device, to create a more even linear flow of the thick and viscous material through the device, thereby minimizing any localized higher-pressure zones within the spun fat, can also be helpful.

Initial testing by the Applicant herein indicated that passage of a spun fat layer through a first screen or extruder having moderately large openings, (such as between 0.8 and 1.5 mm in width or diameter, when square holes in a screen or round holes in an extruder are being used), and then through a second screen having smaller openings (such as about 0.5 mm width or diameter), can enable better cell separation and purification, compared to passage through only a single screen or extruder.

However, it also should be noted that every passage of the cells, through a flow obstacle such as a screen or extruder, will inevitably impose at least some level of stress on the cells that are being treated. Therefore, keeping the number of such passages to a minimum will help reduce cell mortality. Accordingly, unless and until data from optimization testing indicates otherwise, it is presumed that passaging of spun fat through an initial "distributor" device having moderately large holes, followed by two (and only two) screens or extruder devices which are mis-aligned relative to each other (so that any given cell will need to travel through a non-linear path, to help promote better separation), can help achieve a good balance between maximal cell separation, and minimal cell damage.

If a testing program is commenced to determine truly optimal (rather than merely adequate) design and operating parameters for the use of screen-passaging to separate stromal cells from extra-cellular debris in "spun fat" from a liposuction extract, each of the following parameters will merit serious consideration, for use as a controllable variable which can be evaluated to determine the optimal dimensions for maximizing cell separation, while minimizing cell damage or mortality:

1. optimal hole sizes, for both (i) a single screen, and (ii) each screen, if two or more screens will be used;
2. optimal hole shapes. If an "orthogonal" weaving pattern is used, it will create square or rectangular holes, with corners that nominally have consistently 90 degree angles. More complex weaving patterns can be used, if desired, which can create, for example, a honeycomb pattern with hexagonal holes which do not have the relatively "sharp" corners of square or rectangular holes.

It should also be noted that the "nominal" 90 degree angles of the corners of square or rectangular holes, and the "nominal" 120 degree angles of hexagonal hole junctures, do not accurately indicate what will be actually encountered by cells that are passing through a screen. Even though the "nominal" angles of the square holes in a conventional screen are 90 degrees, the actual angles which will be created, by the interweaving of cylindrical strands which typically will have diameters at least 10 to 20 times greater than a cell diameter, will be much more complex, with a number of small acute wedge-shaped angles at each and every intersection of two strands in the screening material. Those miniature acute angles are likely to help promote better cell separation, even at slow cell-travel speeds, when a screen is used as described herein, and their effects on cell damage and mortality are likely to increase at increasing rates (possibly even approaching exponential increases), as cell travel speeds are increased. Therefore, a range of cell travel speeds (which can be controlled and modulated, by controlling pressure gradients and pumping rates) will need to be evaluated, when any particular screen dimensions and weaving pattern are being evaluated.

Alternately, those types of factors and issues can be avoided (or at least shifted to lower levels of significance) by: (i) creating a layer of plastic, polymer, metal, or similar material, and then (ii) punching, drilling, laser-cutting, or otherwise treating that sheet of material, to create an array of holes through the sheet. The holes can have any desired size, and any desired pattern (such as square grids, or "honeycomb" patterns). However, it must be noted that whenever a machining process is used on a pre-existing sheet of material, it may create a set of "directional" traits in the treated sheet. For example, if a punching or drilling process is used, the "top" side tends to have slightly rounded depressions surrounding each hole, while the "bottom" side of each hole is likely to be surrounded by small irregular spurs or fragments of material, protruding outwardly from the main sheet. Accordingly, if a screen is created by machining an already-formed sheet of material, the "direction of machining" should be recorded, and tested, as a potentially significant factor when the screen is used for separating cells from debris, in spun fat.

3. If a cell-separation screen is made from woven strands, the strand thickness(es) become a design and operating parameter which can be controlled, and which should be tested and optimized. If the strands are too thin, they can cut open and kill cells, in a manner comparable to a cheese slicer which uses a thin wire to cut through a block of cheese. This concern is aggravated by the fact that the stromal precursor cells, in a spun fat suspension, will not be surrounded by a watery liquid which will allow the cells to simply move aside and flow around an obstacle they encounter; instead, the cells will be surrounded by, and effectively embedded within, a thick, sticky, viscous mass of fatty semi-solid material from which most of the water and oil has already been removed, rendering the "spun fat" even thicker and more viscous and sticky than normal fat.

Strand diameters, in a material used to make a cell-separating screen as described herein, can be expressed as a multiple of the cell diameters. Because of the factors discussed above, a presumption arises that: (1) the strands should be made from monofilaments (either polymers, or metal wires) with smooth cylindrical surfaces, rather than from woven or braided strands of even smaller fibers; and, a good starting thickness, for optimization testing, can be provided by strands which have thicknesses (diameters) that are about 20 times greater than the relevant cell diameters. Since the diameter of a typical non-fibrous eukaryotic cell is roughly 10 microns (i.e., $1/100$ of a millimeter), this implies that a good starting thickness, for optimization testing of strands that will be used to make cell-separation screens, will be in a range of about 200 microns, or 0.2 mm.

4. The number of screens, the linear distance which separates the screens, the "linear flow" rates and speed of cell travel through the screening conduit, and the pressure gradient between the inlet and the outlet of a screen-passaging chamber, should all be treated as controllable design parameters, in any optimization testing.

5. The ability to impart vibrational, reciprocating, or other motion, to any or all of the screens, also must be considered as a testing and design parameter that can be controlled and evaluated. As described above in relation to extruder devices, such motion can be a sinusoidal-type vibration, or a tapping, hammering, or other jarring motion. In either case, frequency and amplitude can each be adjusted, and then evaluated.

6. In addition, a screen or extruder can be vibrated or tapped in a variety of patterns, such as: (i) a single back-and-forth linear motion; (ii) a rotary or elliptical motion; or, (iii) a motion which alternates between two or more different directions, such as alternating up/down and left/right vibrating or tapping.

7. In addition, various known methods can be used to introduce any one or more of several different types of energy inputs (such as sonic or ultrasonic waves, physical vibrations, or electrical fields) into a cell suspension that is being passed through one or more screen-separators. Similarly, a stirring paddle or similar device can be used to stir or agitate the cell suspension, or to otherwise subject a fat-and-cell mixture to shearing forces just before, or just after, the cells pass through a screen or extruder.

Shearing-Force Agitation of a Spun Fat Material

FIG. 5 is a simplified depiction of a fluid-handling system which will force a spun fat preparation through a conduit in which rotating, reciprocating, or otherwise moving paddles (which can also be called agitators, blades, or similar terms) are used to generate shearing forces that will help detach cells from extra-cellular collagen fibers and debris.

FIG. 5 depicts two sets of paddles, each mounted on a central vertical axle (not shown), which are angled and which are rotating in different directions, to generate shearing forces in the turbulence they will create. Any number of such rotating paddles can be used, and they do not all need to be mounted on a single centered axle; for example, a paddle system can be designed with effectively interlocking "fingers" which will "sweep" across an enclosed area, in which the "even-numbered" and "odd-numbered" paddles will be moving in opposite directions at nearly all times, except when they pause to change directions. These are matters of relatively straightforward design, and they can use sophisticated stirring systems which already have developed for either or both of two fairly common uses: (i) manufacturing of liquid mixtures which contain ingredients that do not mix well together naturally, but which must be mixed together very thoroughly, to ensure consistent quality of the complete mixture; and, (ii) storage of liquids that need to be kept mixed together thoroughly.

If those types of devices are used to generate shearing forces that will help detach stromal cells from extra-cellular debris in a spun fat material, the design and operating parameters which should be evaluated, during optimization testing, including the following:

1. The dimensions and other traits of the paddles which will be used, including their overall shape, their thickness, the shapes and contours of their edges, and the presence, size, spacing, and contours of any holes that are present in the paddle surfaces;

2. The slanted angles, rotational speeds, spacing, and placement of the paddles, within a stirring chamber;

3. The average linear speed of the cell suspension which is traveling through the stirring chamber; and, 4. whether (and to what extent) any additional energy or other inputs (such as sonic or ultrasonic waves, vibrational motion, electric fields, etc.) will also be introduced into the stirring chamber while the cells pass through it.

Extrusion Device which Uses Balloon Catheter

As noted above, FIGS. 3-5 are "rough schematics" which are intended to illustrate several candidate agitating and/or shearing mechanisms which can gently pry cells away from the extracellular debris in a "spun fat" mixture.

By contrast, the two drawings in FIGS. 6 and 7 depict a specific design which will be used as the basis for designing, fabricating, and testing prototypes of a system which, as this is being written, is preferred by the Applicant for expanded testing and evaluation.

As a brief overview, the main components of cell concentrator 300 are shown in FIG. 6, while FIG. 7 shows the same type of cell concentrator 300 with an additional component that can help increase cell viability.

In FIG. 6, cell concentrator 300 is enclosed within an outer shell 310, which has dimensions that will allow it to fit into a holding cartridge in a desktop centrifuge, of the type used to prepare "platelet rich plasma" (PRP). As described in the Background section, most modern clinics and offices that specialize in "sports medicine" and/or orthopedics work will already have a PRP centrifuge, on site, since platelet cells (which can be obtained from a sample of blood from the same patient who needs repair work) are heavily and actively involved in tissue repair. Accordingly, cell concentrator 300 is designed to fit into a centrifuge cartridge that will fit into a conventional type of PRP centrifuge.

As an additional prefatory comment, cell concentrator 300 is designed to enable all necessary steps to be carried out with a high level of sterility. These devices will be manufactured and then packaged in sealed sterile envelopes, to be used once (as a disposable component) during an operation on a specific patient, and then discarded as medical waste. Although the inlet and outlet fittings are not shown in detail on FIGS. 6 and 7, the inlet port 322 for the spun fat, and the outlet port 314 for extruded cells, will be provided with sterile fittings which will allow secure attachment of a tube or syringe device, such as conventional "luer"-type (or "luerlock") fittings. Those inlet and outlet attachment components will be covered and protected by caps that are left in place until immediately before a connection is made. If a clinic has a "sterile hood" or "glove box" available, those can be used to handle and manipulate these devices with even higher levels of assured sterility; however, hoods and glove boxes are large and expensive, and most clinics that specialize in sports medicine do not have or use them, so the cell concentrator devices disclosed herein are designed to not require them.

As a feature which illustrates that comment, the main outer shell 310 has an accommodating cap 320 which will be affixed to it (such as by threads, slots, or glue), during manufacture. This will enable positioning and securing of the internal components inside the main cylinder, while the top end of the main shell 310 is open and accessible, during manufacture. Once the cap 320 has been secured to the main shell 310, the assembled device 300 will be sealed inside a sterile envelope and shipped to a physician's office or clinic, and the device will be used by the physician without ever removing cap 320 from main shell 310.

Cap 320 has a first inlet 322 (which also can be called an orifice, opening, passageway, channel, etc.) for receiving spun fat that is being forcibly expelled out of a syringe barrel that has been spun in a centrifuge. Inlet 322 (which is provided with a luer-type or similar fitting, to allow a secure water-tight attachment to be made to it) will carry the spun fat to the top opening of an extrusion cylinder 330 (discussed below), located inside the outer shell 310 of cell concentrator 300. Inlet 322 presumably should be centered, with a cone-shaped conduit which carries the spun fat to distributor plate 324 (the conduit channel is indicated by dotted lines; solid lines are used to show most internal components, since these devices very likely will be made of clear and transparent plastic or polycarbonate material, to allow the physician to visually monitor the progress of the loading, extrusion, and centrifugation steps described below).

Distributor plate 324 has relatively large holes passing through it. It can be molded into (or otherwise affixed to) either the cap 320, or the top of extrusion cylinder 330 (discussed below); either way, the goal and purpose of distributor plate 324 is to load and distribute the spun fat evenly, around an "inner annular gap" 331 which surrounds an elongated balloon catheter 340, positioned in the center of extrusion cylinder 330.

Cap 320 also has a second conduit 326 (also with a luer-type or similar attachment fitting) passing in a generally vertical direction through cap 320. A flexible tube 328 will be coupled to the bottom outlet of conduit 326, and will carry a pressurized fluid from a physician-controlled pump, compressor, or other actuator, into balloon catheter 340, discussed below.

Moving down in FIG. 6, extrusion cylinder 330 has a number of relatively small extrusion holes 332 passing through its cylindrical wall. In FIG. 6, these are represented by several rows of extrusion holes, shown flanking the balloon catheter 340 so that they will not interfere with the view of that balloon catheter. In an actual working unit, there will be a fairly large number of extrusion holes, such as at least about 50, and up to about 500 holes, evenly spaced around the circumference and length (or at least most of the length; bands around the top and bottom regions might not have holes) of extrusion cylinder 330. Alternately, cylinder 330 can be made from a segment of screen, woven from fibers of suitable material and diameters, with suitable spacing.

In FIG. 6, the bottom surface 334 of cylinder 330 is shown as being solid. However, it can be perforated if desired, or it can be formed from screen material, in a manner comparable to the toe of a sock.

After spun fat has been loaded into the inner annular gap 331, between extrusion cylinder 330 and balloon catheter 340, the extrusion process will be driven and controlled by forcibly injecting a compression fluid (such as air, an inert gas, or a liquid such as buffered saline solution) into the balloon catheter 340. Catheter 340 has two stiff mounting rings 342 and 344, surrounding its top and bottom ends, which provide a means for a plurality of radial struts 345 to hold the catheter 340 in position, aligned lengthways along the main axis in the center of extrusion cylinder 330.

A flexible, expandable, inflatable polymeric membrane 346, generally in the shape of a flattened tube when not inflated, extends the length of the balloon catheter 340, between upper and lower mounting rings 342 and 344. When air, an inert gas, or a liquid is forcibly driven into the inflatable membrane 346, that membrane will expand, thereby enlarging the volume of the balloon. This will forcibly displace the spun fat out of the inner annular gap 331, through the extrusion holes 332, and into the outer annular gap 311. Preferably, the balloon should be designed and sized so that its volume, when inflated, can occupy essentially the entire volume of extrusion cylinder 330, with the side walls of the balloon pressing directly against the interior wall of the extrusion cylinder.

Balloon catheter devices are well-known, and have been developed extensively, and used for decades, for medical uses such as minimally-invasive manipulation of clogged arteries. In a typical blood vessel procedure, a balloon catheter having an appropriate diameter and length is "snaked" (using a long hollow tube as the handle) into the site of a fatty, cholesterol-laden "plaque" that is clogging or blocking an artery. The balloon is then inflated, by forcibly pumping a small quantity of a non-compressible, non-toxic liquid (such as a buffered and/or supplemented saline solution) through the hollow tube and into the inflatable balloon. As the balloon expands, it forcibly compresses and flattens the "plaque" that was clogging the artery, thereby opening a larger channel for blood flow through the plaque. In most cases, an expandable mesh device called a "stent" is then inserted into the newly-opened channel which passes through the flattened plaque, and left in that position as the catheter is withdrawn, to help ensure that the clogging problem will not recur (at least, not at that location) for at least several years.

As mentioned above, balloon catheters are well-known, and have been used for decades. Illustrations and descriptions can be easily found on the websites of surgical supply companies which manufacture and sell them, such as, for example, the websites of Boston Scientific, Medtronics, Spectranetics, and Teleflex Medical.

In addition, any company which sells balloon catheters will also sell at least one type of inflator control device which it recommends, for use with its inflatable catheters. One example is the ENCORE™ inflator device sold by Boston Scientific. As described and illustrated at www.bostonscientific.com/en-US/products/accessories/encore.html, this device allows a physician to forcibly inflate and expand a balloon catheter by manually rotating a handle at one end of a large-diameter threaded shaft. As that shaft is forcibly screwed into an accommodating liquid-tight cylinder, the travel of that shaft, into the cylinder, forcibly drives a noncompressible liquid (such as aqueous saline solution) out of the opposing end of the cylinder, and into the balloon catheter. Therefore, the ability to rotate a handle attached to a threaded shaft provides a trained physician with a good sense of "feel" for what is happening inside an artery, as the catheter expands. That sense of "feel" is further enhanced by the physician being able to watch a live image of the balloon catheter as it inflates and expands, using video images that are similar to X-rays, on machine called a fluoroscope. This allows the physician to see and monitor the progress of the catheter expansion, as he rotates the handle which drives the displacing shaft deeper into the pump cylinder.

That level of control and "feel", which is very useful for helping prevent damage to a fragile artery which is being manipulated and altered inside a patient, will not be necessary for pressing "spun fat" through an extrusion cylinder in a beaker or similar container. Instead, a consistent and known level of pressure (which can be made to increase gradually at the start of the extrusion process, and gradually taper off as the final inflation level is approached) is likely to be preferred, whenever a particular combination of balloon catheter and extrusion cylinder are being used (that optimal pressure, for any particular device, will depend on factors such as the number and sizes of the extrusion holes, in the extrusion cylinder or screen). In addition, to help minimize abrupt motions which might create shear or other forces which could damage the cells, a presumption arises that an optimal "plateau" pressure for inflating a balloon catheter and extruding cells should be approached gently and gradually, at the start of the extrusion process, and should gradually be tapered off, as the final inflation volume is approached.

Alternately or additionally, a quick and simple visual viscosity test (which can involve, for example, watching to see how many seconds it will take for a standardized metal rod to descend downward, through a sample of spun fat from a specific patient) can be used to determine the optimal pressure level for extruding a batch of spun fat from any particular patient.

Accordingly, by using the type of device shown in FIG. 6, a "spun fat" preparation, containing stromal precursor cells clinging to a sticky extra-cellular matrix of unwanted debris, can be forcibly extruded through a large number of small holes, in a manner which provides maximal cell separation, with minimal cell damage. As shown by the directional arrows in FIG. 6, the extruded material will be forced out of the "inner annulus" 331, inside extrusion cylinder 330, into the "collection annulus" 311, located between extrusion cylinder 330 and outer shell 310. As the extruded cells, collagen fibers, fat, oil, and debris pass through the holes of extrusion cylinder 330, they will fall downward, pulled by gravity, toward the bottom of outer shell 310, which has a tapered lower end 312 which leads to an outlet port, which will have an attachment component (such as a luer or luerlock fitting), which will be covered and sealed by a cap during the extrusion and centrifuging steps.

A complete extrusion process is likely to involve two or more cycles of: (1) loading a volume of spun fat into the extrusion cylinder; (2) forcing the fat out of the cylinder, by inflating the balloon; and, (3) deflating the balloon, to make room for another batch of spun fat.

When the desired number of cycles has been completed and the collection annulus 311 is suitably full, the spun fat supply conduit, and the connecting tube used to inflate the balloon catheter 340, will be detached from inlets 322 and 326, and the cell concentrator 300 (containing the extrusion mixture) will be loaded into a centrifuge cartridge. A centrifuging step, carried out at a speed and duration which will not damage the cells (as discussed above) will cause the cells (which are filled with cytoplasm, an aqueous liquid which is denser than oil) to be driven to the lowest region of the conical tip of cell concentrator 300, while the fat, oil, and collagen fibers will form other layers higher up in the tube.

A highly enriched cell population can then be removed from the concentrator 300, by forcing or suctioning them out of the outlet 314 at the bottom of conical floor 312 of device 300. This enables the concentrated cells to be subsequently injected back into the patient, while leaving the fat, oil, and collagen fibers in the collection annulus 311 of cell concentrator 300, to be discarded as medical waste.

It is possible to use a gas, such as ambient or filtered air, or nitrogen, to inflate the balloon, since the pressurized fluid will remain inside the balloon catheter, and will never contact the spun fat or cells. However, not everything works perfectly every time, and substantially less damage to the cells will be caused, if a balloon filled with an aqueous liquid (such as buffered saline, or a mixture such as Ringer's lactate or Hank's balanced salt solution) ruptures, compared to a balloon filled with compressed gas. When a gas is compressed, the reduction in volume becomes a form of energy storage, and if a balloon filled with compressed gas suddenly pops, that pent-up energy will create a concussive-type shock wave that will spread outward in all direction, killing cells in the near vicinity, and damaging cells farther away. By contrast, water is essentially incompressible, volumetrically; therefore, if a leak forms in a water-filled balloon, any stored energy will dissipate almost immediately, usually with a single small, targeted, limited spurt of water. That type of "water jet" may kill a few cells in the direct path of the jet, but it will not create a much more damaging concussive shock wave that spreads out in all directions.

Furthermore, the ability of gases to change volume, when compressed, creates a type of "disconnect" (or "uncoupling", or similar terms) between a controlled pumping action, and the result of that action. A physician's ability to "feel" what he is doing, and to reliably know what is happening as a direct result of what he is doing, would be impaired, by the use of compressible gas in a balloon catheter for forcing spun fat through an extrusion device. Using a compressible gas to inflate the balloon, in this setting, which would be analogous to trying to use a scalpel during a delicate operation which needs precision, while wearing thick padded gloves.

Finally, use of a compressible gas, to force a sticky paste-like material through extrusion holes, would be more likely to cause small high-velocity spurts of cell materials, each time a plug of material which is clogging an extrusion channel is forced through the channel by increasing pressure levels. Those types of high-velocity spurts can kill cells, so they should be avoided and minimized, whenever possible, by using a non-compressible aqueous solution, rather than a compressible gas, to inflate the balloon catheter in an extrusion device as described herein.

In view of those factors, a presumption arises that, unless actual testing indicates otherwise, the balloon catheter should be inflated by means of an aqueous liquid, rather than a gas.

Testing to date has indicated that extrusion hole diameters of about 0.5 mm are well-sized to promote a good balance between: (i) high levels of cell separation from the collagen fibers, fat, oil, and other unwanted extra-cellular components and debris in "spun fat" from a liposuction extract; and, (ii) low levels of cell damage and mortality. Rather than stating that that size is optimal, it is regarded as a good and useful starting point, and the exact dimensions and material(s) for a truly optimal extrusion cylinder can be determined using no more than routine experimentation, with 0.5 mm diameter holes as a good starting point for optimization testing. Any such testing program should evaluate, for any candidate material and operating parameters, the balance and trade-off between:
  (i) cell separation and yield levels, which should be as high as possible; and
  (ii) cell mortality levels, which should be kept as low as possible.

In addition to evaluating hole sizes, a testing program for creating truly optimized materials for making extrusion cylinders for use as described herein should evaluate as many of the following parameters as possible:
  (i) the type of machining process used to create the holes, such as drilling, punching, molding, or laser cutting, as well as weaving of fibrous strands made of various materials (including mono-filament, braided, and poly-filament) and diameters, into screens having various thread diameters and weaving densities;
  (ii) whether sharp edges (as created by drilling or punching), or rounded edges, will provide better results (rounded edges can be created by, for example, passing a polymer in front of an infrared light, heat gun, or other heat source, so that it will reach a temperature high enough to soften the plastic enough for any sharp edges around the extrusion holes to melt slightly and then re-harden);

(iii) the optimal material for the extrusion cylinder (such as plastic, metallic foil, or possibly a sputter-coated, vapor-deposition, or other coated material);

(iv) the wall thickness of the extrusion cylinder; and, if the cylinder wall is thick enough to allow shaped channels, whether the extrusion holes should have slightly or substantially conical cross-sectional shapes, with outlet diameters smaller than the inlet diameters;

(v) the optimal pressure level for pushing and driving spun fat through the extruder cylinder; and, (vi) whether the balloon inflation should be used to create an elevated pressure inside a sealed gas-tight cell concentrator 300, or whether a pressure vent or regulator should be provided, such as by attaching a small air outlet (covered by a microfine filter to prevent microbial entry), or a pressure control valve, to inlet port 222.

The results of that type of optimization research may lead to a patentable component, device, or process; however, this type of optimization is not required to create a functioning and efficient system, which can indeed be created by following the guidelines herein. Furthermore, that type of optimization testing can be performed using no more than ordinary skill in the art, by anyone who understands the desired outcome of the cell separation process, and who understands how to evaluate cell separation, mortality, and concentrations (or who can hand over batches of extruded spun fat to someone else who specializes in evaluating cell damage and viability).

Additional Device to Sequester Oils from Spun Fat

During the Applicant's testing of a cell concentrator as described above, he discovered and recognized a significant problem which had not been known previously; and, he figured out how to create an enhancement component which can minimize that problem, leading to higher and better levels of cell viability and cell yield.

The problem the Applicant recognized was that, if spun fat is passed through an extrusion device which is well-suited for prying cells loose from collagen fibers, fat, and extra-cellular debris, so that the cells can be further concentrated, the liquefied oil and fat which are released, by the spun fat, becomes seriously toxic to the cells, within the time frame that is required by extrusion followed by centrifugation. This factor becomes even more pronounced and serious, if the extrusion process is performed at an elevated temperature, such as about 105° F. Mildly elevated temperatures, which emulate a serious but not fatal fever, helps soften and liquefy the fatty material, which helps release its grip on the cells.

Accordingly, leaving newly-separated cells in direct contact (for a sustained period of time) with an oily fluid that was created by heated extrusion of spun fat, causes a substantial die-off and loss of viable cells. The reasons for that type of cell damage and mortality have not yet been closely studied, but it is presumed that any such oil, if given sufficient time in direct contact with the cells at a high concentration, will create an aggressively sticky coating, which will clog and foul large numbers of surface receptors which are located on the surfaces of the cells. Proper functioning of at least most of the surface receptor complexes, on any cell, are essential for the health and viability of the cell. Therefore, if those surface receptor proteins are allowed to become clogged, coated, and fouled by a thick, viscous, and sticky semi-liquefied coating, while the cells are outside the body, it is entirely reasonable (and even predictable) that that type of surface receptor fouling and disruption will begin to kill the affected cells. That type of coating and fouling activity is similar to the type of suffocation that would occur, if a human or animal had a large mass of sticky oily material forced into its windpipe and lungs.

To minimize that problem, the Inventor herein developed, and successfully tested (with good results), an optional additional component (i.e., an enhancing device) which can isolate, sequester, and remove oils and softened fatty materials from spun fat material, after the spun fat has been forced through small extrusion holes, while the entire batch of cellular material and debris remains inside the cell concentrator, without disrupting or impeding the process.

That additional component is illustrated in FIG. 7, which shows (in slightly simplified form, to help focus upon the new additional component) the same type of cell concentrator 300 that is illustrated in FIG. 6. As in FIG. 6, cell concentrator 300 contains main cylindrical shell 310, cap 320, an extrusion cylinder 330 inside the main shell 310, and a balloon catheter 340 inside the extrusion cylinder 330. The additional component is an oil sequestering ring 350, shaped as an annular (ring-shaped) disc, which travels up and down (with the aid of a handle component 351) inside the "collection annulus" 311.

Oil sequestering ring 350 comprises three layers. On its bottom surface, which will directly contact the extruded spun-fat mixture that has been forcibly driven through the holes in the side wall of extrusion cylinder 330, it has a relatively thin "lipophilic" cell filter 352. As indicated by the term "lipo-philic" (i.e., oil-attracting), that bottom filter layer 352 will actively "welcome and encourage" any oil and liquefied fat, in the "extrudate" mixture, to travel upward, into and through filter layer 352. That oily material will be pulled upward by capillary attraction, supplemented by downward pressure which can be exerted on the oil sequestering ring 350 by use of the handle component 351. The pore sizes in that thin filter layer should be small enough to block and prevent any of the stromal precursor cells from moving upward into or through filter layer 352. These types of filters are sold by numerous companies, which can be located by an internet search for "cell filters".

The thick center layer 354, shown in a side elevation view in FIG. 7, is made by packing, into the outer shell of the ring device 350, a substantial quantity of aggressively lipophilic fibers. These types of materials also are well-known and readily available, and are commonly used, in pad and roll form, for cleaning up oil spills from solid and/or water surfaces. When oils and liquefied fats contact these types of lipophilic fibers, they will permeate and settle into those fiber masses, in a stable and comfortable manner. This will effectively sequester the oil away from the stromal precursor cells, which cannot reach that packing material because of the cell-blocking filter layer 352 on the bottom surface of ring device 350.

The top layer 356 of ring 350 can be made of any suitable solid material. Its main purpose is to allow the handle component 351 to be used: (i) to move the ring device 350 upward or downward, at will, inside the collection annulus 311, even after the walls of that collection annulus 311 have become coated by sticky globs of material; and, (ii) to press the bottom surface of the ring device downward, with substantial force, into the mass of cells, oils, and debris, so that pressurized contact with the bottom surface of ring device 350 will help draw oils and fatty material up into the ring, thereby minimizing their contact with the cells, and their ability to coat, clog, and damage those cells.

If desired, additional steps can be taken to further reduce any contact between: (i) the oils and fats that have been absorbed by the ring, and (ii) the stromal precursor cells that are being concentrated within the cell concentrator 300. For example, after the extrusion processing has been completed, and the device is almost ready to be placed in a centrifuge, the cap which was placed on top of inlet 322 can be removed, the oil sequestering ring 350 can be lifted to its highest possible point by raising handle 351, and a modest quantity of a suitable aqueous solution, such as HBSS, can be loaded into the extrusion cylinder. The thin and watery aqueous solution will pass readily through the extrusion holes 332, and it will form an aqueous layer that will act as a barrier, during centrifugation, between the oil-sequestering ring 350 and its absorbed oils, and the stromal precursor cells which are lower down in the collection annulus 311.

Alternate Mechanisms for Driving the Extrusion Process

As can be readily understood by mechanical engineers or designers, various other mechanisms can be used to forcibly drive a spun fat material through an extrusion device or screen, in a cylinder which is small enough to be loaded into a centrifuge cartridge.

As a simple example, if an extrusion cylinder is created from a flexible screen, and one end of the screen is affixed to a mechanism which will forcibly roll up the screen around an elongated axle (in a manner similar to rolling up a window shade), that rolling-up action will directly decrease the volume inside the screen-cylinder, in a manner which will forcibly eject the spun fat from the inside of the screen-cylinder, out through the holes in the screen.

Another type of ejection mechanism is illustrated in FIG. 8, which depicts a threaded shaft 440, having an outside diameter which is almost as large as the internal diameter of the extrusion cylinder 430. The external threads on shaft 440 pass through a set of accommodating threads which have been molded into a solid bottom floor of extrusion cylinder 430. A thin driveshaft 442, with a handle 444 at its bottom end, is reversibly affixed to the bottom of large shaft 440, so that rotation of handle 444 will forcibly drive the large shaft 440 into the interior of the extrusion cylinder 430. This will displace the spun fat, causing it to be forcibly driven out of the cylinder, through the extrusion holes in extrusion cylinder 430.

Use of Centrifugal Force to Drive Extrusion

If desired, the centrifugal force that is being exerted on a liquid, in a tube that is being actively spun in a centrifuge, can be used as the driving force which will push spun fat material through the extrusion holes in an extrusion device. Two types of devices which can accomplish that result are depicted in FIGS. 9 and 10.

FIG. 9 depicts a centrifugation cylinder 500 having an outer barrel 510, and a cap with an inlet port 522 for receiving spun fat, which will then pass through a distributor plate 524 having relatively large holes. Before centrifugation begins, the spun fat will initially rest on top of a cone-shaped extrusion barrier 530, which is positioned at a midpoint along the length of the outer barrel 510, and which has a large number extrusion holes (with relatively small diameters, such as 0.5 mm) passing through it.

If this type of cylinder 500 is used, a quantity of spun fat will be loaded into the upper chamber (i.e., the volume above extrusion barrier 530). The semi-loaded cylinder 500 will be centrifuged, preferably beginning at a relatively slow speed which can be gradually increased to a maximum chosen level over a span of a minute or more. During the spinning operation, the outward-directed centrifugal force (in a cylinder which has rotated out to a generally horizontal angle, during high-speed centrifugation) will drive the spun fat material through the extrusion holes in the extrusion barrier 530, into a collection zone 512, in a manner which will pry the stromal precursor cells loose from collagen fibers and other extra-cellular debris.

If desired, that type of "initial loading cycle" can be repeated, a second and possibly a third time. Each time the majority of the "upper chamber" has been "unloaded" (i.e., by passage of the spun fat material through the extrusion barrier, into collection zone 512, the "loading step" centrifugation can be temporarily halted, and more spun fat can be loaded into the upper chamber.

If desired, this type of system can be designed to allow an extrusion barrier to either:

(1) float, automatically, on the top surface of the liquid that has passed through the extrusion barrier; or, (2) be manually repositioned, between loading cycles.

Floating-type placement can be enabled by either or both of: (i) making the barrier from a low-density plastic, which can be made from either a consistent semi-foam type of material, or a layer or compartment which contains a low-density foam; and/or, (ii) one or more empty flotation chambers, on or near the bottom surface of the barrier.

Adjustable manual positioning can be enabled by other means, such as designing the barrier to have three or four extruding pins, distributed evenly around its outer edge, and providing pin-tracks with "detente" stops at various spaced intervals along the lengths of the tube.

In addition, the bottom (i.e., collection) compartment of the outer barrel can be provided with:

(i) one or more baffle structures (such as one or more spiral-shaped or other sloped structures which have their main axis aligned with the main axis of the centrifugation tube);

(ii) a modest quantity of a low-density cushioning foam or liquid; and/or, (iii) a segment of three-dimensional mesh (as described in the following subsection), having density and porosity traits that will provide cells with a relatively unchallenging pathway to the bottom of the tube.

Any of those three approaches (or a combination of those types of devices) would ensure that cells which emerge from the extrusion holes will not be flung a significant distance, at high speed, before impacting against a hard surface, which otherwise could damage and kill substantial numbers of cells.

A presumption applies that if viable cells are forced to cross a relatively sharp or otherwise abrasive and/or scraping edge, while under pressure, some of the cells are likely to be damaged or killed by that mechanical stress. To minimize that effect, the extrusion holes can be molded, laser-drilled, or otherwise formed at a "downward" angle, rather than having to be perpendicular to the sloping surface of the extrusion barrier 530.

An alternate design for avoiding any "turning a difficult corner" stresses on the cells, as they pass through the extrusion holes, is shown in FIG. 10. This drawing depicts an extrusion device 630 referred to herein as a "Christmas tree" extruder, because its shape somewhat resembles a Christmas tree. To simplify and clarify the drawing, the top surface 610 of cylinder 600 is shown as having a simple planar shape; in an actual design, it presumably will have the same type of structure shown in the alternate embodiment in FIG. 9, with an inlet port for spun fat, which will then pass through a distributor plate 620 with relatively large holes.

The "Christmas tree" extruder 630 has a series of annular plates 632, 634, and 636, as well as a bottom plate 638, all of which have small-diameter (e.g., 0.5 mm) extruder holes passing through them. Watertight conical walls (such as wall 633) connect the annular surfaces and the bottom plate to each other, so that no spun fat material can reach the collection zone 650, or the cell outlet port 652, without first passing through an extrusion hole in one of the annular or bottom plates.

In this manner, the cells will be driven through the extrusion holes in a direction which is fully aligned with the extrusion holes. That direction is illustrated as vertically downward, in the drawing of a stationary vertical cylinder 600 in FIG. 10; it will be radially outward, when a loaded cylinder 600 is spinning at high speed in a centrifuge.

Centrifuging Cells Through a Fibrous Mesh/Matrix

Another approach that merits early evaluation for use as described herein involves placing a three-dimensional fibrous mesh on top of either: (i) a permeable support plate, with relatively large holes passing through it; or, (ii) a loose mesh, which is designed to allow relatively rapid, easy, low-stress travel of viable cells through that loose mesh.

An example of such a device 700 is depicted in FIG. 11, which has an outer wall 710, a spun fat inlet port 720, a distributor plate with large holes 722, and an initially empty loading space 730. Loading space 730 is filled with spun fat, which is then centrifuged, presumably at a relatively low starting speed which will be gradually increased, over a span of a minute or more.

The centrifugal force will drive the spun fat through the initial fibrous mesh 740. If that mesh 740 has suitably optimized traits, this can "pry loose" the stromal precursor cells from the extra-cellular material in the spun fat, allowing the cells to be collected, in concentrated form, at the bottom of the tube.

In one embodiment, depicted in FIG. 11, mesh 740 is supported, within device 700, by a segment of a relatively loose and open low-density mesh 750, which serves as both: (i) a physical support for the higher-density mesh 740; and, (ii) a non-difficult, non-challenging pathway that will allow detached cells to weave and work their way to the bottom of the tube, for collection, rather than undergoing the risks of a high-speed "flinging" effect.

Alternate arrangements can be developed for supporting the denser mesh 740; such means can use, for example, a either a fixed permeable plate, or a movable and effectively "floating" permeable support (made of a low-density foam-type plastic or polymeric material) which can begin near the bottom of the tube, as the tube is initially filled with spun fat, and which can rise toward the top of the tube, as separated cells and debris work their way (driven by centrifugal force) through the mesh 740 and then through the holes in the floating permeable support.

Accordingly, if a "spun fat" mixture obtained from liposuction fluid is forcibly driven through one or more three-dimensional fiber matrices having density and porosity traits which have been optimized for this purpose, using a high-speed centrifuge to provide the driving force, the mesh will help "pry loose" stromal precursor cells from extra-cellular materials, in the spun fat. Accordingly, this type of design merits the type of optimization testing disclosed herein, to determine out whether a mesh-type unit can provide separated cell viability levels which are in the vicinity of 85% (or possibly even better), which has already been achieved by the Inventor herein using other systems as disclosed and illustrated herein.

Use of Specialized Centrifuging Beads, to Help Separate Cells

As yet another alternate approach which merits optimization testing, as disclosed above, to determine whether it can approach or possibly even exceed the 85% separated cell viability levels mentioned above, specialized beads having any desired density can be selected, and used to form a "lightly packed bed" which can help separate stromal precursor cells, from collagen fibers and extracellular debris in spun fat.

The term "beads" is used herein in the same manner that refers to the types of very small manufactured particles or pellets which are used in various types of biochemical separations, such as in affinity columns, chromatography columns, etc. Most of these types of beads are conventionally made from either polymer, starch, or silicone materials, and the "raw" or "core" pellets can be coated by any of numerous types of reagents (such as monoclonal antibodies, reagents to create either positive or negative ionic charges, reagents which will allow the beads to be removed from a liquid and/or affixed to other surfaces, etc.). They typically have very small diameters, usually measured in microns, and the smallest ones are invisible to the naked eye, when seen in isolation. However, they can be manufactured in any desired diameter, up to several millimeters, which is well up into the easily visible range.

Accordingly, FIG. 12 depicts a centrifuge tube 800, with an inlet port 820 for spun fat, and a distributor plate 822 leading to a loading space 830. A mass of small beads 840 is contained in the bottom of the tube, above outlet port 850.

If this design is used, the spun fat will be loaded on top of the mass of lightweight, low-density beads, inside a tube which is then centrifuged at high speed. During centrifugation, those two layers (i.e., the denser spun fat, and the lightweight beads) will end up having to swap positions. The heavier cells will be driven through the lighter beads, toward the bottom end of the tube; and, the lighter beads will be effectively trying to get out of the way of the heavier cells, and move toward the top of the tube while the heavier cells pass by on their way toward the bottom of the tube.

The net result is that the cells and the beads will bump into, push against, and jostle each other, as they move in opposite ("counter-flow") directions, in ways which will help pry the cells loose from the unwanted extra-cellular components of the spun fat.

Therefore, as above, this design (using bead-filled centrifuge tubes) merits optimization testing, to determine out whether this design can provide cell viability levels in the vicinity of 85% (or possibly even better), as achieved by the Inventor herein using extrusion devices.

Anyone contemplating this design should also note that beads of this type can be manufactured in ways that likely can enhance their cell separating-while-protecting capabilities; and, it should also be kept in mind that different types of beads, having different formulations, sizes, shapes, coatings, or other traits, can be mixed together, to create potentially even more effective mixtures. As two examples:

(1) some of the beads in a mixture can be made of aggressively lipophilic (i.e., oil-adsorbing) material, comparable to the layer of material shown in FIG. 7, for sequestering oil from the cells, to prevent the oil from coating and suffocating the cells; and, (2) some of the beads can be coated with antibodies that will bind to collagen fibers, in ways which may be able to keep the collagen fibers closer to the top of the tube, while the cells detach from the collagen and travel toward the bottom.

Accordingly, this type of "packed bed separation" may end up fitting nicely into the variety of "packed bed" arrangements and columns that are commercially available, and which are widely used both in research and in manufacturing, to separate numerous other types of biological or other chemical materials.

Additional Comments on Optimization Testing of Various Designs

Several additional comments and teachings merit attention, by anyone who is contemplating a series of optimization tests to determine which particular centrifuge tube design will perform most efficiently and optimally, in gently prying cells loose from extra-cellular debris, in a spun fat preparation.

The most important such comment, for making such tests easier, faster, and less expensive, is that such testing can be performed, using live cells and entirely realistic conditions, by using either or both of:

(1) centrifuged "spun fat" cell suspensions obtained from humans via liposuction that was carried out for weight loss purposes; and, (2) processed and centrifuged cell-containing fatty tissues obtained from cows, pigs, or other livestock that are processed at a slaughterhouse or rendering plant.

When human fat is removed via liposuction for weight loss purposes, the volume typically is measured in liters, rather than milliliters. Therefore, a single weight-loss liposuction operation can provide sufficient material to support a very large number of tests, to optimize the exact style and dimensions of the extrusion cylinder and other components (and operating parameters) for the devices described herein.

In addition, the performance of human stromal precursor cells, in mechanical separation and concentration systems, is likely to be modeled very closely by (and, indeed, may be functionally identical to the behavior of) cells from any type of large mammal, including cows, pigs, and other animals that are killed under controlled conditions in slaughterhouses. Accordingly, fatty tissues from livestock animals can provide an abundant supply of stromal precursor cells, in liquefied preparations that can be created to emulate liposuction fluids.

The foregoing methods for treating cells have been able to create preparations containing stromal precursor cells with substantially larger numbers of healthy and viable cells, than any prior treatments known to the Applicant. The best prior techniques known to the Applicant generated cell populations with roughly 50% viability levels, as indicated by cell staining tests, using well-known staining reagents, such as a standard and widely-used mixture of both acridine orange (AO) and propidium iodide (PI), since that combination allows both viable and non-viable cells to be counted, using high-speed flow cytometry equipment, This staining method (usually referred to as AO/PI staining), is well known, and is described in more detail in Example 4.

By contrast, the new techniques, which involve forcibly driving cells through an extruder device having holes that are 0.5 mm in diameter, at temperatures of about 105° F., have been able to repeatedly achieve an 85% viability level (i.e., using light microscopes and staining methods, estimates of viable cells within a microscopic field stand at roughly 85%, with the proviso that that percentage number can be clarified and established with greater accuracy by using more advanced testing methods, such as flow cytometry using large numbers of cells.

Accordingly, that 85% viability standard should now be regarded as a benchmark, against which other candidate techniques should be compared.

Now that this type of highly useful cell separation has been recognized, tested for efficacy, shown to work quite effectively, and thereby enabled by the teachings herein, any of the candidate designs disclosed herein can be tested, to determine whether any of them can reach (or possibly even surpass) the 85% cell viability levels that have already been achieved by the Applicant herein.

It should be noted that numerous types of staining reagents, fluorescent beads, and other materials that are taken in by viable cells, but not by non-viable cells, are well known to researchers, including various types of reagents that can be used in conjunction with automated equipment, such as flow cytometers, computerized analysis of photographic slides, etc. Any early-stage testing of stromal precursor cells, for viability levels after a spun fat separation process as disclosed herein, preferably should use at least two different viability-assessing reagents which act by different biochemical mechanisms, to avoid any artifacts or unforeseen problems that might arise if only a single type of test is used to measure a crucial parameter.

Dimensions for 20-CC Syringes that Will Fit into Standard Centrifuge Cartridges for PRP Machines The Applicant herein uses a SMARTPReP™ centrifuge system, sold by Harvest Technologies for creating "platelet rich plasma" (PRP), so the dimensions discussed herein are based on measurements of that system. It is believed that the relevant components of the MAGELLAN™ system have comparable dimensions, and can be adapted accordingly, for use as disclosed herein.

The SMARTPREP centrifuge has a single rotor, with two opposed and balanced "arms" mounted on opposite sides of a vertical axle which rotates at high speed. Each arm of the rotor holds a "cup" (which can also be called a basket, holder, cartridge holder, or similar terms) at the outer end of the rotor. The two cups are diametrically opposed to each other, for proper balance and minimal vibration during high-speed rotation.

Each cup is mounted at one end of the rotor arm, by means of two pins on opposite sides of the cup. Those two pins, and accommodating support mechanisms in the rotor arms, interact to form a rotatable support for each cup. This allows the "bottom" of each cup (and the bottom of a cartridge held by a cup, and the bottom of a syringe held by a cartridge) to rotate outwardly, into an essentially horizontal position during high-speed rotation, due to centrifugal force. As mentioned above, centrifugal forces should be limited to about 40 G, to avoid damage to the cells.

The following discussion, concerning the dimensions of the cartridges and cups in a PRP centrifuge, arises from the fact that, in most physicians' offices and clinics, for convenience and speed, it is preferable to be able to use a single desktop centrifuge for both of two different types of centrifugation steps (i.e., (i) for centrifuging blood, to obtain PRP; and, (ii) for centrifuging syringes that contain fatty tissues and cells obtained by liposuction), without requiring substantial delays or alterations in the machine, between those two steps.

However, it should be recognized that the standard rotor arm, in a centrifuge designed for PRP isolation, can be removed and replaced by a different rotor arm, relatively quickly and without requiring any specialized tools, merely by: (i) unscrewing and removing a specialized retainer cap from the top of the vertical axle which supports the rotor arm; (ii) lifting off and removing the standard rotor arm from the vertical axle; (iii) replacing the standard rotor arm with a different rotor arm which can have a shorter length if desired; and, (iv) replacing the retainer cap on the axle, in a manner which secures the new rotor arm to the axle.

Therefore, longer and deeper rotor cups can indeed be used, to hold and support longer and deeper cartridges that are designed to hold standard-sized 20 cc syringes. This can be accomplished, fairly easily, merely by removing a standard rotor arm, and temporarily replacing it with a shorter rotor arm which will allow a deeper cup to be used without the bottom of the cup approaching too closely to the inner wall of the centrifuge chamber.

If it is decided to not use a shorter rotor arm, to enable the use of deeper cups and longer cartridges, then careful attention will need to be paid to the dimensions of the cups, cartridges, and syringes that will be involved during centrifugation of a fluidized liposuction extract.

The standard cups that normally are contained in a SMARTPReP centrifuge have internal diameters of about 3 inches (about 7.6 cm), and depths of about 3.4 inches (about 8.6 cm).

A widely used and standardized type of 20 cc syringe (made of inexpensive plastic, and designed to be discarded after a single use, to avoid risks of contamination) has an internal diameter of 1.9 cm, and a total length of 10 cm when the plunger handle has been removed. Because of the "headroom" that is available, which normally allows the cups and cartridges to swing into an outwardly horizontal position when the rotor begins to spin, it is believed that those types of standardized 20 cc syringes will be able to fit into specially-adapted centrifuge cartridges that will fit into a SMARTPReP centrifuge. However, that will create a "tight fit", which will constrain and limit the thicknesses (and therefore the strength and durability) of the "walls" and "floors" that are used to make such a centrifuge cartridge.

To provide a more "comfortable and convenient" system (rather than a crowded and compacted system that can barely fit into the available space), slightly deeper centrifuge cups can be provided, which can utilize some portion of: (i) about ¼ inch of "gap" space that exists, between the bottoms of the standard cups, and the inner wall of a centrifuge chamber, and/or (ii) about ½ inch of "headroom" space, in the area where the centrifuge cups are mounted to the ends of the rotor arms.

Alternately or additionally, somewhat shorter syringes, with syringe barrels having internal diameters wider than the 1.9 cm which is used in the standardized syringes described above, can be provided.

When accommodations are made for wall thicknesses (assuming at least 2 mm wall thicknesses for centrifuge cartridges that will be reused, and 1 mm wall thicknesses for syringes), there is sufficient room within a standard centrifuge cartridge (having an internal diameter of 3 inches, or about 7.6 cm) for three syringes, with each syringe having an internal diameter of up to about 2.6 cm.

A standard 20 cc syringe with an internal diameter of 19 mm (radius=9.5 mm) requires a calculated length of 7.035 cm to hold 20 cc of liquid; however, when the additional volume of liquid that will be contained in the syringe tip is also included, the measured length, from the inside "shoulder" surface of the syringe to the 20 cc marking line on the barrel, is only about 6.4 cm. The remaining 3.6 cm of syringe length is occupied by the tapered tip (about 1.2 cm), and the opening or "throat" portion of the syringe (about 2.4 cm).

By contrast, if a 20 cc syringe were to be manufactured with an internal diameter of 2.6 cm (radius=13 mm), it would require a calculated length of only 3.77 cm, rather than 7.035 cm as in a standard syringe, to hold 20 cc of liquid. Accordingly, if the tip and throat lengths were unchanged, a syringe with 2.6 cm internal diameter could be reduced, in total length, from 10 cm for a standard syringe, to about 6.7 cm for the modified syringe.

However, a syringe that short, wide, and "stubby" likely would not feel normal or "comfortable" in the hands of most physicians who perform liposuction. Since liposuction is an invasive procedure, in which "feel" and tactile sensations play important roles in helping a surgeon or physician remove fatty tissue without damaging surrounding tissue, a jump from 19 mm to 26 mm, in syringe diameter, would not be optimal. Instead, smaller increases in diameter, such as to about 20 to 22 mm in internal diameter, are regarded as preferable. If a syringe has an internal diameter of 21 mm, which is only 2 mm wider than a standard 20 cc syringe, it will require only 5.26 cm of length to hold 20 cc, compared to 6.4 cm for a standard syringe. That reduction in length, of nearly 1.4 centimeter compared to a standard 20 cc syringe, can provide ample clearances in all dimensions and directions.

Similarly, an increase in internal diameter of a single millimeter, from 19 mm (standard) to 20 mm (modified), could provide a reduction in overall length of about 6.7 mm, compared to a standard 20 cc syringe. That relatively modest reduction in length likely would be sufficient to provide a reasonable balance between "clearance" and "comfort", for syringes that will be short enough to fit into cartridges that will fit into PRP centrifuges such as the SMARTPReP system, in a manner that will enable two centrifuge cartridges to hold a total of six 20 cc syringes (three syringes in each cartridge) in each "run".

Accordingly, FIG. 13 is a perspective view of a centrifuge cartridge 900, which is made of clear plastic (such as an acrylic, carbonate, etc.), and which is provided with three wells 902, 904, and 906, which are sized to hold a 20 cc syringe in each well. The outer cylindrical wall 910 of cartridge 900 is also provided with a "notch" 912. This notch is sized and designed to interact with an accommodating protrusion (often called a "key" or similar terms) in the inner wall of a centrifuge cup. The notch must be properly aligned with the key, in order to insert the cartridge into the cup. This system, which is standard in PRP centrifuges, helps prevent and minimize any vibration, rotation, rattling, or other unwanted motion of the cartridge, within the cup, during high-speed centrifugation.

FIG. 14 is an overhead (plan) view of a centrifuge rotor 950, with a vertical axle 952 coupled to a motorized drive unit (not shown) having rotor arms 960 and 970, which will rotate in a horizontal plane. Arc-shaped (semi-circular) support mechanisms 962 and 972 are positioned at the ends of rotor arms 960 and 970, and each support mechanism has a pair of strong round-tip pins 964 and 974. These pins interact with accommodating attachments in a strong cup 980 (usually made of metal), which is designed to accommodate plastic cartridges in a manner which will provide evenly-distributed support to the plastic cartridges. To simplify the drawing, it is assumed herein that each plastic cartridge 900 has a "lip" around its periphery, which rests upon and is supported by the rim of the cup; therefore, the only portion of each cup 980 which is visible from above is the "key" portion of the cup, which fits into the notch (shown by callout number 912, in FIG. 13) of a plastic cartridge 900.

The suspension system which mounts each cup 980 on two diametrically-opposed pins 964 (at the end of rotor arm 960) or 974 (at the end of rotor arm 960) creates an imaginary axle which passes through each pair of pins. That "axle" arrangement allows the bottoms of cups 980, and plastic cartridges 900 (carrying loaded syringe barrels), to swing outwardly, due to centrifugal force, so that they reach an essentially horizontal (i.e., radial) position, while the centrifuge spins at high speed.

Any of several approaches can be used to ensure that syringes loaded with liposuction fluid are placed in the centrifuge cartridges in a balanced and symmetric manner, regardless of the number of loaded syringes that are involved. These options include labeling (by ink, or by raised, submerged, or etched letters, etc.) the tops of the plastic cartridges with information to establish the preferred loading sequence, as indicated by the remarks in quotes shown in FIG. 14, as follows:

(1) If only two syringes will be centrifuged (i.e., with one syringe at each end of the rotor), they should each be loaded into a well that is marked with a phrase such as "Solo or 3/3". That well should be positioned along the "centerline" of the rotor arm.

(2) If four syringes are being centrifuged, they should be loaded into the four wells that are labeled as "1 of 2" and "2 of 2", to maintain balance and symmetry.

(3) If six syringes are being centrifuged, then they must and will occupy all six wells.

If that loading sequence is used, balanced and symmetric weighting will be sustained, regardless of whether two, four, or six syringes are being centrifuged. This will avoid placing any non-symmetric stresses on the rotor, or on the supporting pins or other components. While the amount of unbalanced stresses that would be imposed on the support pins and cups (and on the machine), if a different loading sequence is used, would not be great, and would not significantly damage the machine in a single session, the types of stresses arising from even a mildly off-balanced loading should not be imposed on a centrifuge machine repeatedly (such as during multiple hundreds or thousands of different usage sessions), because stresses due to unbalanced loading will cause increased wear and degradation of various bearings, couplings, and other components, over a span of years.

It also should be noted that balancing weights, such as syringe-type barrels filled with water or any other fluid or other weights, can be used to offset and balance out any syringes that have been loaded into a centrifuge. These types of "counterweights" are conventional, and are routinely used whenever a single loaded tube, vessel, or other container (or an odd number of loaded tubes or containers) would otherwise create unbalanced loading, during centrifugation.

Indeed, in order to ensure that closely-balanced weightings will used for each and every "run" in a centrifuge machine, it is deemed advisable and preferable to provide physicians' offices that will be using this system, with a small and convenient mechanical balance (which can also be called a "balance scale" or similar terms). This type of scale can have a balance arm mounted on a centered pivoting device, having cups at each end that are shaped identically to the cups in a centrifuge, and with a needle or pointer in the middle of the balance arm, which will point vertically toward a "Proper balance" indicator when the balance arm is exactly horizontal. A plastic cartridge, pre-loaded with the full complement of loaded syringes barrels that will be centrifuged within the next few minutes, is placed into each of the two cups in the balance scale. If that balancing operation indicates that the two fully-loaded cartridges have unbalanced weights, a small quantity of water can be added to well 920 of the lower-weight cartridge, until the weights of the two loaded cartridges are exactly balanced. If and when the weights of the two cartridges are in good balance, each cartridge (with the syringes it is carrying) is simply lifted out of the balancing scale, and placed in one of the cups in the centrifuge machine.

As a final comment prior to the examples, a phrase used in certain claims, below, needs to be clarified. That phrase is, "a concentrated preparation of stromal precursor cells, having a substantially reduced quantity of extracellular material, compared to concentrated fatty tissue extract that has not been processed by the steps listed herein." As used and intended in that phrase, a "substantial reduction" is regarded, by the Applicant herein, as occurring if the amount (measured by either volume, or weight) of extracellular collagen fibers, and/or extracellular fat, is reduced by about 25% or more. In the still-early tests described herein, the levels of reduction that were seen were much higher than that. Nevertheless, a reduction of even just 25%, in the volume and quantity of unwanted and unproductive materials that will be injected into a patient (when compared to "spun fat" injections) is a highly desirable result. Therefore, that number has been chosen for use herein as a "benchmark" level for interpreting the phrase, "a substantially reduced quantity of extracellular material, compared to concentrated fatty tissue extract that has not been processed by the steps listed herein."

EXAMPLES

Example 1: Extraction of Fatty Tissue Via Liposuction

The patient will be sterilely prepped and draped. A skin wheal, typically on one side of the abdomen or in a thigh or buttocks area, will be raised, initially using a small and thin needle, such as a 27 gauge (27 G) needle, which can deliver a saline solution containing an anesthetic such as xylocaine if desired, or which can be used after a topical anesthetic (such as a benzocaine ointment) has been applied to the skin in that area. After the initial wheal is raised using a very small needle, a larger needle (such as a 3" 25 G needle) can be used, with a fanning-style injection technique, to inject 5 cc of 1% xylocaine through the subcutaneous fat. Once this has been done, an even larger needle, such as an 18 G needle, can be used if desired. When the final sharp-tipped needle is being withdrawn from the anesthetized wheal, its sharp beveled tip is used to make a somewhat enlarged nick in the skin, to accommodate an injector cannula.

A saline/xylocaine mixture is prepared using 1000 cc of 0.9% sodium chloride solution and 50 cc of xylocaine 1% with epinephrine. Of that mixture, 20 cc will be spread through the wheal area, using a rigid injector cannula coupled to a syringe. These injector cannulae are often called "Tulip injectors", because standard and preferred models are sold by a company called Tulip Products; their website, www.tulipmedical.com, describes and illustrates devices and accessories that are commonly used during liposuction procedures.

A fanning-style injection technique should generally be used to distribute the liquids under the skin, into subcutaneous fat. The cannula should be kept generally tangential to the skin surface, so that it penetrates only shallowly into the fatty layer and does not penetrate the underlying muscles or membranes. During the injection process, lateral motion of the Tulip injector tip (which releases fluid out of the cannula via orifices on the side of the tube, rather than directly from the tip of the tube) is used to break up the fat, as fluid is being injected into and passed through the area. Generally, a semi-circular area (rather than a completely round circle) is used for extraction; however, the physician can extract fluid from an area having any size and shape, depending on factors such as the surface contours of the patient's body or limb in that region.

It should also be noted that, if desired, stromal precursor cells for use in connective tissue repair as described herein can be obtained by means of a larger-volume liposuction procedure that will also serve a weight-reduction purpose. For example, if an overweight person is having knee, hip, or ankle problems (as is fairly common), then a portion of the liquefied fatty tissue which is removed during a larger-scale liposuction procedure (using general anesthesia, a relatively large extraction cannula, etc.) can be processed as described herein, to isolate and concentrate a set of stromal precursor cells which can then be injected back into one or more joints or other areas of discomfort or damage, such as into either or both of the knee or hip joints.

After a fluid injection stage has been completed, the injector cannula will be withdrawn and replaced by a Tulip extractor. If desired, an extractor cannula can be connected to a machine which can exert either: (i) a steady suction force on the extractor tube; or, (ii) a variable level of suction, which can be controlled by the surgeon (or an assistant) by various means, such as a foot pedal. However, most surgeons prefer to have manual control over the level of suction, during at least part of the procedure, so that they can feel (with their hands) what is happening during the fluid withdrawal. Accordingly, that type of suction force is created when the surgeon pulls on the handle of the plunger, which travels inside the barrel of the syringe. If desired, the surgeon can also use a "Johnnie Lok" (illustrated at www.tulipmedical.com), which is a specialized type of clip that will temporarily affix the plunger handle to the syringe barrel, in a manner which sustains a level of suction inside the syringe while the surgeon's hands are freed up to do something else.

The liquefied fatty tissue will be extracted using a fanning technique. Each time a syringe barrel (20 cc is a preferred and convenient size) approaches a point of being full, it can be detached from the Tulip extractor, moved out of the way, and replaced by an empty 20 cc syringe. The full syringe can be either set aside for a few minutes while it awaits processing, or a surgeon's assistant can immediately begin processing the fluidized fatty tissue inside the syringe.

This extracting process can be repeated until the desired amount of fat has been harvested, using any number of 20 cc syringes.

Example 2: First Centrifugation Step

When a desired number of 20 cc syringes have been filled with a fluidized liposuction extract, they are placed into two holding cartridges which are designed for use in the type of centrifuge machine the surgeon is using. As described above, a preferred approach involves screwing a small "blind" cap onto the threaded luerlock tip of each syringe, before the syringe is placed in a centrifuge cartridge.

The syringe plungers, which were used to establish suction during the liposuction process, are disengaged from the syringe barrels, before the loaded syringes are centrifuged, by unscrewing the tips of the plungers from accommodating threads in plunger tip or stopper components, made from rubber or a flexible polymer. Each rubber or polymer stopper will remain in position, within a syringe barrel, during centrifugation, and will act as a watertight cap on the liquid in the syringe, which will help maintain sterility of the contents inside the syringe.

After two cartridges have been loaded with the desired number of syringes, they preferably should be weighed or balanced against each other, to ensure that they have approximately balanced weights. Whenever appropriate, additional weight should be added to a cartridge which weighs substantially less than the cartridge it is paired against.

Once the syringes have been emplaced in the cartridge, and after the plunger handles have been removed, the cartridge is placed in the centrifuge, and is centrifuged at about 40 G, for 8 to 10 minutes.

When the centrifugation of the liposuction extract is complete, there will be three main layers, which are relatively easy to distinguish, visually. In the "bottom" of the tube will be an aqueous layer, with a substantial number of stromal stem cells; accordingly, that watery fluid will be passed through a cell-retaining filter, to keep the cells in the liquid that will be retained and used, while the water is removed. To dislodge the cells from the surface of the filter, a "pulse" of a watery liquid (such as Hanks balanced salt solution, or HBSS) will be forced through the filter.

In the "top" of the tube will be an oily liquid, which will have few if any viable cells. That layer will be discarded.

The center layer, referred to herein as a "spun fat" material will contain the majority of the viable stromal stem cells. It will be saved for subsequent processing and use.

In a number of early tests, the "spun fat" layer was mixed directly with platelet-rich plasma (PRP), using the same 2:1 ratio described below, and injected back into the patient, into a connective tissue repair site. The results of most of those tests were entirely acceptable, and those treatments provided substantial and even major benefits to most of the patients who were treated with stromal stem cells from a "spun fat" layer after a single centrifugation step.

However, additional processing steps were subsequently developed, to further purify and concentrate stromal stem cells from a liposuction extract. Those additional steps are now regarded as establishing the preferred "best practice" mode for treating a liposuction extract to concentrate stromal stem cells from the extract, before the stromal stem cells are reinjected back into a patient. Accordingly, those additional processing steps are described in the next example.

Example 3: Collagenase Treatment and Second Centrifugation

The layer of "spun fat" from the first centrifugation step will contain a substantial amount of extra-cellular debris, including glycogen particles, and strands of collagen, the fibrous protein which creates the extra-cellular matrix that holds cells together in any type of soft tissue.

As described above, one method for breaking apart and removing the remnants of the extra-cellular collagen matrix (which otherwise can cause viable stem cells in the spun fat layer to clump together in undesirable ways) involves treating the "spun fat" from the first centrifugation step (supplemented by cells that were filtered out of the watery layer that was formed during the first centrifugation), with an aqueous salt solution, and with collagenase, an enzyme that will digest and break apart collagen fibers.

As mentioned above, this type of cell-concentrating treatment, using an enzyme, is no longer preferred, since a better and faster mechanical method was subsequently developed, as described above and in Example 4, below.

Because of the volumes involved, an enzymatic incubation step (if one is performed) can be carried out in a different incubation chamber, which should be designed for placement directly into a centrifuge when the collagenase incubation step is complete. Typically, a commercially available dry bovine collagenase A type 1 preparation (sold by Sigma-Aldrich) is mixed with 25 cc of Hank's balanced salt solution (HBSS, sold by Gibco-BRL, and which should not contain phenol red indicator) to prepare a 0.2% (by weight) concentration of the collagenase. 50 cc of "spun fat" with stromal stem cells is added to the 25 cc collagenase solution, and the chamber is shaken vigorously for 5 to 10 seconds. The mixture is then incubated for an hour at 37$o$ C, with additional shaking every 10 to 15 minutes.

At the end of that incubation period, the 75 cc cell-and-collagenase mixture is diluted 9:1 (i.e., to a final 10% level), by adding 675 cc of either or both of the following: (i) commercially-available fetal bovine serum, and/or (ii) platelet-poor plasma, preferably from the same patient who is being treated (about 25 cc of platelet-poor plasma will be generated from a 60 cc aliquot of whole blood).

The resulting mixture is vigorously shaken for several seconds, to ensure that any stromal stem cells in the collagenase-treated cell preparation can be released from any remaining collagen fragments or other debris. It is then centrifuged at about 40 G for about 8 to 10 minutes. The relatively dense stromal stem cells will settle into the bottom of the centrifuge chamber. If the bottom of the chamber is flat, the stromal stem cells will form a layer; if the bottom of the chamber is conical, the stromal stem cells will form a pellet. The supernatant is discarded, and the concentrated stromal stem cells, which will be in a relatively thick and viscous material, comparable to a paste, are ready to be mixed with platelet-rich plasma (PRP).

Example 4: Cell Extrusion Driven by a Balloon Catheter

As a preferred alternative to an enzymatic incubation step using collagenase, a mechanical method and device were developed and tested, for gently dislodging and detaching stromal precursor cells from the extra-cellular collagen matrix that is normally present in the post-centrifuge "spun fat" layer that is obtained from liposuctioned material.

This mechanical approach is now strongly preferred over a collagenase incubation step, for two crucial reasons.

First, mechanical separation can be performed much more rapidly, such as within 5 minutes or less, while an adequate collagenase incubation step is likely to require at least an hour. Shorter processing periods are highly advantageous, since the viability and health of the stromal precursor cells that are injected back into the body of the patient is inversely related to the amount of time the cells spent outside the body. Results seen by the Applicant have indicated that if connective tissue cells that have been extracted from a body can be returned to that same body within about 20 minutes or so, they do not seem to suffer from a serious drop in viability. By contrast, if the cells are kept outside the body for more than an hour, a type of biochemical "shock" commences and then picks up steam, and will substantially reduce their viability.

The second major factor involves regulations and government requirements. For valid and appropriate reasons, regulatory oversight shifts into increased scrutiny and caution, if cells that have been removed from a body are treated by enzymes or other chemicals, before the cells are returned to the body. Questions will necessarily arise over the preparation and purity of the enzymes or other chemicals, over any quantities of such enzymes or chemicals that might be present a cell preparation when it is returned to the body, and over any short-term and/or long-term effects that the enzymatic or other chemical treatment might be inflicting on the cells. Those questions will need to be addressed by careful testing.

By contrast, if the cell-concentrating treatments are entirely mechanical, and if the only result of those treatments is to further concentrate the cells while reducing unwanted debris and contaminants in the final preparation, a valid presumption arises that such mechanical treatments are safe, beneficial, and effective, and are not substantively different from centrifugation or other mechanical treatments. Accordingly, heightened government scrutiny (and the additional expense of conducting clinical trials to prove safety) will not kick in, unless and until adverse results indicate that additional scrutiny should commence.

Accordingly, FIG. 6 depicts one of several types of mechanical processing systems that were developed and tested by the Applicant herein, for gently forcing a "spun fat" preparation through 0.5 mm extrusion holes. The Applicant, a highly skilled surgeon who has been doing precision work with his hands for decades, fashioned this assembly out of available materials, using a standard centrifuge tube as the outer holding device, and a smaller cylinder of plastic, drilled with a large number of holes, as the extrusion cylinder which was centered, using glued supports, inside the centrifuge tub. A deflated balloon catheter was placed inside the extrusion cylinder, and the assembly was mounted on top of a conventional electric heating surface, which was adjusted to maintain the temperature of its contents within a range of about 103 to 105° F. That slightly elevated temperature range was found to be highly beneficial, in helping promote cell dislodgement and concentration without damaging cell viability.

A quantity of spun fat, from a liposuction procedure on a human patient, was loaded into the extrusion cylinder, around the balloon catheter. The catheter was then inflated, using a standard catheter inflator with a manually rotated displacement shaft inside an outer cylinder. The expansion of the balloon catheter forcibly pressed the spun fat material out through the holes in the extrusion cylinder, into an annular collection zone which occupied the remainder of the centrifuge tube. The extruded material was then centrifuged to separate the cells (which were collected) from the extra-cellular debris and fat (which were discarded).

The processed cells were then examined for viability, using a staining reagent combination that contains both acridine orange (AO) and propidium iodide (PI). This staining method (usually referred to as AO/PI staining) is well known, and is well-suited for use with high-speed flow cytometry equipment, since it allows both viable cells, and non-viable cells to be counted very rapidly. The AO reagent will enter all cells, whether viable or dead; by contrast, the PI reagent will enter cells only if they are living and viable. As a result, living cells will appear fluorescent green, from the PI reagent, while dead cells will appear fluorescent orange, due to the combination of both AO and PI.

Based on cell counts using that system, once the Applicant optimized and became comfortable with the steps, speed, and parameters of his system, he was able to repeatedly achieve viability levels of about 85%, among the cells that were processed by the method described above.

Furthermore, after stromal precursor cells had been processed and concentrated by that device, they formed a liquid suspension which could be injected using relatively thin and small hypodermic needles, such as 18 or even 20 gauge needles. By comparison, most injections of "spun fat"

materials which has not had that type of extrusion processing require substantially larger-diameter needles, such as 12 or 14 gauge needles.

Example 5: Preparation of Platelet-Rich Plasma

To prepare a sufficient quantity of platelet-rich plasma (PRP), approximately 60 cc of blood is withdrawn from the patient. The blood can be processed directly in a SMART-PReP™ unit (sold by Harvest Technologies), which is a specialized unit that will create about 5 to 10 cc of PRP from 60 cc of whole blood. The blood should be processed promptly after withdrawal, to isolate a platelet-rich plasma extract which will be injected back into the patient; if desired, a platelet-poor plasma liquid can also be collected, and can be used during the second centrifugation step, as described above. Any platelet-rich or platelet-poor plasma preparations should be stored in a medical-grade freezer, at a suitable temperature, such as −80° C.

It should also be noted that 25 cc of platelet-poor plasma (from 60 cc of whole blood) can be passed through a "mini-heme" concentrator, which will remove most of the water, to create about 1 to 2 cc of an enriched fluid that will contain various growth factors and other polypeptides and proteins. If desired, this concentrated proteinaceous fluid can be added to the PRP liquid, before the PRP is mixed with the stem cell preparation.

The PRP preparation will be mixed with the stromal precursor cell preparation, and the mixture will be injected (with real-time imagery as a guide, such as via ultrasonic imaging) into a site in a patient's body or limb which is in need of connective tissue repair.

Thus, there has been shown and described a set of interconnected devices, machines, and methods for: (1) using minimally-invasive liposuction methods to extract stromal precursor cells from a patient who needs connective tissue repair; (2) processing the liposuction extract to create a highly concentrated preparation of stromal precursor cells, while eliminating the large majority of any extracellular fat and debris; and, (3) reinjecting the highly concentrated stromal precursor cells back into the patient, along with platelet-rich plasma if desired, at a site where connective tissue is damaged or defective. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

REFERENCES

Abuzeni, P. Z., et al, "Enhancement of Autologous Fat Transplantation With Platelet Rich Plasma," American Journal of Cosmetic Surgery 18(2): 59 (2001)
Pietrzak, W. S., et al, "Platelet rich plasma: biology and new technology," J Craniofac Surg. 16(6): 1043-54 (2005)
Maniscalco, P., et al, "The Cascade membrane: a new PRP device for tendon ruptures," Acta Biomed. 79(3): 223-6 (2008)
Hall, M. P., et al, "Platelet-rich plasma: current concepts and application in sports medicine," J Am Acad Orthop Surg. 17(10): 602-8 (2009)
Gociman, B., et al, "Caption: a filtration-based platelet concentration system," Expert Rev Med Devices 6(6): 607-10 (2009)
Lacci, K. M., et al, "Platelet-rich plasma: support for its use in wound healing," Yale J Biol Med. 83(1): 1-9 (2010)
Lopez-Vidriero, E., et al, "The use of platelet-rich plasma in arthroscopy and sports medicine: optimizing the healing environment," Arthroscopy 26(2): 269-78 (2010)

The invention claimed is:

1. A concentrator comprising:
an outer shell comprising a first end and oppositely disposed second end, the outer shell defining a first cavity;
an inner body positioned within the first cavity and operatively coupled to the outer shell, the inner body comprising a plurality of holes and defining a second cavity, wherein an annular gap is formed in the first cavity between the outer shell and the inner body;
an inlet positioned in the first end and in fluid communication with the second cavity;
an outlet positioned in the second end in fluid communication with the annular gap; and
an extrusion device configured to be positioned within the second cavity, wherein the extrusion device is configured to mechanically force a fatty tissue through the holes of the inner body;
wherein the extrusion device is a balloon catheter comprising a top portion and a bottom portion, and wherein the concentrator further comprises: a first mounting ring positioned around the top portion of the balloon catheter; and a second mounting ring positioned around the bottom portion of the balloon catheter.

2. The concentrator of claim 1, further comprising a cap operatively coupled to the first end of the outer shell, wherein the inlet is positioned in the cap.

3. The concentrator of claim 2, wherein the inlet is a first inlet and the concentrator further comprises a second inlet positioned in the cap, wherein the first inlet and the second inlet are vertically oriented in the cap.

4. The concentrator of claim 3 wherein the first inlet is positioned in a center of the cap.

5. The concentrator of claim 2, further comprising a distributor plate positioned in the second cavity.

6. The concentrator of claim 5, wherein the distributor plate is affixed to the cap.

7. The concentrator of claim 3, further comprising a flexible tube comprising:
a first end coupled to the second inlet; and
a second end coupled to the extrusion device.

8. The concentrator of claim 1, wherein the inner body and the extrusion device are cylindrically shaped.

9. The concentrator of claim 1, wherein the inlet further comprises a luer-type fitting.

10. The concentrator of claim 1, wherein the outlet further comprises a luer-type fitting.

11. A concentrator comprising: an outer shell comprising a first end and oppositely disposed second end, the outer shell defining a first cavity;
an inner body positioned within the first cavity and operatively coupled to the outer shell, the inner body comprising a plurality of holes and defining a second cavity, wherein an annular gap is formed in the first cavity between the outer shell and the inner body;
an inlet positioned in the first end and in fluid communication with the second cavity; an outlet positioned in the second end and in fluid communication with the annular gap;

an extrusion device configured to be positioned in communication within the second cavity, wherein the extrusion device is configured to mechanically force a fatty tissue through the holes of the inner body; and comprising a sequestering ring positioned within the first cavity and slidably engaged with the extrusion device.

12. The concentrator of claim 11 wherein the sequestering ring comprises a base layer, a first filter layer, and a second filter layer.

13. The concentrator of claim 12 wherein the first filter layer comprises a lipophilic cell filter.

14. The concentrator of claim 12 wherein in the second filter layer comprises lipophilic fibers.

\* \* \* \* \*